US011939361B2

(12) United States Patent
Di Pretoro et al.

(10) Patent No.: US 11,939,361 B2
(45) Date of Patent: Mar. 26, 2024

(54) COMPOSITIONS OF PEPTIDE INHIBITORS OF INTERLEUKIN-23 RECEPTOR

(71) Applicants: Janssen Pharmaceutica NV, Beerse (BE); Protagonist Therapeutics, Inc., Newark, CA (US)

(72) Inventors: Giustino Di Pretoro, Beerse (BE); Dajun Sun, Beerse (BE); Gopal Rajan, Beerse (BE); Geraldine Broeckx, Beerse (BE); Nathalie Mertens, Beerse (BE); Shu Li, Newark, CA (US); Felix Lai, Newark, CA (US); Mohammad Masjedizadeh, Newark, CA (US); Anne M. Fourie, San Diego, CA (US); Beverly Knight, San Diego, CA (US); David Polidori, Rancho Santa Fe, CA (US); Santhosh Francis Neelamkavil, Edison, NJ (US); Nishit Modi, Newark, CA (US); Ashok Bhandari, Pleasanton, CA (US); Xiaoli Cheng, Mountain View, CA (US)

(73) Assignees: Janssen Pharmaceutica NV, Beerse (BE); Protagonist Therapeutics, Inc., Newark, CA (US)

( * ) Notice: Subject to any disclaimer, the term of this patent is extended or adjusted under 35 U.S.C. 154(b) by 0 days.

(21) Appl. No.: 17/531,538

(22) Filed: Nov. 19, 2021

(65) Prior Publication Data
US 2022/0177532 A1   Jun. 9, 2022

Related U.S. Application Data

(60) Provisional application No. 63/275,222, filed on Nov. 3, 2021, provisional application No. 63/116,568, filed on Nov. 20, 2020.

(51) Int. Cl.
| | |
|---|---|
| *C07K 14/47* | (2006.01) |
| *A61K 47/26* | (2006.01) |
| *A61K 47/38* | (2006.01) |
| *A61K 47/69* | (2017.01) |
| *A61P 37/00* | (2006.01) |
| *A61K 38/00* | (2006.01) |

(52) U.S. Cl.
CPC .......... *C07K 14/4703* (2013.01); *A61K 47/26* (2013.01); *A61K 47/38* (2013.01); *A61K 47/6923* (2017.08); *A61P 37/00* (2018.01); *A61K 38/00* (2013.01)

(58) Field of Classification Search
None
See application file for complete search history.

(56) References Cited

U.S. PATENT DOCUMENTS

| | | |
|---|---|---|
| 4,684,620 A | 8/1987 | Hruby et al. |
| 4,724,229 A | 2/1988 | Ali |
| 5,192,746 A | 3/1993 | Lobl et al. |
| 5,494,897 A | 2/1996 | Ishikawa et al. |
| 5,569,741 A | 10/1996 | Coy et al. |
| 5,990,084 A | 11/1999 | Richter et al. |
| 6,087,334 A | 7/2000 | Beeley et al. |
| 6,235,711 B1 | 5/2001 | Dutta |
| 6,818,617 B1 | 11/2004 | Niewiarowski et al. |
| 7,534,764 B2 | 5/2009 | Ganz et al. |
| 7,589,170 B1 | 9/2009 | Smythe et al. |
| 7,718,598 B1 | 5/2010 | Smythe et al. |
| 8,304,382 B2 | 11/2012 | Ferreira et al. |
| 8,313,950 B2 | 11/2012 | Rovin et al. |
| 8,435,941 B2 | 5/2013 | Ganz et al. |
| 8,536,140 B2 | 9/2013 | Park et al. |
| 8,568,706 B2 | 10/2013 | Grabstein et al. |
| 8,796,418 B2 | 8/2014 | Walensky et al. |
| 8,946,150 B2 | 2/2015 | Gallagher et al. |
| 8,999,935 B2 | 4/2015 | Huang |
| 9,169,292 B2 | 10/2015 | Gallagher et al. |
| 9,273,093 B2 | 3/2016 | Bhandari et al. |
| 9,518,091 B2 | 12/2016 | Bhandari et al. |
| 9,605,027 B2 | 3/2017 | Gallagher et al. |
| 9,624,268 B2 | 4/2017 | Bourne et al. |
| 9,714,270 B2 | 7/2017 | Bhandari et al. |
| 9,809,623 B2 | 11/2017 | Bhandari et al. |
| 9,822,157 B2 | 11/2017 | Smythe et al. |
| 10,023,614 B2 | 7/2018 | Bhandari et al. |
| 10,030,061 B2 | 7/2018 | Smythe et al. |
| 10,035,824 B2 | 7/2018 | Bhandari et al. |

(Continued)

FOREIGN PATENT DOCUMENTS

| | | |
|---|---|---|
| CA | 2015761 A1 | 11/1990 |
| CN | 101307085 A | 11/2008 |

(Continued)

OTHER PUBLICATIONS

Gruschow et al. New Pacidamycin Antibiotics Through Precursor-Directed Biosynthesis. ChemBioChem 2009, 10, 355-360. (Year: 2009).*

International Preliminary Report on Patentability, dated Jul. 19, 2022, for PCT Application No. PCT/US2021/013463, filed Jan. 14, 2021, 10 pages.

International Search Report and Written Opinion, dated Jun. 3, 2021, for PCT Application No. PCT/US2021/013463, filed Jan. 14, 2021, 14 pages.

(Continued)

*Primary Examiner* — Aradhana Sasan
*Assistant Examiner* — Jia-Hai Lee
(74) *Attorney, Agent, or Firm* — Morrison & Foerster LLP

(57) ABSTRACT

The present invention relates to compositions of peptide inhibitors of the interleukin-23 receptor (IL-23R) or pharmaceutically acceptable salt or solvate forms thereof, corresponding pharmaceutical compositions, methods and/or uses for treatment of autoimmune inflammation and related diseases and disorders.

16 Claims, 9 Drawing Sheets

Specification includes a Sequence Listing.

(56) References Cited

U.S. PATENT DOCUMENTS

| | | | |
|---|---|---|---|
| 10,059,744 B2 | 8/2018 | Bhandari et al. | |
| 10,196,424 B2 * | 2/2019 | Bourne | C07K 7/02 |
| 10,278,957 B2 | 5/2019 | Anandan et al. | |
| 10,301,371 B2 | 5/2019 | Bhandari et al. | |
| 10,407,468 B2 | 9/2019 | Bhandari et al. | |
| 10,442,846 B2 | 10/2019 | Smythe et al. | |
| 10,501,515 B2 | 12/2019 | Smythe et al. | |
| 10,626,146 B2 | 4/2020 | Bhandari et al. | |
| 10,729,676 B2 | 8/2020 | Anandan et al. | |
| 10,787,490 B2 | 9/2020 | Bhandari et al. | |
| 10,941,183 B2 | 3/2021 | Bhandari et al. | |
| 11,041,000 B2 | 6/2021 | Bhandari et al. | |
| 11,111,272 B2 | 9/2021 | Bhandari et al. | |
| 2003/0166138 A1 | 9/2003 | Kinsella et al. | |
| 2003/0166514 A1 | 9/2003 | Jones et al. | |
| 2004/0052785 A1 | 3/2004 | Goodman et al. | |
| 2004/0123343 A1 | 6/2004 | La Rosa et al. | |
| 2004/0176293 A1 | 9/2004 | Peterson et al. | |
| 2006/0166881 A1 | 7/2006 | Hotchkiss et al. | |
| 2006/0183884 A1 | 8/2006 | Blaschuk et al. | |
| 2007/0032417 A1 | 2/2007 | Baell | |
| 2007/0166308 A1 | 7/2007 | Pullen et al. | |
| 2007/0191272 A1 | 8/2007 | Stemmer et al. | |
| 2007/0197430 A1 | 8/2007 | Baell et al. | |
| 2008/0019913 A1 | 1/2008 | Polt et al. | |
| 2008/0213277 A1 | 9/2008 | Sasu et al. | |
| 2008/0260820 A1 | 10/2008 | Borrelly et al. | |
| 2008/0300180 A1 | 12/2008 | Schambye et al. | |
| 2009/0053819 A1 | 2/2009 | Seymour et al. | |
| 2009/0257952 A1 | 10/2009 | Cochran et al. | |
| 2009/0325810 A1 | 12/2009 | Lapointe et al. | |
| 2010/0151487 A1 | 6/2010 | Rovin et al. | |
| 2010/0183617 A1 | 7/2010 | Herr et al. | |
| 2010/0190710 A1 | 7/2010 | Chemtob et al. | |
| 2010/0196441 A1 | 8/2010 | Sondermeijer et al. | |
| 2010/0272731 A1 | 10/2010 | Presta et al. | |
| 2010/0280098 A1 | 11/2010 | Juliano et al. | |
| 2011/0059087 A1 | 3/2011 | Lewis et al. | |
| 2011/0086024 A1 | 4/2011 | Arthos et al. | |
| 2011/0118186 A1 | 5/2011 | Schteingart et al. | |
| 2011/0142889 A1 | 6/2011 | Lee et al. | |
| 2011/0212104 A1 | 9/2011 | Beaumont et al. | |
| 2011/0282029 A1 | 11/2011 | Holmes et al. | |
| 2012/0021975 A1 | 1/2012 | Hoffmann et al. | |
| 2012/0040894 A1 | 2/2012 | Ganz et al. | |
| 2012/0071422 A1 | 3/2012 | Gallagher et al. | |
| 2012/0115930 A1 | 5/2012 | Monia et al. | |
| 2013/0029907 A1 | 1/2013 | Gallagher et al. | |
| 2013/0137123 A1 | 5/2013 | Cucchiara et al. | |
| 2013/0172272 A1 | 7/2013 | Gallagher et al. | |
| 2013/0183755 A1 | 7/2013 | Gallagher et al. | |
| 2013/0310303 A1 | 11/2013 | Eldar-finkelman et al. | |
| 2013/0338132 A1 | 12/2013 | Koshiba et al. | |
| 2014/0005128 A1 | 1/2014 | Mo et al. | |
| 2014/0193465 A1 | 7/2014 | Bhandari et al. | |
| 2014/0286953 A1 | 9/2014 | Sasu et al. | |
| 2014/0294901 A1 | 10/2014 | Bhandari et al. | |
| 2014/0294902 A1 | 10/2014 | Bhandari et al. | |
| 2014/0336110 A1 | 11/2014 | Ganz et al. | |
| 2015/0056301 A1 | 2/2015 | Kawabe et al. | |
| 2015/0118315 A1 | 4/2015 | Wilson | |
| 2015/0157692 A1 | 6/2015 | Fu | |
| 2015/0203555 A1 | 7/2015 | Gellman et al. | |
| 2015/0284429 A1 | 10/2015 | Merutka | |
| 2016/0031944 A1 | 2/2016 | Bhandari et al. | |
| 2016/0039878 A1 | 2/2016 | Gallagher et al. | |
| 2016/0145306 A1 | 5/2016 | Bourne et al. | |
| 2016/0152664 A1 | 6/2016 | Bhandari et al. | |
| 2016/0159862 A1 | 6/2016 | Bhandari et al. | |
| 2016/0199437 A1 | 7/2016 | Wilson | |
| 2016/0222076 A1 | 8/2016 | Smythe et al. | |
| 2016/0228491 A1 | 8/2016 | Wilson | |
| 2016/0368966 A1 | 12/2016 | Bhandari et al. | |
| 2017/0313754 A1 | 11/2017 | Bourne et al. | |
| 2017/0327541 A1 | 11/2017 | Bhandari et al. | |
| 2018/0022778 A1 | 1/2018 | Bourne et al. | |
| 2018/0079782 A1 | 3/2018 | Bhandari et al. | |
| 2018/0079783 A1 | 3/2018 | Bhandari et al. | |
| 2018/0099995 A1 | 4/2018 | Bhandari et al. | |
| 2018/0100004 A1 | 4/2018 | Smythe et al. | |
| 2018/0105572 A1 | 4/2018 | Bhandari et al. | |
| 2018/0148477 A1 | 5/2018 | Bhandari et al. | |
| 2019/0002500 A1 | 1/2019 | Bhandari et al. | |
| 2019/0002503 A1 | 1/2019 | Bourne et al. | |
| 2019/0016756 A1 | 1/2019 | Bhandari et al. | |
| 2019/0076400 A1 | 3/2019 | Anandan et al. | |
| 2019/0185535 A1 | 6/2019 | Smythe et al. | |
| 2019/0185536 A1 | 6/2019 | Smythe et al. | |
| 2019/0231746 A1 | 8/2019 | Anandan et al. | |
| 2019/0248870 A1 | 8/2019 | Bhandari et al. | |
| 2019/0264197 A1 | 8/2019 | Barkan et al. | |
| 2019/0270786 A1 | 9/2019 | Bhandari et al. | |
| 2019/0300590 A1 | 10/2019 | Bhandari et al. | |
| 2019/0337983 A1 | 11/2019 | Bhandari et al. | |
| 2020/0017549 A1 | 1/2020 | Bhandari et al. | |
| 2020/0017566 A1 | 1/2020 | Bourne et al. | |
| 2020/0040037 A1 | 2/2020 | Bhandari et al. | |
| 2020/0064357 A1 | 2/2020 | Cheng et al. | |
| 2020/0207822 A1 | 7/2020 | Bhandari et al. | |
| 2020/0239516 A1 | 7/2020 | Richelle et al. | |
| 2020/0239523 A1 | 7/2020 | Bhandari et al. | |
| 2020/0308229 A1 | 10/2020 | Bhandari et al. | |
| 2020/0361992 A1 | 11/2020 | Bourne et al. | |
| 2021/0009638 A1 | 1/2021 | Bhandari et al. | |
| 2021/0061872 A1 | 3/2021 | Liu et al. | |
| 2021/0147483 A1 | 5/2021 | Bourne et al. | |
| 2021/0261622 A1 | 8/2021 | Sun et al. | |
| 2021/0363185 A1 | 11/2021 | Bhandari et al. | |
| 2021/0371466 A1 | 12/2021 | Bhandari et al. | |
| 2022/0041658 A1 | 2/2022 | Bhandari et al. | |
| 2022/0185846 A1 | 6/2022 | Manthati et al. | |
| 2022/0251142 A1 | 8/2022 | Bhandari et al. | |
| 2022/0348626 A1 | 11/2022 | Smythe et al. | |
| 2022/0372099 A1 | 11/2022 | Liu et al. | |
| 2022/0402983 A1 | 12/2022 | Sun et al. | |
| 2023/0129095 A1 | 4/2023 | Bhandari et al. | |

FOREIGN PATENT DOCUMENTS

| | | |
|---|---|---|
| CN | 101358201 A | 2/2009 |
| DE | 10107707 A1 | 8/2002 |
| JP | 2011231085 A | 11/2011 |
| JP | 2016-521257 A1 | 7/2016 |
| JP | 2017-530090 A1 | 10/2017 |
| WO | 199217492 A1 | 10/1992 |
| WO | 1994/011018 A1 | 5/1994 |
| WO | 1996/017617 A1 | 6/1996 |
| WO | 199725351 A2 | 7/1997 |
| WO | 199808871 A1 | 3/1998 |
| WO | 1998/033524 A1 | 8/1998 |
| WO | 199902194 A1 | 1/1999 |
| WO | 199926615 A1 | 6/1999 |
| WO | 200006243 A2 | 2/2000 |
| WO | 200009560 A2 | 2/2000 |
| WO | 200018789 A1 | 4/2000 |
| WO | 200018790 A1 | 4/2000 |
| WO | 200023474 A1 | 4/2000 |
| WO | 200055119 A1 | 9/2000 |
| WO | 200055184 A1 | 9/2000 |
| WO | 200061580 A1 | 10/2000 |
| WO | 200168586 A2 | 9/2001 |
| WO | 2003066678 A1 | 8/2003 |
| WO | 2004011650 A2 | 2/2004 |
| WO | 2004092405 A2 | 10/2004 |
| WO | 2006032104 A1 | 3/2006 |
| WO | 2007138291 A2 | 12/2007 |
| WO | 2008/101017 A2 | 8/2008 |
| WO | 2008097461 A2 | 8/2008 |
| WO | 2008134659 A2 | 11/2008 |
| WO | 2008140602 A2 | 11/2008 |
| WO | 2009002947 A2 | 12/2008 |
| WO | 2009027752 A2 | 3/2009 |
| WO | 2010065815 A2 | 6/2010 |
| WO | 2010116752 A1 | 10/2010 |

(56) References Cited

FOREIGN PATENT DOCUMENTS

| | | |
|---|---|---|
| WO | 2010124874 A1 | 11/2010 |
| WO | 2011091357 A1 | 7/2011 |
| WO | 2011149942 A2 | 12/2011 |
| WO | 2012052205 A1 | 4/2012 |
| WO | 2013086143 A1 | 6/2013 |
| WO | 2014/059213 A1 | 4/2014 |
| WO | 2014127316 A2 | 8/2014 |
| WO | 2014/145561 A2 | 9/2014 |
| WO | 2014/165448 A1 | 10/2014 |
| WO | 2014210056 A1 | 12/2014 |
| WO | 2015054500 A2 | 4/2015 |
| WO | 2015176035 A1 | 11/2015 |
| WO | 2015/200916 A2 | 12/2015 |
| WO | 2015157283 A9 | 12/2015 |
| WO | 2015183963 A2 | 12/2015 |
| WO | 2016004093 A2 | 1/2016 |
| WO | 2016011208 A1 | 1/2016 |
| WO | 2016054411 A1 | 4/2016 |
| WO | 2016054445 A1 | 4/2016 |
| WO | 2016109363 A1 | 7/2016 |
| WO | 2016115168 A1 | 7/2016 |
| WO | 2016195663 A1 | 12/2016 |
| WO | 2016200364 A1 | 12/2016 |
| WO | 2017011820 A2 | 1/2017 |
| WO | 2017117411 A1 | 7/2017 |
| WO | 2017/165676 A1 | 9/2017 |
| WO | 2018/022917 A1 | 2/2018 |
| WO | 2018022937 A1 | 2/2018 |
| WO | 2018089693 A2 | 5/2018 |
| WO | 2018136646 A1 | 7/2018 |
| WO | 2019/051494 A1 | 3/2019 |
| WO | 2019157268 A1 | 8/2019 |
| WO | 2019/246273 A1 | 12/2019 |
| WO | 2019/246349 A1 | 12/2019 |
| WO | 2020014646 A1 | 1/2020 |
| WO | 2020/198682 A1 | 10/2020 |
| WO | 2021007433 A1 | 1/2021 |
| WO | 2021/046246 A1 | 3/2021 |
| WO | 2021/142373 A1 | 7/2021 |
| WO | 2021146441 A1 | 7/2021 |
| WO | 2021146454 A1 | 7/2021 |
| WO | 2021146458 A1 | 7/2021 |
| WO | 2022/026629 A1 | 2/2022 |
| WO | 2022/026631 A1 | 2/2022 |
| WO | 2022/026633 A1 | 2/2022 |
| WO | 2022/212696 A1 | 3/2022 |
| WO | 2022/109328 A1 | 5/2022 |
| WO | 2022/212698 A1 | 10/2022 |
| WO | 2022/212700 A1 | 10/2022 |
| WO | 2022/266060 A1 | 12/2022 |
| WO | 2023/288017 A1 | 1/2023 |
| WO | 2023/288019 A1 | 1/2023 |
| WO | 2023/288028 A1 | 1/2023 |

OTHER PUBLICATIONS

International Search Report and Written Opinion, dated Mar. 25, 2022, for PCT Application No. PCT/US2021/60183, filed Nov. 19, 2021, 11 pages.

U.S. Appl. No. 17/149,544 entitled "Peptide inhibitors of Interleukin-23 receptor and their use to treat inflammatory diseases" filed Jan. 14, 2021, 174 Pages.

U.S. Appl. No. 18/097,077, Bhandari et al., filed on Jan. 13, 2023. (Copy not submitted herewith pursuant to the waiver of 37 C.F.R. § 1.98(a)(2)(iii) issued by the Office on Sep. 21, 2004.).

Adams et al. (2013) "Investigation of peptide thioester formation via N-Se acyl transfer." Journal of Peptide Science, 19(2):65-73.

Andreu et al. (1994) "Formation of Disulfide Bonds in Synthetic Peptides and Proteins", Peptide Synthesis Protocols, 35:91-169.

Annis, et al., "[10] Disulfide bond formation in peptides". Methods Enzymol. (1997); 289: 198-221.

Ashby et al. (2009) "Plasma Hepcidin Levels Are Elevated But Responsive To Erythropoietin Therapy In Renal Disease.", Kidney International, 75(9): 976-981.

Balasubramanian et al. (Oct. 24, 2003) "RGD-Containing Peptides Activate S6k1 Through Beta3 Integrin in Adult Cardiac Muscle Cells", Journal of Biological Chemistry, 278(43):42214- 42224.

Boer et al. (2011) "Design and Synthesis of Potent and Selective α4β7 Integrin Antagonists" Journal of Medicinal Chemistry, 44(16):2586-2592.

Bowie et al. (Mar. 16, 1990) "Deciphering the Message in Protein Sequences: Tolerance to Amino Acid Substitutions" Science, 247(498):1306-1310.

Brayden et al. (Dec. 2, 2011) "Oral Peptide Delivery: Prioritizing The Leading Technologies" Therapeutic Delivery, 2(12):1567-1573.

Chang, et al., Role of disulfide bonds in the structure and activity of human insulin. Mol Cells (Dec. 2003); 16(3): 323-330.

Chatterjee et al. (2008) "N-Methylation of Peptides: A New Perspective in Medicinal Chemistry" Accounts of Chemical Research, 41(10):1331-1342.

Cheng et al., "The Biomarker Profile of PTG-200, an Oral Peptide Antagonist of IL-23 Receptor, Tracks with Efficacy in a Preclinical Model of IBD". Gastroenterology, AGA Abstracts, vol. 152, Issue 5, Supplement 1, S31, Apr. 1, 2017.

Chermahini et al., "Cyclic peptide nanocapsule as ion carrier for halides: a theoretical survey", Structural Chemistry (Oct. 2018); 29(5): 1351-1357.

Cherry et al. (Sep. 2015) "Vedolizumab: An α4β7 Integrin Antagonist for Ulcerative Colitis And Crohn's Disease" Therapeutic Advances in Chronic Disease, 6(5):224-233.

Clark et al. (2013) "Design, Synthesis, And Characterization of Cyclic Analogues of The Iron Regulatory Peptide Hormone Hepcidin." Peptide Science, 100(5):519-526.

Clark et al. (Mar. 2011) "Understanding the Structure/Activity Relationships of the Iron Regulatory Peptide Hepcidin." Chem. Biol., 18(3):336-343.

Clark, et al., "The Engineering of an Orally Active Conotoxin for the Treatment of Neuropathic Pain." Angew Chem Int Ed (Sep. 2010); 49: 6545-6548.

Craik, et al., "Potential therapeutic applications of the cyclotides and related cystine knot mini-proteins." Expert Opin Investig Drugs (May 2007); 16(5): 595-604.

Crushing Guide for Oral Medication in Residential Aged Care, Waitemata District Health Board, 2011, 2 pages.

Database EPO Proteins (Dec. 3, 2010) "Sequence from Patent W02010124874.", XP002761649, retrieved from EBI accession No. EPOP:HI656765 Database accession No. HI656765, 1 page.

Database USPTO Proteins (Dec. 17, 2012) "Sequence from patent U.S. Pat. No. 8,313,950.", XP002761650, retrieved from EBI accession No. USPOP:AGA36544 Database accession No. AGA36544, 1 page.

Davies, John S. (Aug. 2003) "The Cyclization of Peptides and Depsipeptides." J Pept. Sci., 9(8): 471-501.

De Mast et al. (2010) "Increased Serum Hepcidin And Alterations In Blood Iron Parameters Associated With Asymptomatic P. Falciparum and P. Vivax malaria" Haematologica, 95(7): 1068- 1074.

De Vega, et al., "Modulation of Protein-Protein Interactions by Stabilizing/Mimicking Protein Secondary Structure Elements." Curr Top Med Chem (2007); 7(1): 33-62.

Definition of Isostere (Feb. 5, 2015) "Medical Definition and More from Merriam-Webster Dictionary" Available on: www.merriam-webster.com/medical/isostere, 3 pages.

Delgado et al., "The uses and properties of PEG-linked proteins". Critical Reviews in Therapeutic Drug Carrier Systems (Jan. 1, 1992); 9(3-4): 249-304.

Desbenoit et al. (2010) "Reversible Metalation of A Bis-Disulfide Analogue Of The Cys*-X-Cys* Hepcidin Binding Site: Structural Characterisation Of The Related Copper Complex", Annales Pharmaceutiques Francaises, 68(6):388-396.

Dolain et al. (2010) "Inducing a-Helices in Short Oligopeptides through Binding by an Artificial Hydrophobic Cavity" Journal of the American Chemical Society, 132(16):5564- 5565.

Dubree et al. (2002) "Selective a4B7 Integrin Antagonists and Their Potential as Antiinflammatory Agents" Journal of Medicinal Chemistry, 45:3451-3457.

(56) References Cited

OTHER PUBLICATIONS

Dutta et al. (2000) "Potent Cyclic Monomeric and Dimeric Peptide Inhibitors of VLA-4 (α4ß7 Integrin)-Mediated Cell Adhesion Based on the Ile-Leu-Asp-Val Tetrapeptide", Journal of Peptide Science, 6(7):321-341.
Dutton, et al., "A New Level of Conotoxin Diversity, a Non-native Disulfide Bond Connectivity in—Conotoxin AuIB Reduces Structural Definition but Increases Biological Activity." J Biol Chem (Oct. 2002); 277(50): 48849-48857.
Fass, D., "Disulfide bonding in protein biophysics." Annu Rev Biophys (2012); 41: 63-79. Epub Dec. 20, 2011.
Fosgerau and Hoffman, "Peptide therapeutics: current status and future directions." Drug Discovery Today (2015); 20(1): 122-128.
Foster, "Deuterium Isotope Effects in Studies of Drug Metabolism", Trends Pharmacol. Sci., 5(12):524-527 (1984).
Francis, et al., "PEGylation of cytokines and other therapeutic proteins and peptides: the importance of biological optimisation of coupling techniques". International Journal of Hematology (Jul. 1, 1998); 68(1): 1-8.
Frese et al., "Modular Combination of Enzymatic Halogenation of Tryptophan with Suzuki—Miyaura Cross-Coupling Reactions." ChemCatChem. May 20, 2016, vol. 8, No. 10, pp. 1799-1803.
Ganz et al. (Sep. 2012) "Hepcidin and iron homeostasis" Biochimica et Biophysica Acta (BBA)—Molecular Cell Research, 1823(9):1434-1443.
Garcia, Josep et al. "D-Polyarginine Lipopeptides as Intestinal Permeation Enhancers" ChemMedChem (2018), 13: 2045-2052.
Gee et al. (1998) "Cyclic Peptides as Non-carboxyl-terminal Ligands of Syntrophin PDZ Domains" The Journal of Biological Chemistry, 273(34):21980-21987.
Gentilucci et al. (2010) "Chemical Modifications Designed to Improve Peptide Stability: Incorporation of Non-Natural Amino Acids, Pseudo-Peptide Bonds, and Cyclization.", Current Pharmaceutical Design, 16(28):3185-3203.
Girelli et al. (Jun. 9, 2016) "Hepcidin In The Diagnosis Of Iron Disorders" Blood, 127(23): 2809-2813.
Gombotz and Pettit, "Biodegradable Polymers for Protein and Peptide Drug Delivery". Bioconjugate Chem. (Jul. 1, 1995); 6(4): 332-351.
Gormer et al. (Feb. 1, 2010) "Efficient Microwave-Assisted Synthesis of Unsymmetrical Disulfides" The Journal of Organic Chemistry, 75(5): 1811-1813.
Guerler and Knapp, "Novel protein folds and their nonsequential structural analogs." Protein Sci (Aug. 2008); 17(8): 1374-1382.
Guharoy and Chakrabarti, "Secondary structure based analysis and classification of biological interfaces: identification of binding motifs in protein-protein interactions." Bioinformatics (2007); 23(15): 1909-1918. Epub May 17, 2007.
Gupta, et al., "A classification of disulfide patterns and its relationship to protein structure and function." Protein Sci (Aug. 2004); 13(8): 2045-2058.
Haanstra et al. (2013) "Antagonizing the a4B1 Integrin, but no a4B7, Inhibits Leukocytic Infiltration of the Central Nervous System in Rhesus Monkey Experimental Autoimmune Encephalomyelitis" Journal of Immunology, 90(5): 1961-1973.
Hartig, et al., "Intramolecular disulphide bond arrangements in nonhomologous proteins." Protein Sci Publ Protein Soc (Feb. 2005); 14(2): 474-482.
Hawe, et al., "Forced degradation of therapeutic proteins." J Pharm Sci. (Mar. 2012); 101(3): 895-913. Epub Nov. 14, 2011.
Henikoff and Henikoff, "Amino acid substitution matrices from protein blocks." Proc Natl Acad Sci U S A (Nov. 1992); 89(Nov.); 10915-10919.
Hruby et al. (1994) "Design of Novel Synthetic Peptides Including Cyclic Conformationally And Topographically Constrained Analogs", Methods in Molecular Biology, 35(11):201-241.
https://medlineplus.gov/druginfo/meds/a682145.html. Accessed Dec. 22, 2022 (Year: 2022).
https://www.cdc.gov/diabetes/basics/what-is-type-1-diabetes.html. Accessed Dec. 22, 2022 (Year: 2022).
https://www.rheumatology.org/I-Am-A/Patient-Caregiver/Diseases-Conditions/Psoriatic-Arthritis. Accessed Dec. 22, 2022 (Year: 2022).
Hudecz, et al., "Synthesis, conformation, biodistribution and in vitro cytotoxicity of daunomycin-branched polypeptide conjugates". Bioconjugate Chem. (Jan. 1, 1992); 3(1): 49-57.
Ilyin et al. (2003) "Comparative Analysis Of Mouse Hepcidin 1 And 2 Genes:Evidence For Different Patterns Of Expression And Co-Inducibility During Iron Overload 1" FEBS Letters, 542(1-3): 22-26.
International Search Report and Written Opinion for PCT/US2015/040658, dated Oct. 28, 2015, 9 Pages.
International Search Report and Written Opinion for PCT/US2016/042680, dated Jan. 13, 2017, 12 Pages.
International Search Report and Written Opinion for PCT/US2018/014257, dated May 14, 2018, 13 Pages.
International Search Report and Written Opinion for PCT/US2019/041665, dated Dec. 19, 2019, 11 Pages.
International Search Report and Written Opinion for PCT/US2020/041409, dated Dec. 3, 2020, 13 Pages.
Jackson, David Y. (2002) "Alpha 4 Integrin Antagonists", Current Pharmaceutical Design, (8)14:1229-1253.
Janssen et al. (2002) "Comparison of a Monomeric and Dimeric Radiolabeled RGD-Peptide for Tumor Targeti" Cancer Biotherapy and Radiopharmaceuticals, 17(6):641-646.
Jordan et al. (2009) "Hepcidin Revisited, Disulfide Connectivity, Dynamics, And Structure" Journal of Biological Chemistry, 284(36):24155-24167.
Kelleman et al. (2003) "Incorporation of Thioether Building Blocks Into An Avß3-Specific Rgd Peptide: Synthesis And Bioloqical Activity", Biopolymers (Peptide Science), 71(6):686-695.
Kitazume et al. (1998) "Experimental Methods In Organic Fluorine Chemistry" Gordon and Breach Science Publishers, p. 9, (3 pages).
Kluskens et al. (2009) "Angiotensin-(1-7) with Thioether Bridge: An Angiotensin- Converting Enzyme- Resistant, Potent Angiotensin-(1-7) Analog" The Journal of Pharmacology and Experimental Therapeutics, 328(3): 849-855.
Knudsen et al. (May 4, 2000) "Potent Derivatives of Glucagon-Like Peptide-1 With Pharmacokinetic Properties Suitable For Once Daily Administration" Journal of Medicinal Chemistry, 43(9): 1664-1669.
Krause et al. (2000) "LEAP-1, A Novel Highly Disulfide-Bonded Human Peptide, Exhibits Antimicrobial Activity" FEBS Letters, 480(2-3): 147-150.
Kuchar et al. (2013) "Human Interleukin-23 Receptor Antagonists Derived from An Albumin-Binding Domain Scaffold Inhibit II-23-Dependent Ex Vivo Expansion of II-17- Producing T-Cells" Proteins, 82(6): 975-989.
Legge et al. (1964) "On The Prediction Of Partition Coefficients And Rf Values Of Peptides." Aust. J. Biol. Sci, 17:561-571.
Ley et al. (Mar. 2016) "Integrin-Based Therapeutics: Biological Basis, Clinical Use and New Drugs" Nature Reviews Drug Discovery, 15(3):173-183.
Li and Roller, "Cyclization Strategies in Peptide Derived Drug Design." Curr. Topics Med. Chem. (2002); 2: 325-341.
Li et al. (2002) "Cyclization Strategies in Peptide Derived Drug Design" Current Topics in Medical Chemistry, 2:325-341.
Liu and Wang, "Endomorphins: potential roles and therapeutic indications in the development of opioid peptide analgesic drugs". Med Res Rev. (May 2012); 32(3): 536-580. Epub Feb. 1, 2011.
Liu, Shuang (2006) "Radiolabeled Multimeric Cyclic Rgd Peptides as Integrin Alphavbeta3 Targeted Radiotracers For Tumor Imaging" School of Health Science, Purdue University, Molecular Pharmaceuticals, 3(5):472-487.
Liu, Shuang, "Radiolabeled Cyclic RGD Peptides as Integrin $\alpha v\beta_3$-Targeted Radiotracers: Maximizing Binding Affinity via Bivalency." Bioconjugate Chem. (2009); 20 (12): 2199-2213.
Longobardo, et al., "Incorporation of β-amino acids in bioactive peptides: a β-casomorphin case study." Peptides 2002, Abstract P A97, Proceedings of the European Peptide Symposium, 27th, Sorrento, Italy, Aug. 31-Sep. 6, 2002 (2002), 198-199.
Longobardo, et al., "β-Casomorphins: substitution of phenylalanine with ß-homo-phenylalanine increases the μ-type opioid receptor affinity." Bioorganic & Medicinal Chemistry Letters (2000); 10(11): 1185-1188.

(56) References Cited

OTHER PUBLICATIONS

Madsen et al. (2007) "Structure- Activity and Protraction Relationship of Long-Acting Glucagon-Like Peptide-1 Derivatives: Importance of Fatty Acid Length, Polarity, And Bulkiness" Journal of Medicinal Chemistry, 50(24):6126-6132.
Maeda, et al., "Conjugates of anticancer agents and polymers: advantages of macromolecular therapeutics in vivo". Bioconjugate Chem. (Sep. 1992/Oct.); 3(5): 3511-362.
Maher, Sam et al., "Application of Permeation Enhancers in Oral Delivery of Macromolecules: An Update", Pharmaceutics (2019), 11, 41; doi: 10.3390, 23 pages.
Maher, Sam et al., "Safety and efficacy of sodium caprate in promoting oral drug absorption: from in vitro to the clinic", Advanced Drug Delivery Reviews, (2009) 61 (15): 1427-1449.
Makharia, Govind K., "Current and emerging therapy for celiac disease", Frontiers in Medicine (Mar. 2014); vol. 1, Article 6, pp. 1-11.
Muheem, Abdul et al., "A review on the strategies for oral delivery of proteins and peptides and their clinical perspectives", Saudi Pharmaceutical Journal (2016) 24, 413-428.
Munoz et al. (2011) "Disorders of Iron Metabolism. Part II: iron deficiency and iron overload" Journal of Clinical Pathology, 64(4):287-296.
NCBI Reference Sequence: NP_653302.2, "interleukin-23 receptor precursor [Homo sapiens]", Feb. 8, 2023, 4 pages.
Nemeth et al. (2006) "The N-terminus Of Hepcidin Is Essential for Its Interaction with Ferroportin: Structure-Function Study" Blood, 107(1):328-333.
Niederreiter, et al., "Anti-IL-12/23 in Crohn's Disease: Bench and Bedside." Curr Drug Targets (Nov. 2013); 14(12): 1379-1384.
Park et al. (2001) "Hepcidin, A Urinary Antimicrobial Peptide Synthesized in The Liver" Journal of Biological Chemistry, 276(11):7806-7810.
Parrow et al. (2011) "Prospects for A Hepcidin Mimic to Treat B-Thalassemia and Hemochromatosis" Expert Review of Haematology, 4(3):233-235.
Pattarawarapan (Aug. 2003) "Selective Formation of Homo- and Heterobivalent Peptidomimetics" J. Med. Chem., 46(17):3565-3567.
Pelton et al. (1985) "Somatostatin Analogs with Affinity for Opiate Receptors in Rat Brain Binding Assay" Peptides, 6(Suppl 1): 159-163.
Preza et al. (Dec. 1, 2011) "Minihepcidins Are Rationally Designed Small Peptides That Mimic Hepcidin Activity in Mice and May Be Useful For The Treatment Of Iron Overload" J. Clin. Invest, 121(12):4880-4888.
Quiniou et al. (Aug. 20, 2014) "Specific Targeting of The IL-23 Receptor, Using a Novel Small Peptide Noncompetitive Antagonist, Decreases the Inflammatory Response" American Journal of Physiology-Regulatory, Integrative and Comparative Physiology, 307(10): R1216-R1230.
Ramos et al. (Nov. 1, 2012) "Minihepcidins Prevent Iron Overload in a Hepcidin- deficient Mouse Model of Severe Hemochromatosis", Blood, 120(18):3829-3836.
Rivera et al. (Sep. 15, 2005) "Synthetic Hepcidin Causes Rapid Dose-Dependent Hypoferremia And Is Concentrated in Ferroportin-Containing Organs" Blood, 106(6):2196- 2199.
Rostovtsev et al. (Jul. 15, 2002) "A Stepwise Huisgen Cycloaddition Process: Copper(I)-catalyzed Regioselective "ligation" of Azides and Terminal Alkynes" Angewandte Chemie International Edition, 41(14):2596-2599.
Rubinstein and Niv, "Peptidic modulators of protein-protein interactions: Progress and challenges in computational design." Biopolymers (2009); 91(7): 505-513.
Sasaki et al. (1984) "D-Arg2-Dermorphin Tetrapeptide Analogs: A Potent and Long- Lasting Analgesic Activity After Subcutaneous Administration.", Biochemical and Biophysical Research Communications, 120(1):214-218.
Shahidi et al. (2016) "Vedolizumab For The Treatment Of Ulcerative Colitis" Expert Opinion on Biological Therapy, 16(1):129-135.
SID 24885660, National Center for Biotechnology Information, PubChem Substance Database; SID=24885660, https://pubchem.ncbi.nlm.nih.gov/substance/24885660, accessed Jul. 21, 2016, 5 Pages.
Soler-Ferran et al. (2012) "Integrin a417 Antagonists: Activities, Mechanisms of Action and Therapeutic Prospects" Current Immunology Reviews, 8(2): 118-134.
Speers et al. (Mar. 28, 2003) "Activity-Based Protein Profiling in Vivo Using a Copper(I)-Catalyzed Azide-Alkyne [3 + 2] Cycloaddition" Journal of the American Chemical Society, 125(16):4686-4687.
Tandara et al. (Oct. 2012) "Iron metabolism: Current Facts and Future Directions" Biochem Med, 22(3):311-328.
Temming et al. (2006) "Rational Design of RGD-Albumin Conjugates for Targeted Delivery Of The Vegf-R Kinase Inhibitor Ptk787 To Angiogenic Endothelium" ChemMedChem, 1: 1200-1203.
Thermo Electron Corporation (2004) "N-terminal and C-terminal Amidation of Peptides" Technical Information, 2 pages.
Thumshirn et al. (2003) "Multimeric Cyclic RGD Peptides as Potential Tools for Tumor Targeting: Solid Phase Peptide Synthesis and Chemoselective Oxime Liqation" Chemistry—A European Journal, 9:2717-2725.
Tornoe et al. (May 3, 2002) "Peptidotriazoles On Solid Phase: [1,2,3]-Triazoles By Regiospecific Copper(I)-Catalyzed 1,3- Dipolar Cycloadditions of Terminal Alkynes To Azides" The Journal of Organic Chemistry, 67(9):3057-3064.
Tsukada, et al., "An Anti-α-Fetoprotein Antibody-Daunorubicin Conjugate With a Novel Poly-L-glutamic Acid Derivative as Intermediate Drug Carrier ". J. Natl. Cancer Inst. (Sep. 1984); 73(3): 721-729.
Tuvia et al. (Aug. 2014) "A Novel Suspension Formulation Enhances Intestinal Absorption of Macromolecules Via Transient And Reversible Transport Mechanisms" Pharmaceutical Research, 31(8):2010-2021.
Wang et al. (Feb. 2003) "Bioconjugation by Copper(I)-Catalyzed Azide-Alkyne [3 + 2] Cycloaddition" Journal of the American Chemical Society, 125(11):3192-3193.
White and Yudin, "Contemporary strategies for peptide macrocyclization." Nat Chem (Jun. 2011); 3(7): 509-524.
Witt, Dariusz, "Recent developments in disulfide bond formation". Synthesis (2008); 16: 2491- 2509.
Xie et al. (2000) "Nerve Growth Factor (NGF) Loop 4 Dimeric Mimetics Activate ERK and AKT and Promote NGF-like Neurotrophic Effects" The Journal of Biological Chemistry, 275(38): 29868-29874.
Yampolsky et al. (Aug. 2005) "The Exchangeability of Amino Acids in Proteins" Genetics, 170(4): 1459-1472.
Yu et al. (2010) "A Naturally Occurring, Soluble Antagonist of Human IL-23 Inhibits the Development and In Vitro Function of Human Th17 Cells", The Journal of Immunology, 185:7302-7308.
Zalipsky, Samuel, "Functionalized Poly(ethylene glycols) for Preparation of Biologically Relevant Conjugates". Bioconjugate Chem. (1995); 6(2): 150-165.

* cited by examiner

COMPOSITIONS OF PEPTIDE INHIBITORS OF INTERLEUKIN-23 RECEPTOR

CROSS REFERENCE TO RELATED APPLICATIONS

This application claims priority to U.S. Provisional Application Nos. 63/116,568, respectively, filed Nov. 20, 2020 and 63/275,222, filed Nov. 3, 2021, which are incorporated herein in its entirety for all purposes.

SEQUENCE LISTING

This application contains a Sequence Listing which has been submitted electronically in ASCII format and is hereby incorporated by reference in its entirety. The ASCII copy, created on Nov. 9, 2021, is named 056365_518001US_Sequence_Listing_ST25.txt and is 1,202 bytes in size.

FIELD OF THE INVENTION

The present invention relates to peptide inhibitors of the Interleukin-23 Receptor (IL-23R) or pharmaceutically acceptable salt or solvate forms thereof, corresponding pharmaceutical compositions, methods and/or uses for treatment of autoimmune inflammation and related diseases and disorders.

BACKGROUND

The interleukin-23 (IL-23) cytokine has been implicated as playing a crucial role in the pathogenesis of autoimmune inflammation and related diseases and disorders, such as multiple sclerosis, asthma, rheumatoid arthritis, psoriatic arthritis, psoriasis, and inflammatory bowel diseases (IBDs), e.g., ulcerative colitis and Crohn's disease. Studies in acute and chronic mouse models of IBD revealed a primary role of IL-23R and downstream effector cytokines in disease pathogenesis. IL-23R is expressed on various adaptive and innate immune cells, which may include, but are not limited to Th17 cells, γδ T cells, natural killer (NK) cells, dendritic cells, macrophages, and innate lymphoid cells, which are found abundantly in the intestine. At the intestine mucosal surface, the gene expression and protein levels of IL-23R are found to be elevated in IBD patients. It is believed that IL-23 mediates this effect by promoting the development of a pathogenic $CD4^+$ T cell population that responds to IL-6, producing IL22, IL-17, and tumor necrosis factor (TNF).

Production of IL-23 is enriched in the intestine, where it is believed to play a key role in regulating the balance between tolerance and immunity through T-cell-dependent and T-cell-independent pathways of intestinal inflammation through effects on T-helper 1 (Th1) and Th17-associated cytokines, as well as restraining regulatory T-cell responses in the gut, favoring inflammation. In addition, polymorphisms in the IL-23 receptor (IL-23R) have been associated with susceptibility to inflammatory bowel diseases (IBDs), further establishing the critical role of the IL-23 pathway in intestinal homeostasis.

Psoriasis (PsO), a chronic skin disease affecting about 2%-3% of the general population has been shown to be mediated by the body's T cell inflammatory response mechanisms. IL-23 has one of several interleukins implicated as a key player in the pathogenesis of psoriasis, purportedly by maintaining chronic autoimmune inflammation via the induction of interleukin-17, regulation of T memory cells, and activation of macrophages. Expression of IL-23 and IL-23R has been shown to be increased in tissues of patients with psoriasis, and antibodies that neutralize IL-23 showed IL-23-dependent inhibition of psoriasis development in animal models of psoriasis. In addition, IL-23 antibody guselkumab is FDA approved to treat moderate to severe plaque-psoriasis in humans.

IL-23 is a heterodimer composed of a unique p19 subunit and the p40 subunit shared with IL-12, which is a cytokine involved in the development of interferon-γ (IFN-γ)-producing T helper 1 ($T_H1$) cells. Although IL-23 and IL-12 both contain the p40 subunit, they have different phenotypic properties. For example, animals deficient in IL-12 are susceptible to inflammatory autoimmune diseases, whereas IL-23 deficient animals are resistant, presumably due to a reduced number of $CD4^+$ T cells producing IL-6, IL-17, and TNF in the CNS of IL-23-deficient animals. IL-23 binds to IL-23R, which is a heterodimeric receptor composed of IL-12Rβ1 and IL-23R subunits. Binding of IL-23 to IL-23R activates the Jak-stat signaling molecules, Jak2, Tyk2, and Stat 1, Stat 3, Stat 4, and Stat 5, although Stat4 activation is substantially weaker and different DNA-binding Stat complexes form in response to IL-23 as compared with IL-12. IL-23R associates constitutively with Jak2 and in a ligand-dependent manner with Stat3. In contrast to IL-12, which acts mainly on naïve CD4(+) T cells, IL-23 preferentially acts on memory CD4(+) T cells.

Efforts have been made to identify therapeutic moieties that inhibit the IL-23 pathway, for use in treating IL-23-related diseases and disorders. A number of antibodies that bind to IL-23 or IL-23R have been identified, including ustekinumab, an antibody that binds the p40 subunit of IL-23, which has been approved for the treatment of moderate to severe plaque psoriasis, active psoriatic arthritis, moderately to severely active Crohn's disease and moderately to severely active ulcerative colitis. More recently, polypeptide inhibitors that bind to IL-23R and inhibit the binding of IL-23 to IL-23R have been identified (see, e.g., US Patent Application Publication No. US2013/0029907). Clinical trials in Crohn's Disease or psoriasis with briakinumab (i.e., e.g., which also target the common p40 subunit) and tildrakizumab, guselkumab, MEDI2070, and BI-655066 (i.e., e.g., which target the unique p19 subunit of IL-23) highlight the potential of IL-23 signaling blockade in treatment of human inflammatory diseases. While these findings are promising, challenges remain with respect to successful delivery of such therapeutics to their target. Effective delivery can improve the treatment of intestinal inflammation, such as intestinal bowel diseases, including Crohn's disease, ulcerative colitis and related disorders.

There remains a need in the art to develop effective pharmaceutical vehicles, such as pharmaceutical compositions, to deliver therapeutic agents to treat and prevent IL-23 and/or IL-23R associated diseases, especially those associated with autoimmune inflammation, such as in the intestinal tract, which may include, but are not limited to inflammatory bowel disease (IBD), ulcerative colitis, Crohn's Disease (CD), psoriasis, or psoriatic arthritis and the like.

The present invention addresses these needs by providing pharmaceutical compositions of peptide inhibitors or pharmaceutically acceptable salt or solvate forms thereof that:
  bind IL-23R to inhibit IL-23 binding, IL-23 signalling through IL-23 receptor and/or IL-23 Pathway, for treatment of inflammatory diseases or disorders (i.e., e.g., which may include, but is not limited to psoriasis, psoriatic arthritis, inflammatory bowel disease, ulcerative colitis, Crohn's disease and the like), which include, but not limited to aforementioned diseases or disorders that may be moderate to severe in degree and suitable for oral administration.

In addition, pharmaceutical compositions and corresponding methods and/or uses for specific targeting of IL-23R from the luminal side of the gut can provide therapeutic benefit to IBD patients suffering from local inflammation of the intestinal tissue.

The present invention is directed to overcoming these and other problems encountered in the art.

SUMMARY OF THE INVENTION

In general, the present invention relates to peptide inhibitors of the interleukin-23 receptor (IL-23R) or pharmaceutically acceptable salt or solvate forms thereof, corresponding pharmaceutical compositions, methods and/or uses for treatment of autoimmune inflammation and related diseases and disorders, The present invention relates to compositions as described herein, which comprise the peptide of SEQ ID NO: 1:

Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$
(*Pen-Pen form disulfide bond) (SEQ ID NO: 1); or
pharmaceutically acceptable salt or solvate forms thereof, having the structure:

The present invention provides a composition, which comprises: a peptide of SEQ ID NO: 1 or a pharmaceutically acceptable salt or solvate form thereof in an amount of from about 0.1% to about 15% (w/w) of the composition and one or more pharmaceutically acceptable excipients.

The present invention relates to a composition of peptide inhibitors of the interleukin-23 receptor (IL-23R) or pharmaceutically acceptable salt or solvate forms thereof.

The present invention provides a composition, which comprises: a peptide of SEQ ID NO: 1 or a pharmaceutically acceptable salt or solvate form thereof in an amount of from about 0.1% to about 15% (w/w) of the composition; an absorption enhancer in an amount from about 10% to about 60% (w/w); and one or more pharmaceutically acceptable excipients.

The present invention provides a composition, which comprises: an internal phase that includes: a peptide of SEQ ID NO: 1 in an amount of from about 0.1% to about 15% (w/w) of the composition, and sodium caprate in an amount of from about 20% to about 45% (w/w) of the composition; and an external phase disposed over the internal phase, where the external phase comprises a microcrystalline cellulose.

The present invention provides a composition, which comprises: a peptide of SEQ ID NO: 1 or a pharmaceutically acceptable salt or solvate form thereof; and a 50 mM pH 7.4 phosphate buffered aqueous solution.

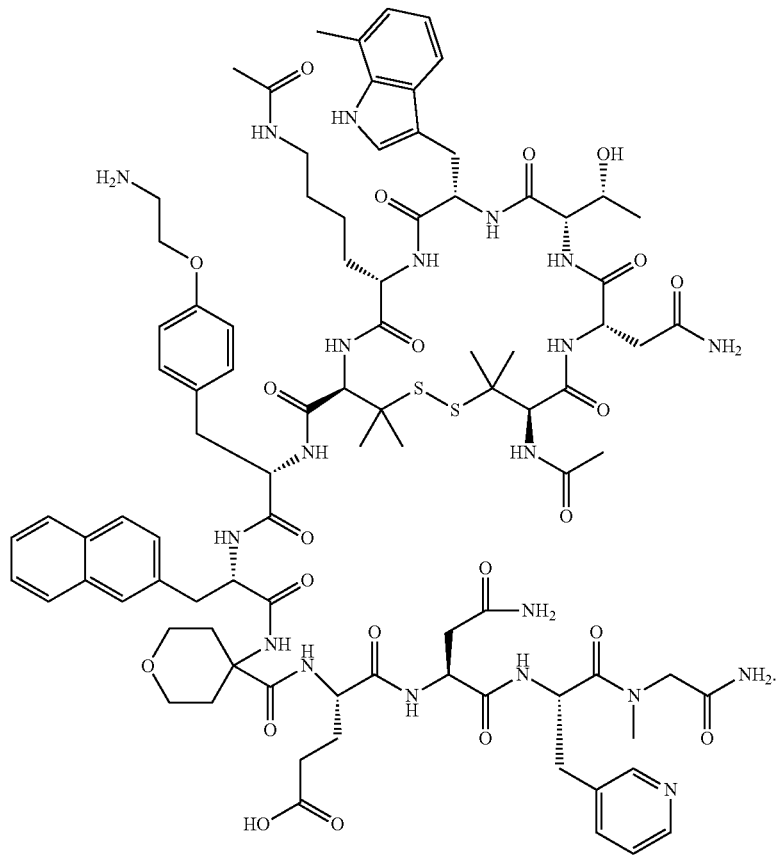 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

The present invention provides a method for making a tablet, which includes steps of:
  granulating a mixture that includes:
    a peptide of SEQ ID NO: 1 or a pharmaceutically acceptable salt or solvate form thereof; and sodium caprate;
  adding to the granulated mixture:
    a microcrystalline cellulose;
    sorbitol;
    a disintegrant; and
    a hydrophilic silica,
  to form an internal phase;
  compressing an external phase over the internal phase; wherein:
    the external phase includes a silicified microcrystalline cellulose;
  applying a subcoating over the external phase; and
  applying an enteric coating over the subcoating to form the tablet.

In some aspects, a method for making a tablet includes the steps of:
  granulating a mixture that includes:
    a peptide of SEQ ID NO: 1; and sodium caprate;
  adding to the granulated mixture:
    a microcrystalline cellulose;
    sorbitol;
    a disintegrant; and
    a hydrophilic silica,
  to form an internal phase;
  compressing an external phase over the internal phase; wherein:
    the external phase includes a silicified microcrystalline cellulose;
  applying a subcoating over the external phase; and
  applying an enteric coating over the subcoating to form the tablet.

The present invention provides a product for treating inflammatory diseases or disorders, wherein the product is prepared by:
  granulating a mixture that includes: a peptide of SEQ ID NO: 1 or a pharmaceutically acceptable salt or solvate form thereof; and sodium caprate;
  adding to the granulated mixture:
    a microcrystalline cellulose;
    sorbitol;
    a disintegrant; and
    a hydrophilic silica, to form an internal phase;
  compressing an external phase over the internal phase, wherein the external phase includes a silicified microcrystalline cellulose;
  applying a subcoating over the external phase; and
  applying an enteric coating over the subcoating to form the product.

The present invention provides a method of treating inflammatory disease, which comprises administering to the subject a therapeutically effective amount of a composition of the present invention to a subject or patient in need thereof as described herein.

The present invention provides a method of treating inflammatory bowel diseases (IBD), which comprises administering a therapeutically effective amount of a composition to a subject or patient in need thereof.

The present invention provides use of the compositions of the present invention in the manufacture of a medicament for treating an inflammatory bowel disease (IBD).

The present invention provides a method of treating psoriasis or psoriatic arthritis in a subject that includes administering to the subject a therapeutically effective amount of a composition described herein.

The present invention provides use of the compositions of the present invention, in the manufacture of a medicament for treating psoriasis or psoriatic arthritis.

The present invention relates to a method for IL-23 receptor inhibition for treating inflammatory diseases or disorders by delivering a systemically active peptide of SEQ ID NO: 1 or a pharmaceutically acceptable salt or solvate form, or a pharmaceutical composition thereof, to a subject or patient in need thereof.

The present invention relates to a method for systemically inhibiting or pharmacologically blocking IL-23 receptor, IL-23 signalling through IL-23 receptor, or IL-23 pathway, for treating inflammatory diseases or disorders by orally administering a therapeutically effective amount of a peptide of SEQ ID NO: 1 or a pharmaceutically acceptable salt or solvate form, or a pharmaceutical composition thereof, to a patient in need thereof.

The present invention relates to a method for inhibition or blocking of IL-23 receptor in blood, blood circulation, tissue, skin or joints for treatment of inflammatory diseases or disorders, which comprises administering an oral dose of a therapeutically effective amount of a peptide of SEQ ID NO: 1 or a pharmaceutically acceptable salt or solvate form, or a pharmaceutical composition thereof, to a patient in need thereof.

The present invention relates to a method for inhibiting IL-23 receptor in a tissue selected from blood, skin, cartilage, or synovial membrane, which comprises administering an oral dose of a therapeutically effective amount of a peptide of SEQ ID NO: 1 or a pharmaceutically acceptable salt or solvate form, or a pharmaceutical composition thereof, to a patient in need thereof.

The present invention relates to a method for inhibiting IL-23 receptor in a digestive tract tissue, which comprises administering an oral dose of a therapeutically effective amount of a peptide of SEQ ID NO: 1, or a pharmaceutically acceptable salt or solvate form thereof to a patient in need thereof.

The present invention relates to a method for inhibiting production of IL-17A in a tissue selected from blood, skin, cartilage, or synovial membrane, which comprises administering an oral dose of a therapeutically effective amount of a peptide of SEQ ID NO: 1 or a pharmaceutically acceptable salt or solvate form thereof to a patient in need thereof.

The present invention relates to a method for inhibiting production of IL-17A in a digestive tract tissue, which comprises administering an oral dose of a therapeutically effective amount of a peptide of SEQ ID NO: 1 or a pharmaceutically acceptable salt or solvate form thereof to a patient in need thereof.

The present invention relates to a method for inhibiting production of IL-17F in a tissue selected from blood, skin, cartilage, or synovial membrane, which comprises administering an oral dose of a therapeutically effective amount of a peptide of SEQ ID NO: 1 or a pharmaceutically acceptable salt or solvate form thereof to a patient in need thereof.

The present invention relates to a method for inhibiting production of IL-17F in a digestive tract tissue, which comprises administering an oral dose of a therapeutically effective amount of a peptide of SEQ ID NO: 1 or a pharmaceutically acceptable salt or solvate form thereof to a patient in need thereof.

The present invention relates to a method for inhibiting production of IL-22 in a tissue selected from blood, skin, cartilage, or synovial membrane, which comprises administering an oral dose of a therapeutically effective amount of a peptide of SEQ ID NO: 1 or a pharmaceutically acceptable salt or solvate form thereof to a patient in need thereof.

The present invention relates to a method for inhibiting production of IL-22 in a digestive tract tissue, which comprises administering an oral dose of a therapeutically effective amount of a peptide of SEQ ID NO: 1 or a pharmaceutically acceptable salt or solvate form thereof to a patient in need thereof.

DETAILED DESCRIPTION OF THE INVENTION

I. General

Figure 1:
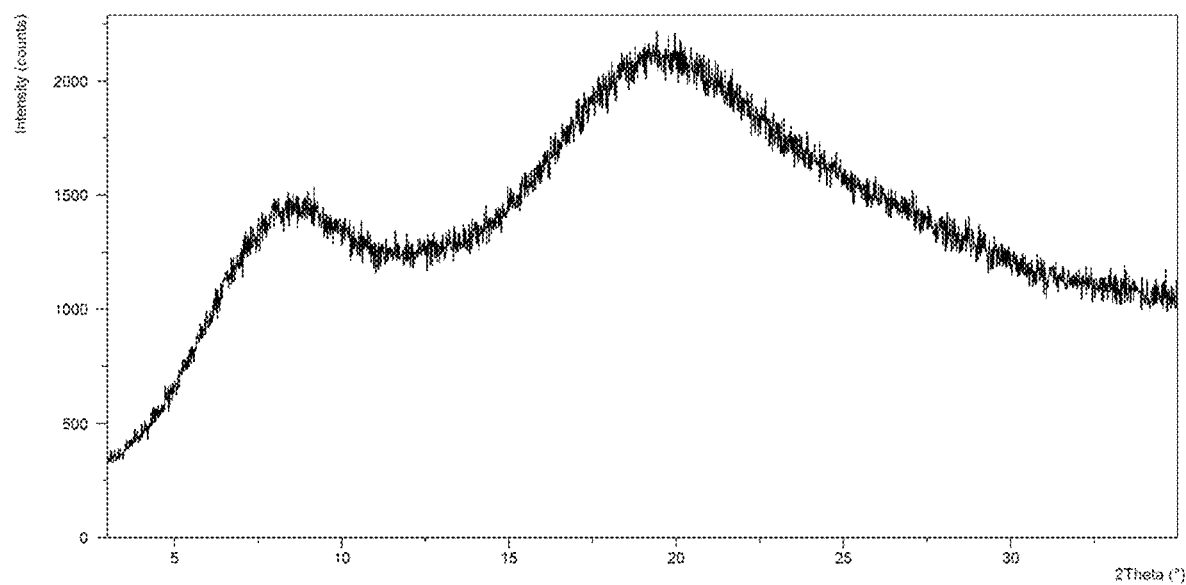
FIG. 1 shows an x-ray powder diffraction spectrum of the peptide of SEQ ID NO:1, as prepared by the procedure of Example 1.
Figure 2:
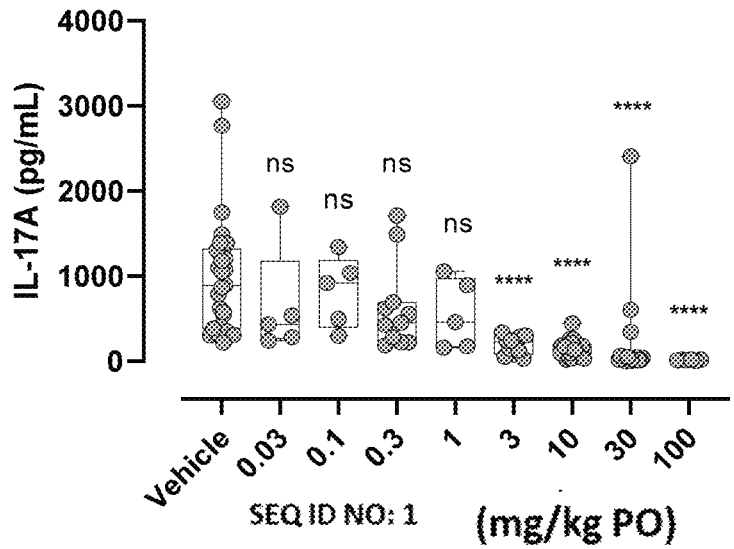
FIG. 2 shows a graph of interleukin-17A levels in rat blood vs. oral doses of the peptide of SEQ ID NO: 1 at (0.03-100 mg/kg, p.o.), following stimulation of the rat blood with 4 ng/mL IL-23 plus 4 ng/mL IL-1β.
Figure 3:
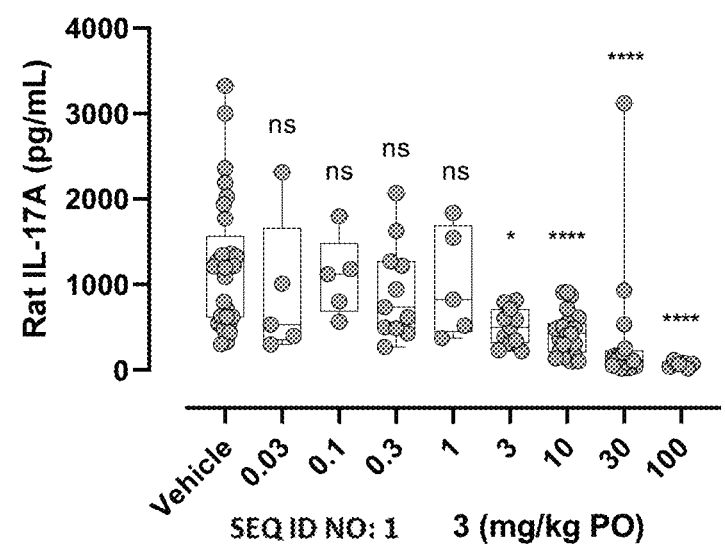
FIG. 3 shows a graph of interleukin-17A levels in rat blood vs. oral doses of the peptide of SEQ ID NO: 1 at (0.03-100 mg/kg, p.o.), following stimulation of the rat blood with 20 ng/mL IL-23 plus 4 ng/mL IL-1β.
Figure 4:
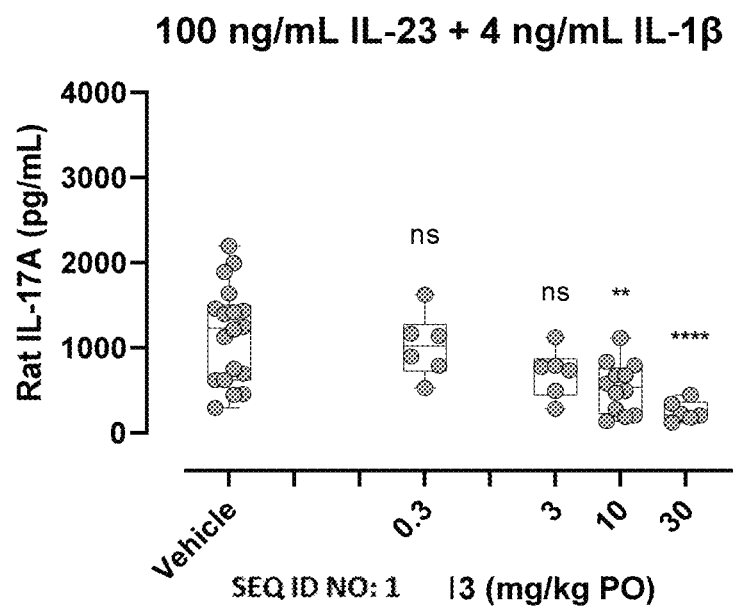
FIG. 4 shows a graph of interleukin-17A levels in rat blood vs. oral doses of the peptide of SEQ ID NO: 1 at (0.03-100 mg/kg, p.o.), following stimulation of the rat blood with 100 ng/mL IL-23 plus 4 ng/mL IL-1β.

In general, the present invention relates to peptide inhibitors of the interleukin-23 receptor (IL-23R) or pharmaceutically acceptable salt or solvate forms thereof, corresponding pharmaceutical compositions, methods and/or uses for treatment of autoimmune inflammation and related diseases and disorders, The present invention relates to pharmaceutical compositions as described herein, which comprise the peptide of SEQ ID NO: 1:

Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1), where the chemical structure is shown below:

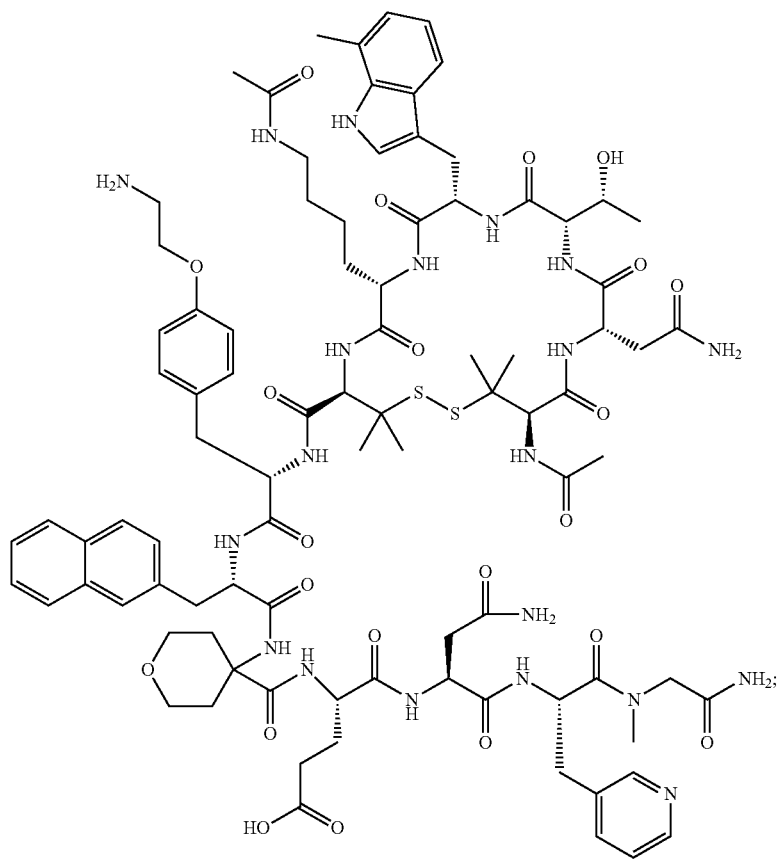 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

35 or a pharmaceutically acceptable salt or solvate form thereof.

The peptide of SEQ ID NO: 1 was previously described as Peptide #104 in PCT publication WO 2021146441 and US 2021/0261622, the disclosures of which are incorporated herein by reference in their entireties.

The present invention relates to pharmaceutical compositions disclosed herein which are suitable for methods or uses for treatment of various autoimmune inflammation and related diseases and disorders, which may include, but are not limited to inflammatory bowel disease (IBD), ulcerative colitis, Crohn's Disease (CD), psoriasis, or psoriatic arthritis and the like.

Each aspect of the present invention defined in this or in any other section may incorporate definitions and limitations, such as those set forth in Sections I to VI of the present application and throughout the originally filed disclosure, specification and claims.

II. Definitions

"A," "an," or "a(n)", is an indefinite article when used in reference to a group of substituents or "substituent group" herein, mean at least one.

"About" when referring to a value includes the stated value +/−10% of the stated value. For example, about 50% includes a range of from 45% to 55%, while about 20 molar equivalents includes a range of from 18 to 22 molar equivalents. Accordingly, when referring to a range, "about" refers to each of the stated values +/−10% of the stated value of each end of the range. For instance, a ratio of from about 1 to about 3 (weight/weight) includes a range of from 0.9 to 3.3. However, in the case of mass units, the term "about" shall mean plus or minus 5 mg. For example, a mass about 10 mg refers to a range of 5 mg to 15 mg, and a mass of about 50 mg refers to a range of 45 mg to 55 mg.

"Absorption enhancer" (AE) refers to a component that improves or facilitates the mucosal absorption of a drug in the gastrointestinal tract, such as a permeation enhancer (PE) or intestinal permeation enhancer. As conventionally understood in the art, permeation enhancers are agents aimed to improve oral delivery of therapeutic drugs with poor bioavailability. PEs are capable of increasing the paracellular and/or transcellular passage of drugs. Pharmaceutical excipients that can increase permeation have been termed 'absorption modifying excipients' (AMEs). AMEs may be used in oral compositions, for example, as wetting agents (sodium dodecyl sulfate), antioxidants (e.g. EDTA), and emulsifiers (e.g. macrogol glycerides), and may be specifically included in compositions as PEs to improve bioavailability. PEs can be categorized as to how they alter barrier integrity via paracellular or transcellular routes. In this disclosure, the term "absorption enhancer" or AE, is considered synonymous with the term "permeation enhancer" or PE.

"Administering" refers to administration of the composition of the present invention to a subject.

"Composition" as used herein is intended to encompass a product that includes the specified active product ingredient (API) and pharmaceutically acceptable excipients, carriers or diluents as described herein, such as in specified amounts defined throughout the originally filed disclosure, which results from combination of specific components, such as specified ingredients in the specified amounts as described herein.

"Digestive tract tissue" as used herein refers to all the tissues that comprise the organs of the alimentary canal. For example only, and without limitation, "digestive tract tissue" includes tissues of the mouth, esophagus, stomach, small intestine, large intestine, duodenum, and anus.

"Disintegrant" refers to a pharmaceutical excipient that is incorporated into a composition to promote their disintegration when they come into contact with a liquid. For example, a disintegrant is a pharmaceutically acceptable agent, used in preparation of tablets, which causes tablets to disintegrate and release medicinal substances on contact with moisture. Examples of disintegrants may include, without limitation, crosslinked polymers, including crosslinked polyvinylpyrrolidone (crospovidone), crosslinked sodium carboxymethyl cellulose (croscarmellose sodium), and modified starch sodium starch glycolate and the like.

"Disposed over" refers to the placement of one phase or coating on top of another phase or coating. Such placement can conform to the shape of the underlying phase or coating such that the layering of phases and coatings do not leave substantial gaps there between.

"Enteric coating" refers to any of the commonly applied polymeric coatings employed for delayed release of active ingredients. As conventionally understood in the art, an enteric coating generally is a polymer barrier applied to oral medication that prevents its dissolution or disintegration in the gastric environment. This helps by either protecting drugs from the acidity of the stomach, the stomach from the detrimental effects of the drug, or to release the drug after the stomach (usually in the upper tract of the intestine). Some drugs are unstable at the pH of gastric acid and need to be protected from degradation. An enteric coating is also an effective method to obtain drug targeting (such as gastro-resistant drugs). Such delayed release is typically pH dependent and allows for release of the active ingredient further in the intestinal tract where the pH differs from that in the stomach. In general, suitable materials used for enteric coatings may include, but is not limited to fatty acids, waxes, shellac, plastics, and plant fibers, where such enteric materials, may include, but is not limited to cellulose acetate phthalate, polyvinylalcohol phthalate, shellac, zein, hydroxypropylmethyl cellulose phthalate, cellulose acetate trimaleate, film resins, etc and the like. Additional examples of enteric coating for use in the present invention, may include, without limitation, those based on esters of aleuritic acid, cellulose acetate phthalate (CAP), poly(methacrylic acid-co-methyl methacrylate), poly(vinyl acetate phthalate) (PVAP), cellulose acetate trimellitate (CAT), hydroxypropyl methylcellulose phthalate (HPMCP) and the like.

"External phase" refers to the bulk portion of a core structure that resides between the internal phase and the outer layer coatings of a composition. While the external phase could itself be considered a coating, it can be generally thicker than a mere coating, thereby imparting significant structure/dimensions to the composition.

"Glidant" refers to a substance that is added to a powder to improve its flowability and/or lubricity. Examples of glidants, may include, but is not limited to, magnesium stearate, fumed silica, starch and talc and the like.

"Granulated mixture" refers to a mixture of two or more agents made by mixing the two or more agents and granulating them together in a particulate form. Such a mixture provides particulate material that is composed of two or more agents. For example in the present invention, the compositions may include, but are not limited to granulated mixtures of the peptide of SEQ ID NO: 1 and sodium caprate. Such a granulated mixture is formed into a particle form containing a peptide of SEQ ID NO: 1 or a pharmaceutically acceptable salt or solvate form thereof and sodium caprate.

"Hydrophilic silica" refers to a pharmaceutical excipient that can be employed as flow agent (anti-caking), adsorbent and desiccant in solid product forms. It can also be used to increase the mechanical stability and the disintegration rate of the compositions. The hydrophilic silica can be fumed, i.e., referring to its production through a pyrogenic process to generate fine particles of silica. Particles of fumed silica can vary in size, which may include but is not limited to sizes such as from 5 nm to 100 nm, or from 5 to 50 nm. The particles can be non-porous and may have, but is not limited to a surface area from 50-1,000 $m^2/g$ or from 50-600 $m^2/g$. Examples of hydrophilic silicas include Aerosil 200, having a specific surface area of about 200 $m^2/g$.

"Internal phase" refers to the central-most portion of a composition. In the present aspects, the internal phase is the location where the active ingredient, the peptide of SEQ ID NO: 1 of the present invention resides or may reside.

"Intestinal permeation enhancer (IPE)" refers to a component that improves the bioavailability of a component having poor bioavailability. Suitable representative IPEs for use in the present invention, include, but are not limited to, various surfactants, fatty acids, medium chain glycerides, steroidal detergents, acyl carnitine and alkanoylcholines, N-acetylated alpha-amino acids and N-acetylated non-alpha-amino acids, and chitosans, other mucoadhesive polymers and the like. For example, a suitable IPE for use in the present invention may be sodium caprate.

"Joint" or "joints" refers to tissues that connect one bone to another in the human body. Examples of tissues encompassed by the term "joint" or joints" include, without limitation, sinews, cartilage, ligaments, and synovial membrane. Synovial fluid adjacent to any of the aforementioned tissues is considered herein to be part of a "joint".

"Lubricant" refers to a substance added to a formulation to reduce friction. Compounds that serve as lubricants can also have properties as glidants. Examples of lubricants may include, but are not limited to, talc, silica, and fats such as vegetable stearin, magnesium stearate or stearic acid and the like.

"Microcrystalline cellulose," or "MCC," refers to a pharmaceutical grade of cellulose manufactured from a refined wood pulp. MCC can be unmodified or chemically modified, such as silicified microcrystalline cellulose (SMCC). MCC can serve the function of a bulking agent and aid in tablet formation due to its favorable compressibility characteristics.

"Patient" or "subject" refers to a living organism, which includes, but is not limited to a human subject suffering from or prone to a disease or condition that can be treated by administration of a pharmaceutical composition as provided herein. Further non-limiting examples may include, but is not limited to humans, other mammals, bovines, rats, mice, dogs, monkeys, and other mammalian animals and the like. In some aspects, the patient is human.

By "pharmaceutically acceptable" it is meant the carrier (s), diluent(s) or excipient(s) must be compatible with the other components or ingredients of the compositions of the present invention, i.e., that which is useful, safe, non-toxic acceptable for pharmaceutical use. In accordance with the present invention pharmaceutically acceptable means approved or approvable as is listed in the U.S. Pharmacopoeia or other generally recognized pharmacopoeia for use in animals, and more particularly, in humans.

Compositions or pharmaceutical compositions of the present invention may be in different pharmaceutically acceptable forms, including, but are not limited to a liquid composition, a tablet or matrix composition, a capsule composition, etc. and the like.

When the composition is a tablet composition, the tablet can include two or more different phases, including an internal phase and an external phase that can comprise a core. The tablet composition can also include, but is not limited to one or more coatings.

"Silicified microcrystalline cellulose," or "SMCC," refers to a particulate agglomerate of coprocessed microcrystalline cellulose and silicon dioxide. Suitable for use in the present invention, SMCC may include, but is not limited to amounts from about 0.1% to about 20% silicon dioxide, by weight of the microcrystalline cellulose, where the silicon dioxide can have a particle size from about 1 nanometer (nm) to about 100 microns (μm), based on average primary particle size. For example, the silicon dioxide can contain from about 0.5% to about 10% of the silicified microcrystalline cellulose, or from about 1.25% to about 5% by weight relative to the microcrystalline cellulose. Moreover, the silicon dioxide can have a particle size from about 5 nm to about 40 μm, or from about 5 nm to about 50 μm. The silicon dioxide can have a surface area from about 10 m$^2$/g to about 500 m$^2$/g, or from about 50 m$^2$/g to about 500 m$^2$/g, or from about 175 m$^2$/g to about 350 m$^2$/g. Silicified microcrystalline cellulose is commercially available from a number of suppliers known to one of skill in the art, including Penwest Pharmaceuticals, Inc., under the trademark PROSOLV®. PROSOLV® is available in a number of grades, including, for example, PROSOLV® SMCC 50, PROSOLV® SMCC 90, and PROSOLV® HD. Other products include, without limitation, SMCC SOLD, SMCC HD90 and SMCC 90LM and the like.

"Sodium caprate" or "NaCl0" refers to the IUPAC compound sodium decanoate having molecular formula $C_{10}H_{19}NaO_2$ and the structural formula:

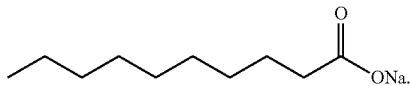

"Solvate" as used herein, means a physical association of the compounds of the present invention with one or more solvent molecules. This physical association involves varying degrees bonding, including hydrogen bonding. In certain instances, the solvate will be capable of isolation. The term "solvate" is intended to encompass both solution-phase and isolatable solvates. Non-limiting examples of suitable solvates include hydrates.

"Sorbitol" refers to the sugar alcohol D-glucitol and which may serve as a binder promoting adhesion of ingredients in tablet compositions.

"Subcoating" refers to any number of film layers disposed over the external phase that can provide one or more benefits such as, providing a smooth tablet surface to ease swallowing of compositions, accommodate pigmentation to aid in pill identification, provide a moisture barrier, and provide a high tensile strength outer layer of the tablet. Such subcoatings can comprise, but is not limited to graft co-polymers of polyvinyl alcohol (PVA) and polyethylene glycol (PEG). Commercial products that provide subcoatings include the line of products under the trade names OPADRY®, OPA-GLOS®, and the like. A subcoating may be further covered by one or more additional coatings.

"Therapeutically effective amount" refers to an amount of a compound or of a pharmaceutical composition useful for treating or ameliorating an identified disease or condition, or for exhibiting a detectable therapeutic or inhibitory effect. "Therapeutically effective amount" further includes within its meaning a non-toxic but sufficient amount of the particular drug to which it is referring to provide the desired therapeutic effect. The exact amount required will vary from subject to subject depending on factors such as the patient's general health, the patient's age, etc. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

The abbreviation, "(w/w)" refers to the phrase "weight for weight" or "weight by weight", i.e., the proportion of a particular substance within a mixture, as measured by weight or mass or a weight amount of a component of the composition disclosed herein relative to the total weight amount of the composition. Accordingly, the quantity is unit less or unitless and represents a weight percentage amount of a component relative to the total weight of the composition. For example, a 2% (w/w) solution means 2 grams of solute is dissolved in 100 grams of solution.

Systemic routes of administration as conventionally understood in the medicinal or pharmaceutical arts, refer to or are defined as a route of administration of drug, a pharmaceutical composition or formulation, or other substance into the circulatory system so that various body tissues and organs are exposed to the drug, formulation or other substance. As conventionally understood in the art, administration can take place orally (where drug or oral preparations are taken by mouth, and absorbed via the gastrointestinal tract), via enteral administration (absorption of the drug also occurs through the gastrointestinal tract) or parenteral administration (generally injection, infusion, or implantation, etc.

"Systemically active" peptide drug therapy as it relates to the present invention generally refers to treatment by means of a pharmaceutical composition comprising a peptide active ingredient, wherein said peptide resists immediate metabolism and/or excretion resulting in its exposure in various body tissues and organs, such as the cardiovascular, respiratory, gastrointestinal, nervous or immune systems.

Systemic drug activity in the present invention also refers to treatment using substances that travel through the bloodstream, reaching and affecting cells in various body tissues and organs. Systemic active drugs are transported to their site of action and work throughout the body to attack the physiological processes that cause inflammatory diseases.

Bioavailability refers to the extent and rate at which the active moiety (drug or metabolite) enters systemic circulation, thereby accessing the site of action. Bioavailability of a drug is impacted by the properties of the dosage form, which depend partly on its design and manufacture.

III. Pharmaceutical Compositions

In general, the present invention relates to compositions of peptide inhibitors of the interleukin-23 receptor (IL-23R) or pharmaceutically acceptable salt or solvate forms thereof, corresponding pharmaceutical compositions, methods and/or uses for treatment of autoimmune inflammation and related diseases and disorders as defined herein.

In one aspect, the present invention provides a composition of the peptide of SEQ ID NO: 1 or pharmaceutically acceptable salt or solvate form thereof.

In another aspect, the composition of the present invention relates to a peptide of SEQ ID NO: 1, which is defined as:
Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ in which *Pen-Pen* form disulfide bond, and having the following chemical structure shown below:

acceptable salt, hydrate, or other solvate. In some aspects, the peptide of SEQ ID NO: 1 or a pharmaceutically acceptable salt or solvate form thereof may be provided in crystalline form, in an amorphous form, or a semi-crystalline form.

In one aspect of the composition, the peptide of SEQ ID NO: 1 or a pharmaceutically acceptable salt or solvate form thereof is the salt form. In one aspect of the composition, the peptide of SEQ ID NO: 1 or a pharmaceutically acceptable salt or solvate form thereof is an acetate salt. In another aspect of the composition, the peptide of SEQ ID NO: 1 or a pharmaceutically acceptable salt or solvate form thereof is a bis-acetate salt. In another aspect of the composition, the acetate form of the peptide of SEQ ID NO: 1 or a pharmaceutically acceptable salt or solvate form thereof is in an amorphous form. In another aspect of the composition, the acetate form of the peptide of SEQ ID NO: 1 or a pharmaceutically acceptable salt or solvate form thereof is the acetate salt. In another aspect of the composition, the acetate form of the peptide of SEQ ID NO: 1 or a pharmaceutically acceptable salt or solvate form thereof is the bis-acetate salt. In yet another aspect, the acetate salt of the composition of the present invention is in the amorphous form. In another aspect of the composition, the peptide of SEQ ID NO: 1 or a pharmaceutically acceptable salt or solvate form thereof is

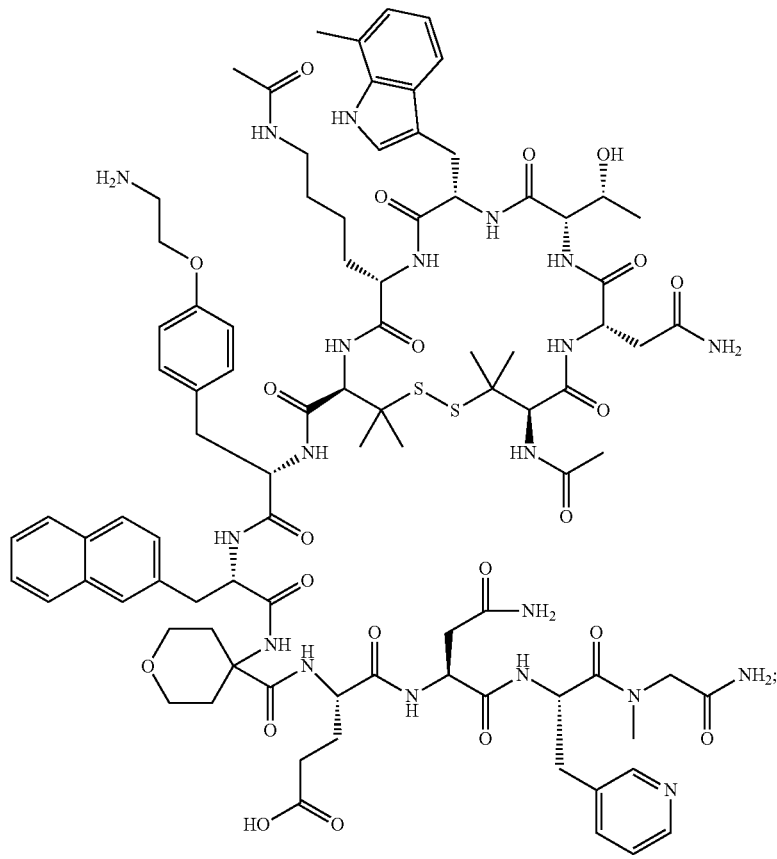 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

or a pharmaceutically acceptable salt or solvate form thereof.

In another aspect, the peptide of SEQ ID NO: 1 or a pharmaceutically acceptable salt or solvate form thereof may be present in any form, such as a pharmaceutically the solvate form. In another aspect of the composition, the acetate form of the peptide of SEQ ID NO: 1 is the acetate solvate.

The present invention relates to compositions which may be in a liquid or a solid composition.

The compositions of the present invention can be administered to a subject or patient by any means in accordance with therapeutic administration, which accomplishes intended purpose or pharmaceutical efficacy. Examples include administration by oral, parenteral, subcutaneous, intravenous, intramuscular, intraperitoneal, transdermal, topical, buccal or ocular routes. In some aspects, the administration of the composition of the present invention is adapted for oral administration. In some other aspects, the administration of the composition is intravenous administration.

In another aspect, the present invention provides a composition which comprises a peptide of SEQ ID NO: 1 or a pharmaceutically acceptable salt or solvate form thereof in an amount of from about 0.1% to about 15% (w/w) of the composition and one or more pharmaceutically acceptable excipients.

In another aspect, the present invention provides a composition which comprises a peptide of SEQ ID NO: 1 or a pharmaceutically acceptable salt or solvate form thereof in an amount of from about 0.1% to about 20% (w/w) of the composition and one or more pharmaceutically acceptable excipients.

In another aspect, the peptide of SEQ ID NO: 1 or a pharmaceutically acceptable salt or solvate form thereof has the structure:

In another aspect, the peptide of SEQ ID NO: 1 has the structure:

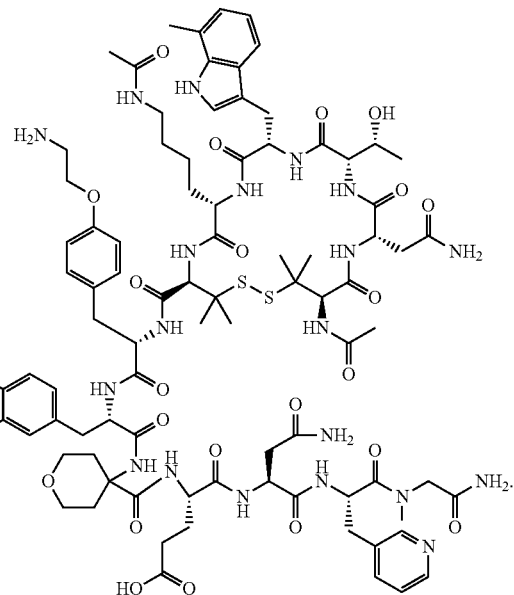

In another aspect, the present invention provides a composition, which comprises: a peptide of SEQ ID NO: 1 or a pharmaceutically acceptable salt or solvate form thereof; and a 50 mM pH 7.4 phosphate buffered aqueous solution.

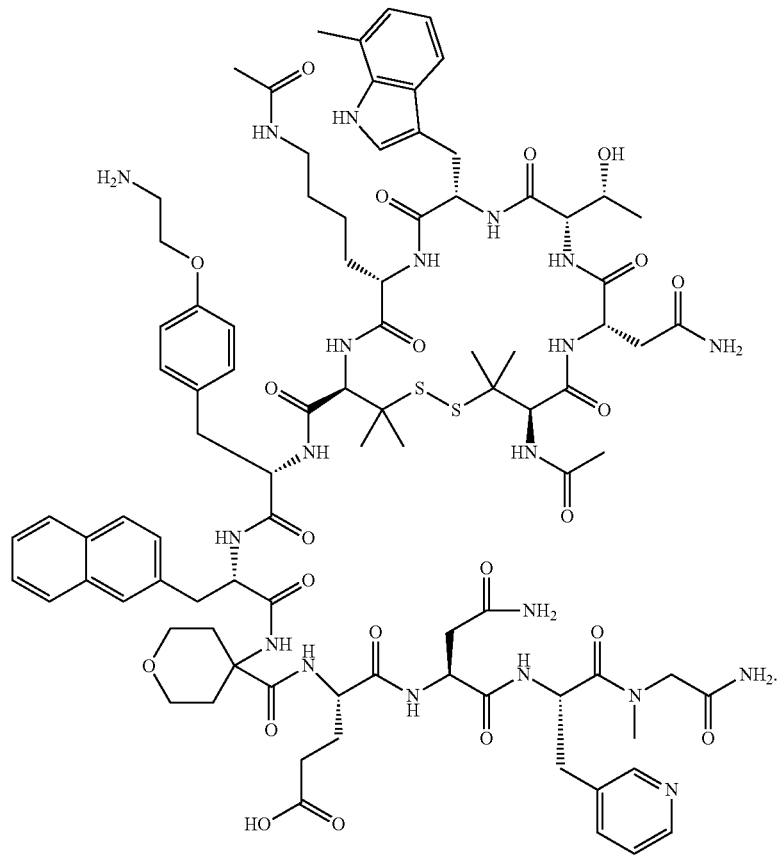 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

In another aspect, the present invention provides a composition, which comprises: a peptide of SEQ ID NO: 1; and a 50 mM pH 7.4 phosphate buffered aqueous solution.

In another aspect, the peptide of SEQ ID NO: 1, or a pharmaceutically acceptable salt or solvate form thereof, may be present in any amount from about 0.1% to about 15% (w/w) of the composition. For example, the peptide of SEQ ID NO: 1, or a pharmaceutically acceptable salt or solvate form thereof, may be present in an amount of from about 0.5% to about 15% (w/w), or from about 1% to about 10%, or from about 0.5% to about 5%, or from about 0.5% to about 3%, or from about 1% to about 3%, or from about 1.5% to about 2.5%, or from about 1.5% to about 2.0% (w/w) of the composition. In another aspect, the peptide of SEQ ID NO: 1 or a pharmaceutically acceptable salt or solvate form thereof may be present in an amount of from about 1% to about 5% (w/w). In another aspect, the peptide of SEQ ID NO: 1 or a pharmaceutically acceptable salt or solvate form thereof may be present in an amount of about 1.8% (w/w). In another aspect, the peptide of SEQ ID NO: 1 or a pharmaceutically acceptable salt or solvate form thereof may be present in an amount of about 7.1% (w/w). In another aspect, the peptide of SEQ ID NO: 1 or a pharmaceutically acceptable salt or solvate form thereof may be present in an amount of about 10.7% (w/w).

In another aspect, the peptide of SEQ ID NO: 1 may be present in any amount from 0.1 to 15% (w/w) of the composition. For example, the peptide of SEQ ID NO: 1 may be present in an amount of from 0.5 to 15% (w/w), or from 1 to 10%, or from 0.5 to 5%, or from 0.5 to 3%, or from 1 to 3%, or from 1.5 to 2.5%, or from 1.5 to 2.0% (w/w) of the composition. In another aspect, the peptide of SEQ ID NO: 1 may be present in an amount of from 1 to 5% (w/w). For example, the peptide of SEQ ID NO: 1 may be present in amounts including about 1%, 2%, 3%, 4%, 5%, 6%, 7%, 8%, 9%, 10%, 11%, 12%, 13%, 14% or about 15% (w/w) of the composition, and any fractional amount in between. In another aspect, the peptide of SEQ ID NO: 1 may be present in an amount of about 1.8% (w/w).

In another aspect, the peptide of SEQ ID NO: 1 or a pharmaceutically acceptable salt or solvate form thereof may be present in any absolute amount. For example, the peptide of SEQ ID NO: 1 or a pharmaceutically acceptable salt or solvate form thereof may be present in an amount of from 1 mg to 1000 mg, or from 1 to 500 mg, or from 1 to 100 mg, or from 10 to 50 mg, or from 20 to 30 mg. In another aspect, the peptide of SEQ ID NO: 1 or a pharmaceutically acceptable salt or solvate form thereof may be present in an amount of from 10 mg to 50 mg. In another aspect, the peptide of SEQ ID NO: 1 or a pharmaceutically acceptable salt or solvate form thereof may be present in an amount of from 20 to 40 mg. In another aspect, the peptide of SEQ ID NO: 1 or a pharmaceutically acceptable salt or solvate form thereof may be present in an amount of from 20 to 30 mg. In yet another aspect, the peptide of SEQ ID NO: 1 or a pharmaceutically acceptable salt or solvate form thereof may be present in an amount of about 10 mg, 15 mg, 20 mg, 25 mg, 30 mg, 35 mg, 40 mg, 45 mg, or 50 mg, 100 mg, 300 mg, or 1000 mg, including any amount in between and fractions thereof. In another aspect, the peptide of SEQ ID NO: 1 or a pharmaceutically acceptable salt or solvate form thereof may be present in an amount of about 25 mg.

In some aspects, the peptide of SEQ ID NO: 1 or a pharmaceutically acceptable salt or solvate form thereof may be present in an amount of from about 1 mg to about 1000 mg, or from about 1 to about 500 mg, or from about 1 to about 100 mg, or from about 10 to about 50 mg, or from about 20 to about 30 mg. In another aspect, the amount of the peptide of SEQ ID NO: 1 or a pharmaceutically acceptable salt or solvate form thereof may be from about 1 mg to about 1000 mg. In another aspect, the amount of the peptide of SEQ ID NO: 1 or a pharmaceutically acceptable salt or solvate form thereof may be from about 10 mg to about 300 mg. In another aspect, the amount of the peptide of SEQ ID NO: 1 or a pharmaceutically acceptable salt or solvate form thereof is from about 25 mg to about 150 mg. In another aspect, the amount of the peptide of SEQ ID NO: 1 or a pharmaceutically acceptable salt or solvate form thereof may be from about 25 mg to about 100 mg. In another aspect, the amount of the peptide of SEQ ID NO: 1 or a pharmaceutically acceptable salt or solvate form thereof may be about 25 mg. In some aspects, the amount of the peptide of SEQ ID NO: 1 or a pharmaceutically acceptable salt or solvate form thereof is about 100 mg. In another aspect, the amount of the peptide of SEQ ID NO: 1 or a pharmaceutically acceptable salt or solvate form thereof may be about 150 mg.

In general, pharmaceutical compositions of the present invention may be formed into different dosage forms prepared using conventional materials and techniques known in the pharmaceutical and formulary arts, which may include, but is not limited to techniques, such as mixing, blending and the like and as set forth throughout the instant disclosure. Moreover, pharmaceutical composition used to form dosage forms may also include, but are not limited to, suitable adjuvants, carriers, excipients, or stabilizers, etc. and can be in solid or liquid form such as, solid or liquid dosage forms, which may include, but are not limited to tablets, capsules, powders, solutions, suspensions, or emulsions and the like, etc. In accordance with the present invention, solid unit dosage forms may be other conventional types known in the art.

Further, suitable for use in the present invention are solutions, which may, but are not limited to, such as in water, saline, aqueous dextrose and related sugar solutions, and glycols such as, propylene glycol or polyethylene glycol, buffered solutions and the like, etc., are preferred liquid carriers, particularly for injectable solutions. Under ordinary conditions of storage and use, these preparations contain a preservative to prevent the growth of microorganisms.

The compositions of the present invention may include a variety of other pharmaceutically acceptable components or excipients, such as, including, but not limited to, a glidant, a lubricant, a disintegrant, a binder, a desiccant, a filler, and other components or excipients and the like. These components are described within.

In accordance with the present invention, compositions as described herein may include at least one filler in any amount adapted for use in the present invention. In some aspects, a composition of the present invention may comprise, but is not limited to one or more of alpha cellulose, beta cellulose, gamma cellulose, starch, modified-starch, sorbitol, mannitol, lactose, dextrose, sucrose, dibasic calcium phosphate, tribasic calcium phosphate, or calcium carbonate and the like.

Representative fillers for use in the compositions of the present invention may include, but are not limited to, starch, lactitol, lactose, an inorganic calcium salt, microcrystalline cellulose, sucrose, combinations thereof and the like. Additional fillers or diluents for use in the compositions of the present invention, may include, but are not limited to fillers or diluents conventionally known in the art, i.e., which are typically used in formulation of pharmaceutical compounds. Examples of such fillers or diluents for use in accordance with the present invention may include, but are not limited to sugars such as lactose, dextrose, glucose, sucrose, cellulose, starches and carbohydrate derivatives, polysaccharides (including dextrates and maltodextrin), polyols (including mannitol, xylitol, and sorbitol), cyclodextrins, calcium carbonates, magnesium carbonates, microcrystalline cellulose, combinations thereof, and the like. In some aspects, such fillers or diluents suitable for use in the present invention may include, but are not limited to lactose, microcrystalline cellulose, combinations thereof and the like. Several types of microcrystalline cellulose may be suitable for use in compositions described herein, for example, microcrystalline cellulose may be selected from, but is not limited to MICROCEL® or AVICEL® types: PH101, PH102, PH103, PH105, PH 112, PH113, PH200, PH301, and the like and other types of microcrystalline cellulose, such as silicified microcrystalline cellulose. In one aspect, a filler suitable for use in the present invention may include microcrystalline cellulose (AVICEL PH102). In another aspect, a filler suitable for use in the present invention may include microcrystalline cellulose (AVICEL PH101).

In some aspects, a filler for use in the present invention may be present in an amount of from about 1% to about 99% (w/w) of the composition, or from about 1% to about 50%, or from about 1% to about 25%, or from about 1% to about 20%, or from about 1% to about 10%, or from 2% to about 8%, or from about 3% to about 5% (w/w) of a composition described herein.

Moreover, in another aspect, a filler for use in the present invention may be present in an amount of from 1 to 99% (w/w) of the composition, or from 1 to 50%, or from 1 to 25%, or from 1 to 20%, or from 1 to 10%, or from 2 to 8%, or from 3 to 5% (w/w) of a composition as defined in the instant specification. Moreover, such a filler may also be present in an amount of about 1% (w/w), 2%, 3%, 4%, 5%, 6%, 7%, 8%, 9%, or about 10% (w/w) of the composition, which may include, but is not limited to any fractional amount in between those as defined.

In some aspects, the composition further can include microcrystalline cellulose. In some aspects, the composition further can include, but is not limited to a silicified microcrystalline cellulose. In some aspects, the composition further can include one or more of alpha cellulose, beta cellulose, gamma cellulose, starch, modified-starch, sorbitol, mannitol, lactose, dextrose, sucrose, dibasic calcium phosphate, tribasic calcium phosphate, or calcium carbonate and the like. In some aspects, the composition further can include mannitol. In some aspects, the composition further can include sorbitol.

In some aspects, the microcrystalline cellulose can be in an amount of about 1% to about 25% (w/w) of the composition. In some aspects, the microcrystalline cellulose can be present in the internal phase of the composition in an amount of about 1% to about 25% (w/w) of the composition. In some aspects, the microcrystalline cellulose can be present in the internal phase of the composition in an amount of about 1% to about 10% (w/w) of the composition. In some aspects, the microcrystalline cellulose can be present in the internal phase of the composition in an amount of about 21.3% (w/w) of the composition. In some aspects, the microcrystalline cellulose can be present in the internal phase of the composition in an amount of about 3.9% (w/w) of the composition.

In some aspects, the composition can further comprise a silicified microcrystalline cellulose. In some aspects, the silicified microcrystalline cellulose may be, but is not limited to SMCC 50, SMCC SOLD, SMCC 90, SMCC HD90 or SMCC 90LM and the like. In some aspects, silicified microcrystalline cellulose may be, but is not limited to SMCC 50, SMCC SOLD, SMCC 90, SMCC HD90 or SMCC 90LM. Without being bound by theory, the silicified microcrystalline cellulose is believed to protect an enteric coating from premature erosion by sodium caprate present in the internal phase. The silicified microcrystalline cellulose may be present in any suitable amount for use in the present invention. For example, the SMCC can be present in an amount of from about 1 to about 99% (w/w) of the composition, or from about 10 to about 50%, or from about 25 to about 60%, or from about 20 to about 50%, or from about 25 to about 45%, or from about 30 to about 40%, or from about 35 to about 37% (w/w) of the composition. The SMCC can be present in an amount of about 30% (w/w) of the composition, or above 31%, 32%, 33%, 34%, 35%, 36%, 36.1%, 36.2%, 36.3%, 36.4%, 36.5%, 36.6%, 36.7%, 36.8%, 36.9%, 37%, 38%, 39%, or about 40% (w/w) of the composition. In some aspects, the silicified microcrystalline cellulose can be in an amount of from about 25 to about 60% (w/w) of the composition.

The composition can also include a binder. Binders for use in the compositions of the present invention include binders commonly used in the formulation of pharmaceuticals. Examples of binders for use in the present invention may include but are not limited to cellulose derivatives (including hydroxypropyl cellulose, hydroxypropyl methylcellulose, methylcellulose, and sodium carboxymethyl cellulose), glycol, sucrose, dextrose, corn syrup, polysaccharides (including acacia, tragacanth, guar, alginates and starch), corn starch, pregelatinized starch, modified corn starch, gelatin, polyvinylpyrrolidone, polyethylene, polyethylene glycol, combinations thereof and the like.

In some aspects, a composition of the present invention may include sorbitol. For example, for use in the present invention, sorbitol may be present in an amount of from about 1% to about 99% (w/w) of the composition, or from about 1% to about 50%, or from about 1% to about 25%, or from about 5% to about 25%, or from about 5% to about 20%, or from about 5% to about 15%, or from about 8% to about 12% (w/w) of the composition. In some aspects, the composition also includes sorbitol in an amount of from about 5% to about 15% (w/w) of the composition.

In some aspects, for use in the present invention, sorbitol may be present in an amount of from 1 to 99% (w/w) of the composition, or from 1 to 50%, or from 1 to 25%, or from 5 to 25%, or from 5 to 20%, or from 5 to 15%, or from 8 to 12% (w/w) of the composition. In another aspect, sorbitol can be present in an amount of about 5% (w/w) of the composition, or 6%, 7%, 8%, 9%, 10%, 10.1%, 10.2%, 10.3%, 10.4%, 10.5%, 10.6%, 10.7%, 10.8%, 10.9%, 11%, 12%, 13%, 14%, or about 15% (w/w) of the composition. In some aspects, the composition also includes sorbitol in an amount of from 5% to 15% (w/w) of the composition. In some aspects, the composition also includes sorbitol in an amount of about 10.7% (w/w) of the composition.

In some aspects, glidant may include, but is not limited to magnesium stearate. The glidant can be present in an amount of from 0.1% to 10% (w/w) of the composition, or from 0.1% to 5%, or from 0.1% to 1%, or from 0.1% to 0.5% (w/w) of the composition. In some aspects, the glidant can be present in an amount of from 0.1% to 0.5% (w/w) of the composition. The glidant can also be present in an amount of about 0.10% (w/w) of the composition, or 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, or about 0.30% (w/w) of the composition. In some aspects, the glidant may be present in an amount of about 0.25% (w/w). In some aspects, the glidant may be present in an amount of about 0.5% (w/w). In some aspects, the glidant is magnesium stearate in an amount of about 0.25% (w/w).

In other aspects, when the composition is a tablet composition, the compositions can include, but is not limited to a two phase structure in which an external phase includes a microcrystalline cellulose, and an internal phase includes the peptide of SEQ ID NO: 1 or a pharmaceutically acceptable salt or solvate form thereof.

In some aspects, compositions of the present invention may not include or may exclude use of an absorption enhancer depending on the intended delivery or use thereof and/or for treatment of specific indications as defined in the present invention.

In other aspects, suitable compositions of the present invention may exhibit improved bioavailability when administered in conjunction with an absorption enhancer, such as an intestinal permeation enhancer.

In some aspects, compositions of the present invention may include an absorption or permeation enhancer. When present, the absorption or permeation enhancer may be, but not limited to the following forms: zwitterionic, cationic, anionic or non-ionic. In one aspect, the absorption or permeation enhancer is an intestinal permeation or absorption enhancer. In some aspects, the absorption enhancer may be selected from, but is not limited to medium-chain saturated fatty acids, such as a caprate, a caprylate, a myristate, a palmitate, or a stearate, including salt forms, such as sodium caprate, sodium caprylate, sodium myristate, sodium palmitate, or sodium stearate) and the like.

Other absorption or permeation enhancer(s) may include, but is/are not limited to a citric acid or citrate salt, such as sodium citrate, tartaric acid or tartrate salt, a salicylic acid or a derivative thereof, or a salicylate salt, a fatty acid acylated amino acid, an alkylsaccharide, a C8-o alkylpolysaccharide, n-octyl-beta-D-glucopyranoside, n-dodecyl-beta-D-maltoside, n-tetradecyl-beta-D-maltoside, tridecylbeta-D-maltoside, sucrose laurate, sucrose myristate, sucrose palmitate, sucrose cocoate, sucrose mono-dodecanoate, sucrose monotridecanoate, sucrose monotetradecanoate, a coco-glucoside, a cyclodextrins, alkanoyl carnitine such as lauroyl carnitine, myristoyl carnitine or palmitoyl carnitine, lauroyl carnitine chloride, myristoyl carnitine chloride or palmitoyl carnitine chloride, fatty acid acylated amino acids, including, without limitation, sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methioninate, N-dodecanoyl-L-methionine, sodium lauroyl phenylalaninate, N-dodecanoyl-L-phenylalanine, sodium lauroyl propionate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophan, sodium lauroyl tyrosinate, N-dodecanoyl-L-tyrosine, sodium lauroyl valinate, N-dodecanoyl-L-valine, sodium lauroyl sarcosinate, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-L-isoleucine, sodium capric leucinate, N-decanoyl-L-leucine, sodium capric methioninate, N-decanoyl-L-methionine, sodium capric phenylalaninate, N-decanoyl-L-phenylalanine, sodium capric propionate, N-decanoyl-L-proline, sodium capric serinate, N-decanoyl-L-serine, sodium capric threoninate, N-decanoyl-L-threonine, sodium capric tryptophanate, N-decanoyl-L-tryptophan, sodium capric tyrosinate, N-decanoyl-L-tyrosine, sodium capric valinate, N-decanoyl-L-valine, sodium capric sarcosinate, N-decanoyl-L-sarcosine, sodium oleoyl sarcosinate, sodium N-decylleucine, sodium stearoyl glutamate (e.g., Amisoft HS-1 1 P), sodium myristoyl glutamate (e.g., Amisoft MS-1 1), sodium lauroyl glutamate (e.g., Amisoft LS-1 1), sodium cocoyl glutamate (e.g., Amisoft CS-1 1), sodium cocoyl glycinate (e.g., Am lite GCS-1 1), sodium N-decyl leucine, sodium cocoyl glycine, sodium cocoyl glutamate, sodium lauroyl alaninate, N-dodecanoyl-L-alanine, sodium lauroyl asparaginate, N-dodecanoyl-L-asparagine, sodium lauroyl aspartic acid, N-dodecanoyl-L-aspartic acid, sodium lauroyl cysteinate, N-dodecanoyl-L-cysteine, sodium lauroyl glutamic acid, N-dodecanoyl-L-glutamic acid, sodium lauroyl glutaminate, N-dodecanoyl-L-glutamine, sodium lauroyl glycinate, N-dodecanoyl-L-glycine, sodium lauroyl histidinate, N-dodecanoyl-L-histidine, sodium lauroyl isoleucinate, N-dodecanoyl-L-isoleucine, sodium lauroyl leucinate, N-dodecanoyl-L-leucine, sodium lauroyl methioninate, N-dodecanoyl-L-methionine, sodium lauroyl phenylalaninate, N-dodecanoyl-L-phenylalanine, sodium lauroyl propionate, N-dodecanoyl-L-proline, sodium lauroyl serinate, N-dodecanoyl-L-serine, sodium lauroyl threoninate, N-dodecanoyl-L-threonine, sodium lauroyl tryptophanate, N-dodecanoyl-L-tryptophan, sodium lauroyl tyrosinate, N-dodecanoyl-L-tyrosine, sodium lauroyl valinate, N-dodecanoyl-L-valine, N-dodecanoyl-L-sarcosine, sodium capric alaninate, N-decanoyl-L-alanine, sodium capric asparaginate, N-decanoyl-L-asparagine, sodium capric aspartic acid, N-decanoyl-L-aspartic acid, sodium capric cysteinate, N-decanoyl-L-cysteine, sodium capric glutamic acid, N-decanoyl-L-glutamic acid, sodium capric glutaminate, N-decanoyl-L-glutamine, sodium capric glycinate, N-decanoyl-L-glycine, sodium capric histidinate, N-decanoyl-L-histidine, sodium capric isoleucinate, N-decanoyl-Lisoleucine, sodium capric leucinate, N-decanoyl-L-leucine, sodium capric methioninate, N-decanoyl-L-methionine, sodium capric phenylalaninate, N-decanoyl-L-phenylalanine, sodium capric prolinate, N-decanoyl-L-proline, sodium capric serinate, N-decanoyl-L-serine, sodium capric threoninate, N-decanoyl-L-threonine, sodium capric tryptophanate, N-decanoyl-Ltryptophan, sodium capric tyrosinate, N-decanoyl-L-tyrosine, sodium capric valinate, N-decanoyl-L-valine, sodium capric sarcosinate, sodium oleoyl sarcosinate, and pharmaceutically acceptable salts of any of the aforementioned compounds; or an alkanoyl sarcosinate (e.g., a lauroyl sarcosinate, such as sodium lauroyl sarcosinate) or one of the 20 standard proteinogenic alpha-amino acids that is acylated with a $C_8$-$C_{20}$ alkanoic acid), an alkylsaccharide (e.g., a $C_1$-$C_{20}$ alkylsaccharide, such as, Multitrope™ 1620-LQ-(MV); or, n-octyl-beta-D-glucopyranoside, n-dodecyl-beta-D-maltoside, n-tetradecyl-beta-D-maltoside, tridecyl-beta-D-maltoside, sucrose laurate, sucrose myristate, sucrose palmitate, sucrose cocoate, sucrose mono-dodecanoate, sucrose mono-tridecanoate, sucrose mono-tetradecanoate, a coco-glucoside, alkylsaccharides, a cyclodextrin (e.g., alpha-cyclodextrin, beta-cyclodextrin, gamma-cyclodextrin, methyl-beta-cyclodextrin, hydroxypropyl beta-cyclodextrin), N-[8-(2-hydroxybenzoyl)amino]caprylic acid, a N-[8-(2-hydroxybenzoyl)amino]caprylate, sodium N-[8-(2-hydroxybenzoyl)amino]caprylate, also referred to as "SNAC"), a calcium chelating compound (e.g., ethylenediaminetetraacetic acid (EDTA), cremophor EL (also referred to as "Kolliphor EL"; CAS no. 61791-12-6), chitosan, N,N,N-trimethyl chitosan, benzalkonium chloride, bestatin, or alkanols (e.g., ethanol, decanol), caprylocaproyl polyoxylglycerides (such as caprylocaproyl polyoxyl-8 glycerides; available as LABRASOL® or ACCONON® MC8-2), ethyl caprylate, glyceryl monolaurate, lysophosphatidylcholine, menthol, a C-2o alkylamine, a $C_8$-$C_{20}$ alkenylamine (e.g., oleylamine), phosphatidylcholine, a poloxamer, polyethylene glycol monolaurate, polyoxyethylene, polypropylene glycol monolaurate, a polysorbate (e.g., polysorbate 80), cholic acid (or a cholate salt, e.g., sodium chlolate), a deoxycholate (e.g., sodium deoxycholate), sodium glycocholate, sodium glycodeoxycholate, sodium lauryl sulfate (SDS), sodium decyl sulfate, sodium octyl sulfate, sodium laureth sulfate, N-lauryl sarcosinate, decyltrimethyl ammonium bromide, benzyldimethyl dodecyl ammonium chloride, myristyltrimethyl ammonium chloride, dodecyl pyridinium chloride, or decyldimethyl ammonio propane sulfonate and the like.

In some aspects, the absorption or permeation enhancer may include, but is not limited to sodium caprate, sodium caprylate, sodium palmitate, sodium stearate, sodium citrate, sodium salicylate, sodium salcaprozate (SNAC), a polyethylene glycol (PEG)-modified medium chain fatty acid triglyceride of capric and caprylic acid (such as LABRASOL®, available from Gattefosse, USA), sucrose laurate, or lauroyl-L-carnitine (LC, such as PEPTELLIGENCE®, available from Enteris BioPharma, N.J., USA) and the like. In some aspects, the absorption enhancer is sodium caprate, sodium caprylate, sodium palmitate, sodium stearate, sodium citrate, sodium salicylate, sodium salcaprozate (SNAC), a polyethylene glycol (PEG)-modified medium chain fatty acid triglyceride of capric and caprylic acid, sucrose laurate, or lauroyl-L-carnitine (LC). In some aspects, the absorption or permeation enhancer can be a polyethylene glycol (PEG)-modified medium chain fatty acid triglyceride of capric and caprylic acid.

In another aspect, the present invention relates to a composition, which comprises a peptide of SEQ ID NO: 1 or a pharmaceutically acceptable salt or solvate form thereof in an amount of from about 0.1% to about 15% (w/w) of the composition; an absorption or permeation enhancer in an amount from about 10% to about 60% (w/w); and one or more pharmaceutically acceptable excipients.

In another aspect, the present invention relates to a composition, which comprises a peptide of SEQ ID NO: 1 or a pharmaceutically acceptable salt or solvate form thereof in an amount of from about 0.1% to about 15% (w/w) of the composition; an absorption enhancer; and one or more pharmaceutically acceptable excipients.

In other aspects, the absorption or permeation enhancer used may be sodium salcaprozate. In some aspects, the absorption or permeation enhancer used may include, but is not limited to a polyethylene glycol (PEG)-modified medium chain fatty acid triglyceride of capric and caprylic acid and the like.

In some aspects, the absorption or permeation enhancer used in a composition of the present invention may be, but is not limited to sodium caprate.

In another aspect, the present invention provides compositions which comprise a peptide of SEQ ID NO: 1 or a pharmaceutically acceptable salt or solvate form thereof in an amount of from about 0.1% to about 15% (w/w) of the composition, sodium caprate in an amount of from about 20% to about 45% (w/w) of the composition and a microcrystalline cellulose.

In another aspect, the present invention provides compositions which comprise a peptide of SEQ ID NO: 1 or a pharmaceutically acceptable salt thereof in an amount of from 0.1 to 15% (w/w) of the composition, sodium caprate in an amount of from 20 to 45% (w/w) of the composition and a microcrystalline cellulose.

In some aspects, the sodium caprate can be present in a composition in an amount of from about 1% to about 99% (w/w) of the composition, or from about 5% to about 50% (w/w), or from about 10% to about 50% (w/w), or from about 20% to about 50% (w/w), or from about 30% to about 50% (w/w), or from about 30% to about 40% (w/w), or from about 32% to about 38% (w/w), or from about 35% to about 36% (w/w) of the composition. In some aspects, the sodium caprate is present in an amount of from about 30% to about 40% (w/w).

In some aspects, the sodium caprate can be present in a composition in an amount of from 1 to 99% (w/w) of the composition, or from 5 to 50% (w/w), or from 10 to 50% (w/w), or from 20 to 50% (w/w), or from 30 to 50% (w/w), or from 30 to 40% (w/w), or from 32 to 38% (w/w), or from 35 to 36% (w/w) of the composition. In some aspects, the sodium caprate is present in an amount of from 30 to 40% (w/w). For example, sodium caprate can be present in an amount of about 30%, 31%, 32%, 33%, 34%, 35%, 36%, 37%, 38%, 39%, or 40% (w/w) of the composition, including any fractional amounts in between. In some aspects, the sodium caprate can be present in an amount from about 32% to about 38% (w/w). In some aspects, the sodium caprate can be present in an amount of about 35.7% (w/w).

In one aspect, for use in compositions of the present invention, sodium caprate may have a purity of at least 98%, 98.2%, 98.4%. 98.6%, 98.8%, 99.0%, 99.5%, or at least 99.9%. Without being bound by any theory, the higher degree of purity of the sodium caprate can provide improved bioavailability compared to lower technical grade sodium caprate, such 90% or 95% pure sodium caprate. In some aspects, sodium caprate has a purity of at least 98% for use in the present invention.

In another aspect, for use in the present invention, sodium caprate may have an average particle size of from about 10 nm to about 150 microns. In some aspects, sodium caprate particles suitable for use in the present invention may have an average diameter from about 1 micron to about 150 microns. In some aspects, such sodium caprate particles may have an average diameter from about 50 microns to about 150 microns. In other aspects, the sodium caprate particles may have an average diameter of from about 10 nm to about 5 microns. In some aspects, the sodium caprate particles may have an average diameter of from about 50 nm to about 1 micron. In some aspects, the sodium caprate particles may have an average diameter of from about 100 nm to about 800 nm.

In some aspects, sodium caprate can be provided in various particle sizes. In some aspects, sodium caprate particles can have an average diameter from 10 nm to 150 microns. In some aspects, sodium caprate particles can have an average diameter from 1 micron to 150 microns. In some aspects, sodium caprate particles can have an average diameter from 50 microns to 150 microns. In other aspects, the sodium caprate particles can have an average diameter of from 10 nm to 5 microns. In some aspects, the sodium caprate particles can have an average diameter of from 50 nm to 1 micron. In some aspects, the sodium caprate particles can have an average diameter of from 100 nm to about 800 nm.

In another aspect, sodium caprate may be present in any form to be adapted for use in compositions of the present invention. In some aspects, the sodium caprate can be in crystalline form, amorphous form, or semi-crystalline form. In some aspects, the use of crystalline sodium caprate can enhance bioavailability of the peptide of SEQ ID NO: 1. In some aspects, the use of amorphous sodium caprate can enhance bioavailability of the peptide of SEQ ID NO: 1. In some aspects, the use of semi-crystalline sodium caprate can enhance bioavailability of the peptide of SEQ ID NO: 1.

In some aspects, the use of crystalline sodium caprate may enhance bioavailability of the peptide of SEQ ID NO: 1 or a pharmaceutically acceptable salt or solvate form thereof. In some aspects, the use of amorphous sodium caprate may enhance bioavailability of the peptide of SEQ ID NO: 1 or a pharmaceutically acceptable salt or solvate form thereof. In some aspects, the use of semi-crystalline sodium caprate may enhance bioavailability of the peptide of SEQ ID NO: 1 or a pharmaceutically acceptable salt or solvate form thereof.

In another aspect, the peptide of SEQ ID NO: 1 or a pharmaceutically acceptable salt or solvate form thereof and the sodium caprate may be combined in any suitable format as defined in the present specification for use or adaptation in the present invention. In some aspects, the peptide of SEQ ID NO: 1 or a pharmaceutically acceptable salt or solvate form thereof and the sodium caprate may form a mixture or a granulated mixture.

In some aspects, the peptide of SEQ ID NO: 1 or a pharmaceutically acceptable salt or solvate form thereof and the sodium caprate form a mixture or a granulated mixture.

In some aspects, the peptide of SEQ ID NO: 1 or a pharmaceutically acceptable salt or solvate form thereof and the sodium caprate form a mixture.

In some aspects, the peptide of SEQ ID NO: 1 or a pharmaceutically acceptable salt or solvate form thereof and the sodium caprate form a granulated mixture. In some aspects, the peptide of SEQ ID NO: 1 and the sodium caprate can be a granulated mixture.

Accordingly, the peptide of SEQ ID NO: 1 or a pharmaceutically acceptable salt or solvate form thereof and the sodium caprate can be mixed to form a granulated mixture. The granulated mixture may be formed of particles having any average diameter suitable for use in compositions of the present invention. For example, the particles of the granulated mixture can have an average diameter of from about 100 nm to about 5 microns. The particles can also have an average diameter from about 1 micron to about 150 microns. In some aspects, the particles of the granulated mixture of the composition of the present invention may have an average diameter of from about 200 nanometers to about 1 micron.

In some aspects, the peptide of SEQ ID NO: 1 and the sodium caprate can be mixed to form a granulated mixture. In some aspects, the peptide of SEQ ID NO: 1 and the sodium caprate form a granulated mixture. In some aspects, the particles of the granulated mixture can have an average diameter of from 100 nm to 5 microns. The particles can also have an average diameter from 1 micron to 150 microns. In some aspects, the particles of the granulated mixture can have an average diameter of from 200 nanometers to 1 micron.

In other aspects, when the composition is a tablet composition, the compositions may include, but are not limited to a two phase structure in which an external phase includes microcrystalline cellulose, which may act as a protective barrier between the sodium caprate, which resides in an internal phase, and an enteric coating that may ensure proper intestinal delivery.

In another aspect, the internal phase can include: the peptide of SEQ ID NO: 1 or a pharmaceutically acceptable salt or solvate form thereof in an amount of about 1.8% (w/w); and sodium caprate in an amount of about 35.7% (w/w).

In another aspect, the internal phase can include: the peptide of SEQ ID NO: 1 in an amount of about 1.8% (w/w); and sodium caprate in an amount of about 35.7% (w/w).

In some aspects, the present invention provides a composition which comprises, an internal phase which comprises a peptide of SEQ ID NO: 1 or a pharmaceutically acceptable salt or solvate form thereof: in an amount of from about 0.1% to about 15% (w/w) of the composition, and sodium caprate in an amount of from about 20% to about 45% (w/w) of the composition, and an external phase disposed over the internal phase, where the external phase comprises a microcrystalline cellulose.

In some aspects, the present invention provides a composition which comprises, an internal phase which comprises a peptide of SEQ ID NO: 1 or a pharmaceutically acceptable salt or solvate form thereof: in an amount of from about 0.1% to about 10% (w/w) of the composition, and sodium caprate in an amount of from about 20% to about 45% (w/w) of the composition, and an external phase disposed over the internal phase, where the external phase comprises a microcrystalline cellulose.

In some aspects, the present invention provides a composition which comprises, an internal phase which comprises a peptide of SEQ ID NO: 1 in an amount of from 0.1 to 10% (w/w) of the composition, and sodium caprate in an amount of from 20 to 45% (w/w) of the composition, and an external phase disposed over the internal phase, where the external phase comprises a microcrystalline cellulose.

The internal phase may include a variety of other pharmaceutically acceptable component(s) or excipient(s), such as, including, but is not limited to, a glidant, a lubricant, a disintegrant, a binder, a desiccant, a filler, and other components or excipients and the like.

Representative disintegrants suitable for use in the present invention, may include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums (like gellan), low-substituted hydroxypropyl cellulose, or mixtures thereof and the like. In some aspects, disintegrants suitable for use in the present invention, may include, but are not limited to croscarmellose sodium. Such a disintegrant may be present in an amount of from about 1% to about 99% (w/w) of a composition of the present invention, or from about 1% to 50%, or from about 1% to about 25%, or from about 1% to about 20%, or from about 1% to about 10%, or from about 2% to about 8%, or from about 4% to about 6% (w/w) of the composition. Disintegrants suitable for use in the present invention may also be present in an amount of about 1% (w/w), 2%, 3%, 4%, 5%, 6%, 7%, 8%, 9%, or about 10% (w/w) of the composition, which include, but is not limited to any fractional amount in between. In some aspects, a disintegrant may be present in an amount of about 1% to about 10% (w/w) of a composition of the present invention.

In some aspects, a disintegrant may be present in an amount of from 1 to 99% (w/w) of the composition, or from 1 to 50%, or from 1 to 25%, or from 1 to 20%, or from 1 to 10%, or from 2 to 8%, or from 4 to 6% (w/w) of the composition. Disintegrants for use in the present invention may also be present in an amount of about 1% (w/w), 2%, 3%, 4%, 5%, 6%, 7%, 8%, 9%, or about 10% (w/w) of the composition, which include, but is not limited to any fractional amount in between. In some aspects, a disintegrant may be present in the internal phase of the composition in an amount of 1 to 10% (w/w) of the composition. In some aspects, a disintegrant may be present in the internal phase of the composition in an amount of about 5% (w/w) of a composition of the present invention.

In another aspect, a composition of the present invention may also include, but is not limited to hydrophilic silica in any amount for purposes of the present invention. In particular, hydrophilic silica is exemplified by Aerosil 200, having a specific surface area of about 200 m$^2$/g. Alternatives to hydrophilic silica may include, but are not limited to talc, sodium ferrocyanide, potassium ferrocyanide, calcium carbonate, magnesium carbonate, silicon dioxide, precipitated silica, sodium aluminosilicate, combinations thereof and the like.

In some aspects, a composition of the present invention may further comprise hydrophilic silica. In one aspect, hydrophilic silica may be present in compositions of the present invention in an amount of from about 0.1% to about 10% (w/w) of the composition, or from about 0.1% to about 5%, or from about 0.1% to about 2%, or from about 0.1% to about 1.5%, or from about 0.1% to about 1%, or from about 0.3% to about 0.7% (w/w) of the composition of the present invention. In another aspect, a composition of the present invention may further comprise hydrophilic silica in an amount of from about 0.1% to about 1.5% (w/w) of the composition. In another aspect, a composition of the present invention may further comprise hydrophilic silica in an amount of about 1.0% (w/w) of the composition.

In one aspect, hydrophilic silica may be present in compositions of the present invention in an amount of from 0.1 to 10% (w/w) of the composition, or from 0.1 to 5%, or from 0.1 to 2%, or from 0.1 to 1.5%, or from 0.1 to 1%, or from 0.3 to 0.7% (w/w) of the composition of the present invention. For example, hydrophilic silica use in the present invention may be present in an amount of about 0.1%, 0.2%, 0.3%, 0.4%, 0.5%, 0.6%, 0.7%, 0.8%, 0.9%, 1.0%, or 1.5% (w/w) of the composition, including any fraction amount in between as defined. In another aspect, a composition of the present invention may further comprise hydrophilic silica in an amount of from 0.1% to 1.5% (w/w) of the composition. In further aspects, a composition of the present invention may further comprise hydrophilic silica in an amount of about 0.5% (w/w) of the composition.

In some aspects, the composition further may comprise hydrophilic silica in an internal phase. In some aspects, the composition further may comprise hydrophilic silica in an amount of from about 0.1% to about 1.5% (w/w) of the composition. In some aspects, the composition further may comprise hydrophilic silica in an amount of about 0.5% (w/w) of the composition.

The internal phase may include, but is not limited to at least one disintegrant in an effective therapeutic amount for use in compositions as determined in accordance with the present invention. Representative disintegrants suitable for use in the present invention, include, but are not limited to, starches, clays, celluloses, alginates and gums and cross-linked starches, celluloses and polymers, combinations thereof and the like. Additional representative disintegrants suitable for use in the present invention, may include, but are not limited to microcrystalline cellulose, croscarmellose sodium, alginic acid, sodium alginate, crospovidone, cellulose, agar and related gums, sodium starch glycolate, corn starch, potato starch, sodium starch glycolate, Veegum HV, methylcellulose, agar, bentonite, carboxymethylcellulose, alginic acid, guar gum combinations thereof, and the like.

In some aspects, a disintegrant may be present in the internal phase of in an amount of about 1% to about 10% (w/w) of a composition of the present invention. In some aspects, a disintegrant may be present in the internal phase in an amount of about 5.0% (w/w) of a composition of the present invention In another aspect, the internal phase of a composition of the present invention may further comprise at least one of: a disintegrant in an amount from about 1% to about 10% (w/w) of the composition, a microcrystalline cellulose in an amount from about 1% to about 10% (w/w) of the composition, a hydrophilic silica in an amount from about 0.1% to about 1.5% (w/w) of the composition, or sorbitol in an amount from about 5% to about 15% (w/w) of the composition.

In yet another aspect, the internal phase of the composition further may comprise: a disintegrant in an amount from about 1% to about 10% (w/w) of the composition; a microcrystalline cellulose in an amount from about 1% to about 10% (w/w) of the composition; a hydrophilic silica in an amount from about 0.1% to about 1.5% (w/w) of the composition; and sorbitol in an amount from about 5% to about 15% (w/w) of the composition.

In another aspect, the internal phase of a composition of the present invention may further comprise at least one of: a disintegrant in an amount from 1% to 10% (w/w) of the composition, a microcrystalline cellulose in an amount from 1% to 10% (w/w) of the composition, a hydrophilic silica in an amount from 0.1% to 1.5% (w/w) of the composition, or sorbitol in an amount from 5% to 15% (w/w) of the composition.

In yet another aspect, the internal phase of the composition further may comprise: a disintegrant in an amount from 1% to 10% (w/w) of the composition; a microcrystalline cellulose in an amount from 1% to 10% (w/w) of the composition; a hydrophilic silica in an amount from 0.1% to 1.5% (w/w) of the composition; and sorbitol in an amount from 5% to 15% (w/w) of the composition.

In some aspects, the internal phase of compositions of the present invention further may comprise at least one of: a microcrystalline cellulose in an amount of about 3.9% (w/w); sorbitol in an amount of about 10.7% (w/w); a disintegrant in an amount of about 5.0% (w/w); and a hydrophilic silica in an amount of about 0.5% (w/w).

In some aspects, the internal phase of the compositions further may comprise: a microcrystalline cellulose in an amount of about 3.9% (w/w); sorbitol in an amount of about 10.7% (w/w); a disintegrant in an amount of about 5.0% (w/w); and a hydrophilic silica in an amount of about 0.5% (w/w).

In some aspects, the internal phase of compositions further may comprise: Avicel PH101 in an amount of about 3.9% (w/w); sorbitol in an amount of about 10.7% (w/w);

croscarmellose sodium in an amount of about 5.0% (w/w); and Aerosil 200 in an amount of about 0.5% (w/w).

The microcrystalline cellulose of the external phase can include any microcrystalline cellulose known in the art. In some aspects, the microcrystalline cellulose of the external phase may comprise a silicified microcrystalline cellulose (SMCC). In some aspects, silicified microcrystalline cellulose may include, but is not limited to SMCC 50, SMCC SOLD, SMCC 90, SMCC HD90 or SMCC 90LM and the like.

In some aspects, for use in the present invention, microcrystalline cellulose of the external phase may be a silicified microcrystalline cellulose (SMCC) and may have any particle size (i.e., as adapted for use for the present invention). In some aspects, the external phase includes silicified microcrystalline cellulose in an amount of from about 25% to about 45% (w/w) of the composition. In some aspects, the external phase includes silicified microcrystalline cellulose in an amount of about 27.7% (w/w) of the composition. In some aspects, the external phase includes silicified microcrystalline cellulose in an amount of about 31.0% (w/w) of the composition. In some aspects, the external phase includes silicified microcrystalline cellulose in an amount of about 59.6% (w/w) of the composition.

In some aspects, the external phase includes silicified microcrystalline cellulose in an amount of from 25 to 45% (w/w) of the composition. In some aspects, the external phase includes silicified microcrystalline cellulose in an amount of about 36.6% (w/w) of the composition.

The external phase can include a variety of other pharmaceutically excipients or components, which may include, but is not limited to a glidant, a disintegrant, a binder, a desiccant, a filler, and other components and the like. For use in the present invention, a disintegrant may be present in the compositions in an amount of from 0.1 to 10% (w/w) of the composition, or from 0.1 to 5%, or from 0.1 to 2%, or from 0.1 to 1.5%, or from 0.1 to 1%, or from 0.1 to 0.4% (w/w) of the composition. For example, the hydrophilic silica can be present in an amount of about 0.1%, 0.2%, 0.25%, 0.3%, 0.4%, 0.5%, 0.6%, 0.7%, 0.75%, 0.8%, 0.9%, 1.0%, or 1.5% (w/w) of the composition, including any fraction amount in between as defined herein. In some aspects, the external phase further may comprise a disintegrant. In some aspects, the external phase further may comprise hydrophilic silica in an amount of from 0.1% to 1.5% (w/w) of the composition. In some aspects, the external phase further may comprise a disintegrant in an amount of about 0.25% (w/w) of the composition.

In the present invention, the external phase may include a glidant in any suitable amount for use in compositions as described herein. Examples of suitable glidants for use in the present invention, may include, but are not limited to magnesium carbonate, magnesium laurylsulphate, calcium silicate, talc, fumed silicon dioxide, combinations thereof, and the like. Other useful suitable glidants, may include, but are not limited to magnesium stearate, calcium stearate, stearic acid, sodium stearyl fumarate, polyethylene glycol, sodium lauryl sulphate, magnesium lauryl sulphate, sodium benzoate, colloidal silicon dioxide, magnesium oxide, microcrystalline cellulose, starches, mineral oil, waxes, glyceryl behenate, polyethylene glycol, sodium acetate, sodium chloride, combinations thereof, and the like.

The external phase can include at least one disintegrant in any suitable amount in accordance with the present invention. In one aspect, the disintegrant may include croscarmellose sodium. For use in the present invention, a disintegrant may be present in the compositions in an amount of from about 0.1% to about 10% (w/w) of the composition, or from about 0.1% to about 5%, or from about 0.1% to about 2%, or from about 0.1% to about 1.5%, or from about 0.1% to about 1%, or from about 0.1% to about 0.4% (w/w) of the composition. In another aspect, the suitable disintegrant may be, but is not limited to being present in an amount of about 1% (w/w), 2%, 3%, 4%, 5%, 6%, 7%, 8%, 9%, or about 10% (w/w) of the composition, including any fractional amount in between as defined in the present invention. In another aspects of the present invention, disintegrant may be, but is not limited to being present in an external phase of the composition in an amount of about 1% to about 10% (w/w) of the composition. In other aspects, the disintegrant may be present in the external phase of the composition in an amount of about 5.0% (w/w) of the composition.

In another aspect, the external phase may also include hydrophilic silica in any amount in accordance with the present invention. Hydrophilic silica is exemplified by Aerosil 200, having a specific surface area of about 200 m$^2$/g. Suitable alternatives to hydrophilic silica for use in the present invention include, without limitation, talc, sodium ferrocyanide, potassium ferrocyanide, calcium carbonate, magnesium carbonate, silicon dioxide, precipitated silica, sodium aluminosilicate, and combinations thereof and the like. Hydrophilic silica may be present in the compositions in an amount of from about 0.1 to 10% (w/w) of the composition, or from about 0.1 to 5%, or from about 0.1 to 2%, or from about 0.1 to 1.5%, or from about 0.1 to 1%, or from about 0.3 to 0.7% (w/w) of the composition. For example, the hydrophilic silica can be present in an amount of about 0.1%, 0.2%, 0.3%, 0.4%, 0.5%, 0.6%, 0.7%, 0.8%, 0.9%, 1.0%, or 1.5% (w/w) of the composition, including any fraction amount in between.

In some aspects, the external phase of the compositions disclosed herein can further comprise at least one of: a glidant in an amount from about 0.1% to about 0.5% by weight of the composition, a disintegrant in an amount from about 1% to about 10% by weight of the composition, or a hydrophilic silica in an amount from about 0.1% to about 1.5% by weight of the composition.

In some aspects, the external phase of the compositions further can include: a glidant in an amount from about 0.1% to about 0.5% by weight of the composition; a disintegrant in an amount from about 1% to about 10% by weight of the composition; and a hydrophilic silica in an amount from about 0.1% to about 1.5% by weight of the composition.

In some aspects, the external phase of the compositions disclosed herein can further comprise at least one of: a glidant in an amount from 0.1% to 0.5% by weight of the composition, a disintegrant in an amount from 1% to 10% by weight of the composition, or a hydrophilic silica in an amount from 0.1% to 1.5% by weight of the composition.

In some aspects, the external phase of the compositions further can include: a glidant in an amount from 0.1% to 0.5% by weight of the composition; a disintegrant in an amount from 1% to 10% by weight of the composition; and a hydrophilic silica in an amount from 0.1% to 1.5% by weight of the composition.

In some aspects, the external phase of the compositions disclosed herein can further comprise at least one of: a disintegrant in an amount of about 5.0% (w/w); a hydrophilic silica in an amount of about 0.5% (w/w); and a glidant in an amount of about 0.25% (w/w).

In some aspects, the external phase of the compositions comprises: a silicified microcrystalline cellulose in an amount of about 36.6% (w/w); a disintegrant in an amount of about 5.0% (w/w); a hydrophilic silica in an amount of about 0.5% (w/w); and a glidant in an amount of about 0.25% (w/w).

In some aspects, the external phase of the compositions can include: SMCC HD90 in an amount of about 36.6% (w/w); croscarmellose sodium in an amount of about 5.0% (w/w); Aerosil 200 in an amount of about 0.5% (w/w); and magnesium stearate in an amount of about 0.25% (w/w).

In some aspects, a composition of the present invention may be in a dosage form, which may be, but is not limited to a tablet or capsule dosage form. In some aspects, the composition may be a tablet or capsule composition. In some aspects, the composition can be a tablet composition. In some aspects, such as tablet composition may comprise a unit dose size in amounts which may include, but is not limited to amounts from about 25 mg to about 2000 mg, from about 500 mg to about 2000 mg. Compositions of the present invention, may be of any suitable size in accordance with the present invention, such as, but not limited tablets or capsules in doses or amounts of 25, 50, 75, 100, 110, 120, 130, 140, 150, 160, 170, 180, 190, 200, 250, 300, 350, 400, 450, 500, 550, 600, 650, 700, 750, 800, 850, 900, 950, 1050, 1100, 1150, 1200, 1250, 1300, 1350, 1400, 1450, 1500, 1550, 1600, 1650, 1700, 1750, 1800, 1850, 1900, 1950 or 2000 milligrams (mg) and the like. In one aspect, a composition of the present invention may be as a 25 mg, 50 mg, 100 mg or 1400 mg tablet, respectively, which may be administered, but is not limited to once or twice daily or as determined by medical necessity. In some aspects, the composition may be a unit dose size of from about 500 mg to about 2000 mg. In some aspects, the composition may be a unit dose size of about 1400 mg.

In some aspects, such as tablet composition may comprise a unit dose size from 500 mg to about 2000 mg. The tablet compositions may be of any suitable size in accordance with the present invention, such as, but not limited to 25, 50, 75, 100, 110, 120, 130, 140, 150, 160, 170, 180, 190, 200, 250, 300, 350, 400, 450, 500, 550, 600, 650, 700, 750, 800, 850, 900, 950, 1050, 1100, 1150, 1200, 1250, 1300, 1350, 1400, 1450, 1500, 1550, 1600, 1650, 1700, 1750, 1800, 1850, 1900, 1950 or 2000 mg tablets. In some aspects, the composition is a 1400 mg tablet.

Tablets formed from compositions of the present invention may be administered in single or multiple administrations depending on dosing and frequency as required and tolerated by the patient, where such tablets contain a sufficient quantity or amount of active agent to effectively treat specific disease state. Thus, in one aspect, the present invention relates to a composition for oral administration of the peptide of SEQ ID NO: 1 or pharmaceutically acceptable salt or solvate form thereof, which may be taken in a daily amount of from about 0.05 to about 30 mg per kg of body weight per day. In some aspects, dosages can be from about 0.1 mg to about 20 mg per kg of body weight per day. In another aspect, dosages can be from about 0.1 mg to about 5 mg per kg of body weight per day. In another aspect, dosages can be from about 0.1 mg to about 1 mg per kg of body weight per day.

In some aspects, the present invention relates to a composition for oral administration of the peptide of SEQ ID NO: 1 which may be taken in a daily amount of from 0.05 to 30 mg per kg of body weight per day. In some aspects, dosages can be from 0.1 mg to 20 mg per kg of body weight per day. In another aspect, dosages can be from 0.1 mg to 5 mg per kg of body weight per day. In another aspect, dosages can be from 0.1 mg to 1 mg per kg of body weight per day.

In some aspects, the present invention provides for compositions that include an internal phase which comprises: the peptide of SEQ ID NO: 1 or a pharmaceutically acceptable salt or solvate form thereof in an amount of about 1.8% (w/w), and sodium caprate in an amount of about 35.7% (w/w); and an external phase which comprises silicified microcrystalline cellulose HD90 in an amount of about 36.6% (w/w).

In some aspects, the present invention provides for compositions that include an internal phase which comprises: the peptide of SEQ ID NO: 1 in an amount of about 1.8% (w/w), and sodium caprate in an amount of about 35.7% (w/w); and an external phase which comprises silicified microcrystalline cellulose HD90 in an amount of about 36.6% (w/w).

In some aspects, the composition can include:
an internal phase which comprises: a granulated mixture of a peptide of SEQ ID NO: 1 in an amount of about 1.8% (w/w) and sodium caprate in an amount of about 35.7% (w/w); a microcrystalline cellulose in an amount of about 3.9% (w/w);
sorbitol in an amount of about 10.7% (w/w); a disintegrant in an amount of about 5.0% (w/w); and a hydrophilic silica in an amount of about 0.5% (w/w); and
an external phase disposed over the core, the external phase which comprises: a silicified microcrystalline cellulose in an amount of about 36.6% (w/w); a disintegrant in an amount of about 5.0% (w/w); a hydrophilic silica in an amount of about 0.5% (w/w); and a glidant in an amount of about 0.25% (w/w).

In some aspects, the composition can include:
an internal phase which comprises: a granulated mixture of the acetate form of the peptide of SEQ ID NO: 1 in an amount of about 7.1% (w/w), and sodium caprate in an amount of about 35.7% (w/w); microcrystalline cellulose in an amount of about 3.9% (w/w);
sorbitol in an amount of about 10.7% (w/w); croscarmellose sodium in an amount of about 5.0% (w/w); colloidal anhydrous silica in an amount of about 0.5% (w/w); and magnesium stearate in an amount of about 0.25% (w/w); and
an external phase which comprises: silicified microcrystalline cellulose in an amount of about 31.0% (w/w); a croscarmellose sodium in an amount of about 5.0% (w/w); colloidal anhydrous silica in an amount of about 0.5% (w/w); and magnesium stearate in an amount of about 0.25% (w/w).

In some aspects, the composition can include:
an internal phase which comprises: a granulated mixture of the acetate form of the peptide of SEQ ID NO: 1 in an amount of about 10.7% (w/w), and sodium caprate in an amount of about 35.7% (w/w); microcrystalline cellulose in an amount of about 3.9% (w/w);
sorbitol in an amount of about 10.7% (w/w); croscarmellose sodium in an amount of about 5.0% (w/w); and colloidal anhydrous silica in an amount of about 0.5% (w/w); and
an external phase which comprises: silicified microcrystalline cellulose in an amount of about 27.7% (w/w); a croscarmellose sodium in an amount of about 5.0% (w/w);
colloidal anhydrous silica in an amount of about 0.5% (w/w); and magnesium stearate in an amount of about 0.25% (w/w).

In some aspects, the composition can include:
an internal phase which comprises: a granulated mixture of a peptide of SEQ ID NO: 1 in an amount of about 1.8% (w/w), and sodium caprate in an amount of about 35.7% (w/w); Avicel PH101 in an amount of about 3.9% (w/w); sorbitol in an amount of about 10.7% (w/w); croscarmellose sodium in an amount of about 5.0% (w/w); and Aerosil 200 in an amount of about 0.5% (w/w); and an external phase which comprises: SMCC HD90 in an amount of about 36.6% (w/w); croscarmellose sodium in an amount of about 5.0% (w/w); Aerosil 200 in an amount of about 0.5% (w/w); and magnesium stearate in an amount of about 0.25% (w/w);

In some aspects, the internal phase of the composition can comprise the acetate form of the peptide of SEQ ID NO: 1 in an amount of about 1.8% (w/w), and sodium caprate in an amount of about 35.7% (w/w); and the external phase comprises: silicified microcrystalline cellulose HD90 in an amount of about 36.6% (w/w).

The compositions of the present invention may also use, but is not limited to a silicified microcrystalline cellulose which may impart a particular stability to the composition by effectively reducing contact between sodium caprate and the enteric coating to preserve the enteric coating integrity for proper intestinal delivery. Moreover, the bioavailability of the peptide of SEQ ID NO: 1 or a pharmaceutically acceptable salt or solvate form thereof can demonstrate improved bioavailability through use of an absorption enhancer, for example, a permeation enhancer such as sodium caprate. In particular, sodium caprate having a purity greater than 98% may improve bioavailability. Bioavailability may also be improved by use of a particular size of the sodium caprate particles, as well as the degree of crystallinity of the sodium caprate source.

In some aspects, the internal phase can comprise: a granulated mixture of the acetate form of the peptide of SEQ ID NO: 1 in an amount of about 1.8% (w/w), and sodium caprate in an amount of about 35.7% (w/w); a microcrystalline cellulose in an amount of about 3.9% (w/w); sorbitol in an amount of about 10.7% (w/w); a disintegrant in an amount of about 5.0% (w/w); and a hydrophilic silica in an amount of about 0.5% (w/w); and the external phase comprises: a silicified microcrystalline cellulose in an amount of about 36.6% (w/w); a disintegrant in an amount of about 5.0% (w/w); a hydrophilic silica in an amount of about 0.5% (w/w); and a glidant in an amount of about 0.25% (w/w).

In some aspects, the composition can include:
an internal phase which comprises: granulated mixture of the acetate form of the peptide of SEQ ID NO: 1 in an amount of about 1.8% (w/w), and sodium caprate in an amount of about 35.7% (w/w); a microcrystalline cellulose in an amount of about 3.9% (w/w); sorbitol in an amount of about 10.7% (w/w); croscarmellose sodium in an amount of about 5.0% (w/w); and colloidal anhydrous silica in an amount of about 0.5% (w/w); and
an external phase which comprises: a silicified microcrystalline cellulose in an amount of about 36.6% (w/w); croscarmellose sodium in an amount of about 5.0% (w/w); colloidal anhydrous silica in an amount of about 0.5% (w/w); and magnesium stearate in an amount of about 0.25% (w/w).

In some aspects, the internal phase can comprise: a granulated mixture of the acetate form of the peptide of SEQ ID NO: 1 in an amount of about 1.8% (w/w), and sodium caprate in an amount of about 35.7% (w/w); Avicel PH101 in an amount of about 3.9% (w/w); sorbitol in an amount of about 10.7% (w/w); croscarmellose sodium in an amount of about 5.0% (w/w); and Aerosil 200 in an amount of about 0.5% (w/w); and the external phase comprises: SMCC HD90 in an amount of about 36.6% (w/w); croscarmellose sodium in an amount of about 5.0% (w/w); Aerosil 200 in an amount of about 0.5% (w/w); and magnesium stearate in an amount of about 0.25% (w/w).

In some aspects, the internal phase can comprise: the acetate form of peptide of SEQ ID NO: 1 in an amount of about 7.1% (w/w); and sodium caprate in an amount of about 35.7% (w/w); and the external phase comprises: silicified microcrystalline cellulose HD90 in an amount of about 30.75% (w/w).

In some aspects, the internal phase can comprise: the acetate form of peptide of SEQ ID NO: 1 in an amount of about 10.0% (w/w); and sodium caprate in an amount of about 35.7% (w/w); and the external phase comprises: silicified microcrystalline cellulose HD90 in an amount of about 30.75% (w/w).

In some aspects, the internal phase can comprise: a granulated mixture of the acetate form of the peptide of SEQ ID NO: 1 in an amount of about 7.1% (w/w), and sodium caprate in an amount of about 35.7% (w/w); a microcrystalline cellulose in an amount of about 3.9% (w/w); sorbitol in an amount of about 10.7% (w/w); a disintegrant in an amount of about 5.0% (w/w); a hydrophilic silica in an amount of about 0.5% (w/w); and a glidant in an amount of about 0.25% (w/w); and the external phase comprises: a silicified microcrystalline cellulose in an amount of about 30.75% (w/w); a disintegrant in an amount of about 5.0% (w/w); a hydrophilic silica in an amount of about 0.5% (w/w); and a glidant in an amount of about 0.5% (w/w).

In some aspects, the internal phase can comprise: a granulated mixture of the acetate form of the peptide of SEQ ID NO: 1 in an amount of about 10.0% (w/w), and sodium caprate in an amount of about 35.7% (w/w); a microcrystalline cellulose in an amount of about 3.9% (w/w); sorbitol in an amount of about 10.7% (w/w); a disintegrant in an amount of about 5.0% (w/w); a hydrophilic silica in an amount of about 0.5% (w/w); and a glidant in an amount of about 0.25% (w/w); and the external phase comprises: a silicified microcrystalline cellulose in an amount of about 30.75% (w/w); a disintegrant in an amount of about 5.0% (w/w); a hydrophilic silica in an amount of about 0.5% (w/w); and a glidant in an amount of about 0.5% (w/w).

In some aspects, the internal phase can comprise: a granulated mixture of the acetate form of the peptide of SEQ ID NO: 1 in an amount of about 7.1% (w/w), and sodium caprate in an amount of about 35.7% (w/w); Avicel PH101 in an amount of about 3.9% (w/w); sorbitol in an amount of about 10.7% (w/w); croscarmellose sodium in an amount of about 5.0% (w/w); Aerosil 200 in an amount of about 0.5% (w/w); and magnesium stearate in an amount of about 0.25% (w/w); and the external phase comprises: SMCC HD90 in an amount of about 30.75% (w/w); a croscarmellose sodium in an amount of about 5.0% (w/w); Aerosil in an amount of about 0.5% (w/w); and magnesium stearate in an amount of about 0.5% (w/w).

In some aspects, the internal phase can comprise: a granulated mixture of the acetate form of the peptide of SEQ ID NO: 1 in an amount of about 10.0% (w/w), and sodium caprate in an amount of about 35.7% (w/w); Avicel PH101 in an amount of about 3.9% (w/w); sorbitol in an amount of about 10.7% (w/w); croscarmellose sodium in an amount of about 5.0% (w/w); Aerosil 200 in an amount of about 0.5% (w/w); and magnesium stearate in an amount of about 0.25% (w/w); and the external phase comprises: SMCC HD90 in an amount of about 30.75% (w/w); a croscarmellose sodium in an amount of about 5.0% (w/w); Aerosil in an amount of about 0.5% (w/w); and magnesium stearate in an amount of about 0.5% (w/w).

In some aspects, the internal phase can comprise: a granulated mixture of the acetate form of the peptide of SEQ ID NO: 1 in an amount of about 7.1% (w/w), and sodium caprate in an amount of about 35.7% (w/w); a microcrystalline cellulose in an amount of about 3.9% (w/w); sorbitol in an amount of about 10.7% (w/w); croscarmellose sodium in an amount of about 5.0% (w/w); colloidal anhydrous silica in an amount of about 0.5% (w/w); and magnesium stearate in an amount of about 0.25% (w/w); and the external phase comprises: a silicified microcrystalline cellulose in an amount of about 31.0% (w/w); croscarmellose sodium in an amount of about 5.0% (w/w); colloidal anhydrous silica in an amount of about 0.5% (w/w); and magnesium stearate in an amount of about 0.25% (w/w).

In some aspects, the internal phase can comprise: a granulated mixture of the acetate form of the peptide of SEQ ID NO: 1 in an amount of about 10.7% (w/w), and sodium caprate in an amount of about 35.7% (w/w); a microcrystalline cellulose in an amount of about 3.9% (w/w); sorbitol in an amount of about 10.7% (w/w); croscarmellose sodium in an amount of about 5.0% (w/w); and colloidal anhydrous silica in an amount of about 0.5% (w/w); and the external phase comprises: a silicified microcrystalline cellulose in an amount of about 27.7% (w/w); croscarmellose sodium in an amount of about 5.0% (w/w); colloidal anhydrous silica in an amount of about 0.5% (w/w); and magnesium stearate in an amount of about 0.25% (w/w).

In some aspects, the composition can comprise: the acetate form of peptide of SEQ ID NO: 1 in an amount of about 16.3% (w/w), and sodium caprate in an amount of about 50.0% (w/w). In some aspects, the composition further comprises a poly(ethylene glycol)-block-poly(propylene glycol)-block-poly(ethylene glycol) in an amount of about 6.0% (w/w); mannitol in an amount of about 15.2% (w/w); a disintegrant in an amount of about 10.0% (w/w); a hydrophilic silica in an amount of about 1.0% (w/w); and a glidant in an amount of about 1.5% (w/w). In some aspects, the composition further can comprise: Kolliphor P188 in an amount of about 6.0% (w/w); mannitol in an amount of about 15.2% (w/w); croscarmellose sodium in an amount of about 10.0% (w/w); Aerosil 200 in an amount of about 1.0% (w/w); and magnesium stearate in an amount of about 1.5% (w/w).

In some aspects, the internal phase can comprise: the acetate form of peptide of SEQ ID NO: 1 in an amount of about 1.8% (w/w), and microcrystalline cellulose in an amount of about 21.3% (w/w); sorbitol in an amount of about 10.7% (w/w); croscarmellose sodium in an amount of about 2.5% (w/w); a hydrophilic silica in an amount of about 0.5% (w/w); and magnesium stearate in an amount of about 0.25% (w/w); and the external phase comprises: silicified microcrystalline cellulose HD90 in an amount of about 59.6% (w/w); croscarmellose sodium in an amount of about 2.5% (w/w); a hydrophilic silica in an amount of about 0.5% (w/w); and magnesium stearate in an amount of about 0.25% (w/w).

Coatings

In some aspects, the composition further can include a subcoating of a PVA-PEG graft co-polymer disposed over the composition. In some aspects, compositions can comprise a subcoating of a PVA-PEG graft co-polymer disposed over the external phase. This coating can serve as a smooth surface to aid in swallowing the tablet. It can also provide a platform for a further layer which can comprise an enteric coating disposed over the subcoating. In some aspects, the subcoating can also provide a vehicle for pigmentation for tablet identification. Other coatings may include, without limitation, HPMC, HPC, PVA, Eudragit E based coatings and the like.

Subcoatings can include the OPADRY® class of products and can be present in any desired amounts. In some aspects, the subcoating can be present in an amount from about 1% to about 10% (w/w). In some aspects, the subcoating can be present in an amount from about 1% to about 3% (w/w) relative to the combined internal and external phase of the compositions. For example, the subcoating can be present in amounts including about 1%, 1.5%, 2.0%, 2.5%, and about 3%, including any fractional amounts in between. In one aspect, the subcoating can be present in an amount of about 3%.

In some aspects, the subcoating can be present in an amount from 1% to 10% (w/w). In some aspects, the subcoating can be present in an amount from 1% to 3% (w/w) relative to the combined internal and external phase of the compositions. For example, the subcoating can be present in amounts including about 1%, 1.5%, 2.0%, 2.5%, and 3%, including any fractional amounts in between.

In some aspects, the compositions can comprise a subcoating disposed over the external phase. In some aspects, the composition further can comprise an enteric coating disposed over the subcoating. These combined coating can provide moisture barriers, and in the case of the enteric coating allow delivery of the tablet contents to the intestinal tract where the change in pH allows release of the tablet contents.

In some aspects, the composition includes an enteric coating disposed over the subcoating. In some aspects, the enteric coating is selected to provide release of the tablet contents at a pH range from about 5 to about 8. In some aspects, the enteric coating is a pH 5.5 enteric coating. Enteric coatings can include, without limitation, those based on cellulose acetate phthalate (CAP), poly(methacrylic acid-co-methyl methacrylate, cellulose acetate trimellitate (CAT), poly(vinyl acetate phthalate) (PVAP) or hydroxypropyl methylcellulose phthalate (HPMCP) and the like. In some aspects, the enteric coating can be present in an amount from about 1% to about 15% (w/w). In some aspects, the enteric coating can make up from about 5% to about 15% (w/w) relative to the combined internal and external phase of the compositions. In one aspect, the enteric coating can be present in an amount of about 12%.

In some aspects, the enteric coating is selected to provide release of the tablet contents at a pH range from 5 to 8. In some aspects, the enteric coating is a pH 5.5 enteric coating. Enteric coatings can include, without limitation, those based on cellulose acetate phthalate (CAP), poly(methacrylic acid-co-methyl methacrylate, cellulose acetate trimellitate (CAT), poly(vinyl acetate phthalate) (PVAP) or hydroxypropyl methylcellulose phthalate (HPMCP). In some aspects, the enteric coating can be present in an amount from 1% to 15% (w/w) and the like. In some aspects, the enteric coating can make up from 5% to 15% (w/w) relative to the combined internal and external phase of the compositions. For example, the amounts of enteric coating can be in an amount of about 5%, 6%, 7%, 8%, 9%, 10%, 11%, 12%, 13%, 14%, or 15% (w/w), including fractions thereof.

In some aspects, the composition further can comprise: a subcoating of OPADRY® QX pink in an amount of about 3% (w/w); and an enteric coating of ACRYL-EZE® white in an amount of about 12% (w/w).

In some aspects, the tablet compositions of the present invention may have a bioavailability of at least about 1% to about 10% (w/w). Bioavailability can be measured using area under curve (AUC) for oral dosing versus AUC by intravenous dosing. For example, bioavailability may be about 1%, 2%, 3%, 4%, 5%, 6%, 7%, 8%, 9%, or about 10%. In some aspects, the tablet compositions of the present invention may have a bioavailability in a range from about 10% to about 50%.

In some aspects, the tablet compositions of the present invention may have a bioavailability of from 1% to 10% (w/w), as measured using area under curve (AUC) for oral dosing versus AUC by intravenous dosing. For example, bioavailability may be about 1%, 2%, 3%, 4%, 5%, 6%, 7%, 8%, 9%, or about 10%. In some aspects, bioavailability may be in a range from 10% to 50%. In some aspects, the composition has a bioavailability of at least 1 to 10%.

IV. Methods or Processes of Making Tablets or Dosage Forms

In accordance with the present invention, compositions are comprised of active principal ingredient (i.e., a peptide of SEQ ID NO: 1 or a pharmaceutically acceptable salt or solvate form thereof) and additional pharmaceutically acceptable ingredients (i.e., which may include, but is not limited to absorption enhancer), adjuvants, carriers, excipients or stabilizers, etc as defined throughout the instant disclosure. The percentage or amount of active principal ingredient (API) in compositions of the present invention, which may of course, be varied as amount of active compound in such therapeutically useful compositions is such that a suitable dosage for administration in a subject or patient will be obtained. It will be appreciated that the actual preferred dosages of API being used in the compositions of this invention will vary according to the particular composition formulated, the mode of administration, the particular site of administration and the host being treated. The choice of initial dosage most appropriate for the particular patient is determined by the practitioner using well-known medical principles, including, but is not limited to, body weight.

Moreover, an oral tablet dosage form of the present invention may have a surface layer is coated with an enteric coat, which may be, but is not limited to an enteric coating set forth in the Definition section of the instant specification. For example, an oral tablet dosage form may be formulated with, but not limited to core components, separate sequential layers or combinations thereof, where tablet components, such as core, other layers, etc. may have different release-modifying component properties based upon gastrointestinal environment, pH or time. Hence, an oral tablet dosage form of the present invention may also be coated with a pH sensitive polymer.

Tablets including the compositions of the present invention may be prepared using conventional tablet forming equipment which is conventionally known in the art, which may use compaction, rollers and the like.

In some aspects, the present invention provides a method, which can comprise:
granulating a mixture which comprises: a peptide of SEQ ID NO: 1 or a pharmaceutically acceptable salt or solvate form thereof; and sodium caprate;
adding to the granulated mixture: a microcrystalline cellulose; sorbitol; a disintegrant; and a hydrophilic silica, to form an internal phase;
compressing an external phase over the internal phase, where the external phase comprises a silicified microcrystalline cellulose;
applying a subcoating over the external phase; and
applying an enteric coating over the subcoating to form a tablet.

In some aspects, the present invention provides a tablet made by the process of: granulating a mixture which can comprise: a peptide of SEQ ID NO: 1 or a pharmaceutically acceptable salt or solvate form thereof; and sodium caprate; adding to the granulated mixture: a microcrystalline cellulose; sorbitol; a disintegrant; and a hydrophilic silica, to form an internal phase; compressing an external phase over the internal phase, wherein the external phase comprises a silicified microcrystalline cellulose; applying a subcoating over the external phase; and applying an enteric coating over the subcoating to form a tablet.

In some aspects, the present invention provides a method, which can comprise: granulating a mixture which comprises: a peptide of SEQ ID NO: 1 or a pharmaceutically acceptable salt or solvate form thereof; and sodium caprate; adding to the granulated mixture: a microcrystalline cellulose; sorbitol; a disintegrant; and a hydrophilic silica, to form an internal phase; compressing an external phase over the internal phase, wherein the external phase comprises a silicified microcrystalline cellulose; applying a subcoating over the external phase; and applying an enteric coating over the subcoating to form a tablet.

In some aspects, the present invention relates to a tablet made by the process of:
granulating a mixture, which comprises:
    a peptide of SEQ ID NO: 1 or a pharmaceutically acceptable salt or solvate form thereof; and
    sodium caprate;
adding to the granulated mixture:
    a microcrystalline cellulose;
    sorbitol;
    a disintegrant; and
    a hydrophilic silica, to form an internal phase;
compressing an external phase over the internal phase, wherein the external phase comprises a silicified microcrystalline cellulose;
applying a subcoating over the external phase; and
applying an enteric coating over the subcoating to form a tablet.

Each aspect of the present invention defined in this or in any other section may incorporate definitions and limitations, such as those set forth in Sections I to VI herein and throughout the originally filed disclosure, specification and claims.

V. Methods of Treatments and/or Uses

In one aspect, the present invention relates to a method or use for treating inflammatory disease in a subject which comprises administering to the subject a therapeutically effective amount of a composition disclosed herein. In some aspects, the present invention provides a method of treating inflammatory disease in a subject which comprises administering to the subject a therapeutically effective amount of a composition of the present invention. Suitable inflammatory diseases for treatment with formulations or compositions of the present invention, may include, but is not limited to inflammatory bowel disease (IBD), Crohn's disease (CD), ulcerative colitis (UC), psoriasis (PsO), or psoriatic arthritis (PsA) and the like.

In some aspects, the present invention provides methods or uses for treating a subject afflicted with a condition or indication associated with IL-23 or IL-23R (e.g., activation of the IL-23/IL-23R signaling pathway), where the method or use comprises administering to the subject the compositions of the present invention. In some aspects, a method or use is provided for treating a subject afflicted with a condition or indication characterized by inappropriate, deregulated, or increased IL-23 or IL-23R activity or signaling, which comprises administering to the individual a composition of the present invention in an amount sufficient to inhibit (partially or fully) binding of IL-23 to IL-23R in the subject. In some aspects, the inhibition of IL-23 binding to IL-23R occurs in particular organs or tissues of the subject, i.e., e.g., which includes, but is not limited to organs such as the stomach, small intestine, large intestine/colon, intestinal mucosa, lamina propria, Peyer's Patches, mesenteric lymph nodes, or lymphatic ducts.

In some aspects, methods or uses of the present invention can comprise providing a composition of the present invention to a subject in need thereof. In some aspects, the subject in need thereof has been diagnosed with or has been determined to be at risk of developing a disease or disorder associated with IL-23/IL-23R.

In general, the present invention relates to administrations of:
a. systemically active oral peptide inhibitor of the interleukin-23 receptor (IL-23R) or pharmaceutically acceptable salt or solvate forms thereof;
b. corresponding pharmaceutical compositions thereof;
c. respectively, where each of the above a and b may be used optionally with an absorption enhancer (AbE); and
d. methods and/or uses for treatment of IL-23 driven diseases, which may include, but is not limited to autoimmune inflammation and related diseases and disorders as defined herein.

In accordance with the present invention, systemic drug activity or pharmacological activity, respectively is aimed at those with varying degrees of inflammatory disease or disorder severity, which includes, but is not limited to inflammatory diseases or disorders, which may include, but is not limited to diseases such as psoriasis, psoriatic arthritis, ulcerative colitis, inflammatory bowel disease and the like.

In particular, the present invention relates to:
Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1); or a pharmaceutically acceptable salts or solvates thereof; or corresponding pharmaceutical compositions thereof, which are peptides with systemic activity, systemically inhibit or pharmacologically blocking IL-23 Receptor (IL-23R), IL-23 signalling through IL-23 receptor; or IL-23 pathway, i.e., binds directly to the IL-23R subunit, thereby prevents IL-23 from engaging its receptor and results in inhibiting proximal IL-23R signaling and downstream effector functions (e.g., which may include, but is not limited to cytokine secretion).

Also, the present invention relates to oral administrations of Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1); or pharmaceutically acceptable salt or solvate forms thereof (i.e., a systemically active peptide inhibitor of the interleukin-23 receptor (IL-23R)), corresponding pharmaceutical compositions, methods and/or uses for treatment of IL-23 driven diseases, which may include, but is not limited to autoimmune inflammation and related diseases and disorders as defined herein.

In accordance with the present invention, "systemic activity" for the peptide of SEQ ID NO: 1 or a pharmaceutically acceptable salt thereof and/or corresponding formulations or pharmaceutical compositions, respectively is/are defined: as blocking the IL-23 receptor (IL-23R) in the blood and tissues beyond the gastrointestinal tract, so that IL-23 signaling is inhibited.

In one aspect, the present invention relates to systemic activity that demonstrates efficacy via distribution in the body and treatment of body organ systems, which may include, but is not limited to skin and joint related disorders, i.e., "skin efficacy or joint efficacy", such as in psoriasis or psoriatic arthritis treatments.

Generally, conventionally known peptide therapies must be administered intravenously or intramuscularly. Most peptide therapeutics (e.g. insulin) are metabolized in the gut and therefore have no therapeutic effect if administered orally. In contrast formulations of the peptide of SEQ ID NO: 1, disclosed herein, have been shown to achieve sufficient systemic concentrations of the peptide of SEQ ID NO: 1 after oral dosing to inhibit IL-23R and produce pharmacological effects.

Moreover, the present invention further encompasses pharmaceutical compositions or formulations containing a peptide inhibitor Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1); or a pharmaceutically acceptable salt with and without permeation enhancer as described herein, where such formulations may be used in any indications where higher plasma concentration is required.

Information supporting the above are exemplified in the Examples and throughout the present application.

In one aspect, the present invention relates to the use of Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) or a pharmaceutically acceptable salt or solvate thereof and/or corresponding pharmaceutical compositions thereof in various treatment methods of use as described herein.

In one aspect, the present invention relates to a method for treating a systemic disease or disorder in a subject, comprising orally administering to the subject a therapeutically effective amount of a peptide of SEQ ID NO: 1 or a pharmaceutically acceptable salt or solvate thereof, thereby treating the systemic disease or disorder in the subject.

In one aspect, the present invention relates to a method of producing a systemic level of a therapeutic agent in a subject sufficient to treat a systemic disease or disorder in a subject, comprising orally administering to the subject a therapeutically effective amount of the therapeutic agent, wherein the therapeutic agent is a peptide of SEQ ID NO: 1 or a pharmaceutically acceptable salt or solvate thereof, thereby producing a systemic level of a therapeutic agent in a subject sufficient to treat the systemic disease or disorder.

In some aspects of the present invention, the systemic disease or disorder is psoriasis or psoriatic arthritis. In some aspects, the systemic disease or disorder is psoriasis. In some aspects, the systemic disease or disorder is psoriatic arthritis.

In one aspect, the present invention relates to a method of contacting the skin of a subject with a therapeutically effective amount of a peptide of SEQ ID NO: 1, the method comprising orally administering the peptide of SEQ ID NO: 1 or a pharmaceutically acceptable salt or solvate thereof in a therapeutically effective amount to the subject such that the peptide of SEQ ID NO: 1 contacts the skin of the subject.

In one aspect, the present invention relates to a method of reducing inflammation of the skin of a subject suffering from psoriasis or psoriatic arthritis, comprising contacting the skin of a subject with a therapeutically effective amount of a peptide of SEQ ID NO: 1 or a pharmaceutically acceptable salt or solvate thereof, the method comprising: orally administering the peptide of SEQ ID NO: 1 or a pharmaceutically acceptable salt or solvate form thereof in a therapeutically effective amount such that the peptide of SEQ ID NO: 1 contacts the skin of the subject; thereby reducing the inflammation of the skin of the subject.

In some aspects of the present invention, the peptide of SEQ ID NO: 1 contacts the subject's skin via systemic absorption and circulation.

In one aspect, the present invention relates to a method for IL-23 receptor inhibition for treating inflammatory diseases or disorders by orally delivering a systemically active peptide drug:

(SEQ ID NO: 1)

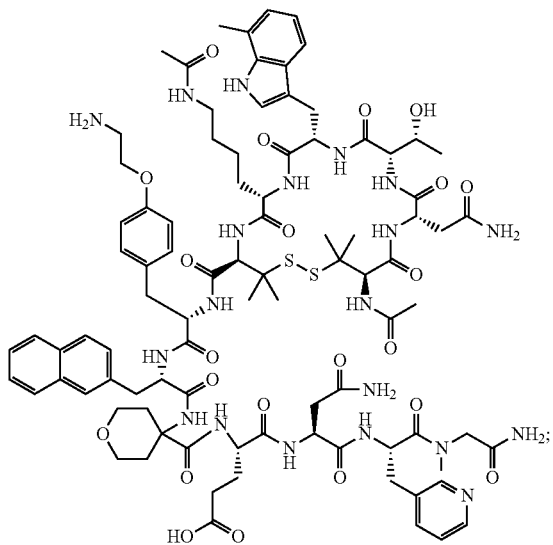

Ac-[Pen]*-N-T-[W(7-Me)]-[Lys(Ac)]-[Pen]*-Phe[4-(2-aminoethoxy)]-[2-Nal]-[THP]-E-N-[3-Pal]-Sarc-NH₂ (*Pen-Pen form disulfide bond)

or a pharmaceutically acceptable salt or solvate form thereof to a patient in need thereof.

In another aspect, the present invention relates to a method for IL-23 receptor inhibition for treating inflammatory diseases or disorders by orally delivering a pharmaceutical composition, which comprises:
[a] a therapeutically effective amount of a systemically active peptide the Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH₂ (*Pen-Pen form disulfide bond) (SEQ ID NO: 1):

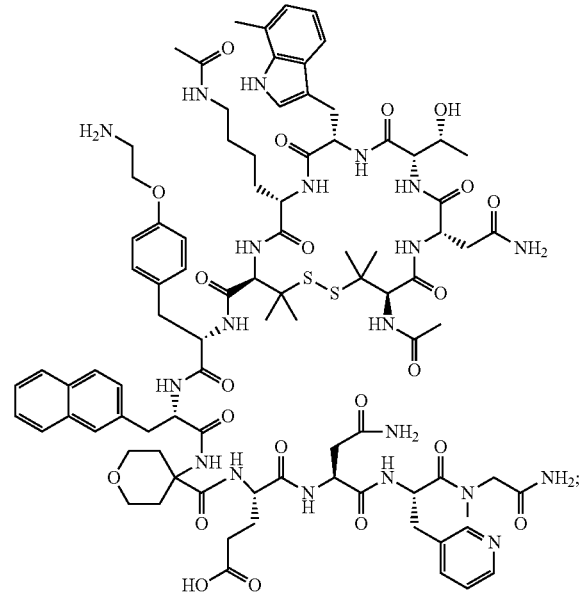 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

or
a pharmaceutically acceptable salt or solvate form thereof;
[b] optionally an absorption enhancer; and
[c] at least one pharmaceutically acceptable excipient;
to a patient in need thereof.

In another aspect, the present invention relates to a method for IL-23 receptor inhibition for treating inflammatory diseases or disorders, where:
the systemically the active peptide of SEQ ID NO: 1 or a pharmaceutically acceptable salt thereof or corresponding pharmaceutical composition thereof.
is or delivered directly via or to blood, blood circulation, tissue, skin or joints for the treatment of inflammatory diseases or disorders.

In another aspect, the present invention relates to a method for systemically inhibiting or pharmacologically blocking:
IL-23 receptor (IL-23R);
IL-23 signalling through IL-23 receptor; or
IL-23 pathway;
for treatment of inflammatory diseases or disorders, which comprises:
orally administering a therapeutically effective amount of a systemically active peptide the (SEQ ID NO: 1)

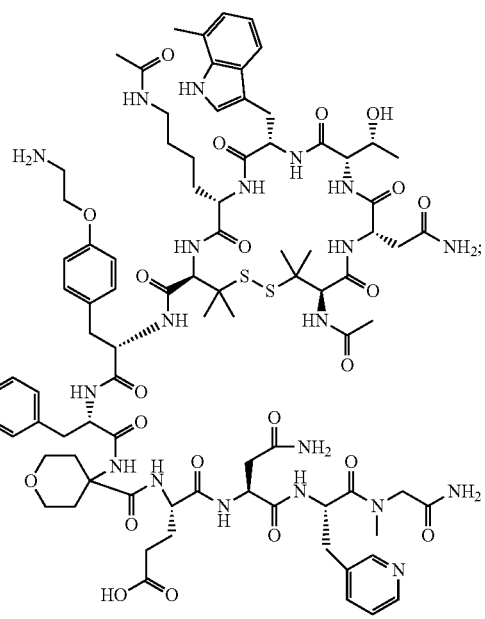

Ac-[Pen]*-N-T-[W(7-Me)]-[Lys(Ac)]-[Pen]*-Phe[4-(2-aminoethoxy)]-[2-Nal]-[THP]-E-N-[3-Pal]- Sarc-NH₂ (*Pen-Pen form disulfide bond)

or
a pharmaceutically acceptable salt or solvate form thereof to a patient in need thereof.

In another aspect, the present invention relates to method for systemically inhibiting or pharmacologically blocking:
IL-23 receptor (IL-23R);
IL-23 signalling through IL-23 receptor; or
IL-23 pathway;
for treatment of inflammatory diseases or disorders, which comprises orally administering a pharmaceutical composition, which comprises:
[a] a therapeutically effective amount of a systemically active peptide the Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH₂ (*Pen-Pen form disulfide bond) (SEQ ID NO: 1):

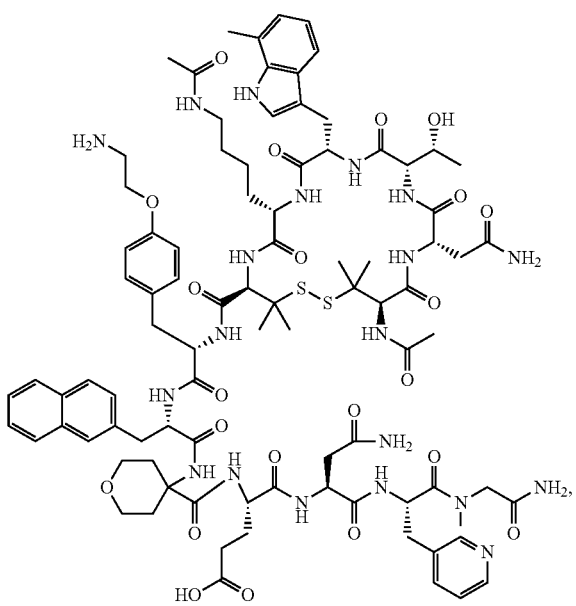 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

or
 a pharmaceutically acceptable salt or solvate form thereof;
 [b] optionally with or without an absorption enhancer; and
 [c] at least one pharmaceutically acceptable excipient;
to a patient in need thereof.

In another aspect, the present invention relates to a method for targeting inhibition or blocking of IL-23 receptor in blood, blood circulation, tissue, skin or joints for treatment of inflammatory diseases or disorders, which comprises administering an oral dose of therapeutically effective amount of a peptide the Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1):

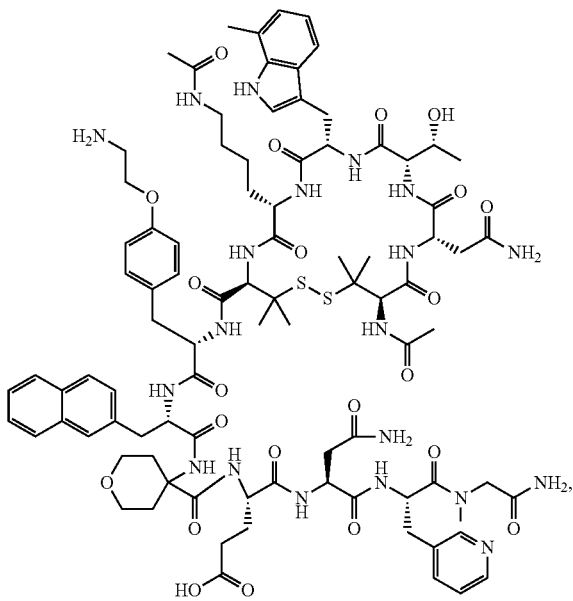 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

or a pharmaceutically acceptable salt or solvate form thereof to a patient in need thereof.

In another aspect, the present invention relates to a method for inhibition or blocking of IL-23 receptor in blood, blood circulation, tissue, skin or joints for treatment of inflammatory diseases or disorders, which comprises administering an oral dose of therapeutically effective amount of a pharmaceutical composition, which comprises:
 [a] a therapeutically effective amount of a systemically active peptide Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1):

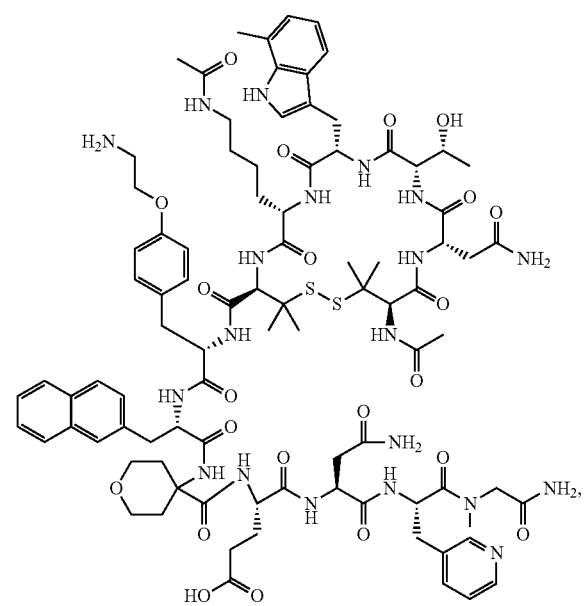 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

or
 a pharmaceutically acceptable salt or solvate form thereof;
 [b] optionally an absorption enhancer; and
 [c] at least one pharmaceutically acceptable excipient;
to a patient in need thereof.

In other aspects, it is understood that methods defined for the present invention, such as those defined herein, which include methods for inhibition or blocking of IL-23 receptor in blood, blood circulation, tissue, skin or joints for treatment of inflammatory diseases or disorders and as otherwise discussed herein are understood to include or encompass or envisage incorporating aspects or embodiments definitions where:
 inhibition or blocking IL-23 receptor (IL-23R) occurs in tissues including and beyond the gastrointestinal tract;
 systemic pharmacodynamic activity in blood is directly proportional to the systemic exposure in human subjects;
 level of target blockade is predicted by IC$_{50}$ value;
 sufficient exposure of the systemically active peptide level is at least above IC$_{50}$ for 24 hours;
 a level of target blockade is determined by IC$_{50}$ values in picomolar range;
 systemic exposure is required for inhibitory activity in the blood; and/or
 pharmacologic activity for a drug in blood, plasma or serum is measured or detected as a function of drug's systemic exposure & potency.

Each of the aspects of the present invention are envisioned to be adapted for inflammatory diseases or disorders selected from psoriasis, psoriatic arthritis, inflammatory bowel disease, ulcerative colitis, Crohn's disease, and/or inflammatory diseases or disorders that are moderate to severe in degree.

In accordance with aspects of the present invention as defined throughout the instant disclosure, the systemically active peptide may be, but is not limited to be administered
- in a dose range from about 1 mg to about 1000 mg;
- in dose range from about 25 mg to about 100 mg;
- in specific doses of 10 mg, 25 mg or 50 mg once daily or twice daily as needed;
- in a dose of 10 mg once daily or 10 mg twice daily;
- in a dose 25 mg once daily or 25 mg twice daily;
- in a dose 50 mg once daily or 50 mg twice daily; and/or
- is dosed 50 mg once or twice daily greater than 50% inhibition over a 24 hour period is observed.

In accordance with aspects of the present invention as defined throughout the instant disclosure, the systemically active peptide may be, but is not limited to be administered
- in specific doses of about 10 mg, about 25 mg or about 50 mg once daily or twice daily as needed;
- in a dose of about 10 mg once daily or about 10 mg twice daily;
- in a dose of about 25 mg once daily or about 25 mg twice daily;

In one aspect, the present invention relates to a method for inhibiting IL-23 receptor in a tissue selected from blood, skin, cartilage, or synovial membrane, which comprises administering an oral dose of a therapeutically effective amount of a peptide Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1); or a pharmaceutically acceptable salt or solvate form thereof to a patient in need thereof.

In one aspect, the present invention relates to tissue that is selected from: blood; skin; cartilage; or synovial membrane, respectively or individually. In some aspects, the present invention relates to tissue that is blood. In some aspects, the present invention relates to tissue that is skin. In some aspects, the present invention relates to tissue that is cartilage. In some aspects, the present invention relates to tissue that is synovial membrane.

In another aspect, the present invention relates to a method for inhibiting IL-23 receptor in a digestive tract tissue, which comprises administering an oral dose of a therapeutically effective amount of a peptide Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1), or a pharmaceutically acceptable salt or solvate form thereof to a patient in need thereof.

In one aspect, the digestive tract tissue is selected from the group consisting of mouth, esophagus, stomach, small intestine, large intestine, duodenum, and anus, collectively, respectively or individually. In some aspects, the digestive tract tissue is mouth. In some aspects, the digestive tract tissue is esophagus. In some aspects, the digestive tract tissue is stomach. In some aspects, the digestive tract tissue is small intestine. In some aspects, the digestive tract tissue is large intestine. In some aspects, the digestive tract tissue is duodenum. In some aspects, the digestive tract tissue is anus.

In one aspect, the present invention relates to a method for inhibiting production of IL-17A in a tissue selected from blood, skin, cartilage, or synovial membrane, which comprises administering an oral dose of a therapeutically effective amount of a peptide Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) or a pharmaceutically acceptable salt or solvate form thereof to a patient in need thereof.

In another aspect, the present invention relates to a method for inhibiting production of IL-17A in a digestive tract tissue, which comprises administering an oral dose of a therapeutically effective amount of a peptide Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) or a pharmaceutically acceptable salt or solvate form thereof to a patient in need thereof.

IL-17A may be measured by any method known in the art, and can include an antibody or antigen-binding biochemical assay, such as an enzyme-linked immunosorbent assay (ELISA) or radiometric assay, and includes the methods described herein, such as those of the Examples.

In some aspects, the method and/or use of the peptide of SEQ ID NO: 1 or pharmaceutically acceptable salt or solvate thereof reduces an IL-17A level in a subject in need thereof. In some aspects, the reduction of IL-17A is measured by comparing an IL-17A level after administration of the peptide of SEQ ID NO: 1 or pharmaceutically acceptable salt or solvate thereof to a control IL-17A level before or without administration. In some aspects, the IL-17A level can be measured in vivo, ex vivo, or in vitro. In some aspects, the IL-17A level is reduced by from about 5% to about 95%, such as from about 10% to about 90%, from about 20% to about 80%, from about 30% to about 80%, or from about 30% to about 70%. For example, the IL-17A level can be reduced by from about 20% to about 80%. In some aspects, the IL-17A level is reduced by about 10%, about 20%, about 30%, about 40%, about 50%, about 60%, about 70%, about 80%, or about 90%.

In one aspect, the present invention relates to a method for inhibiting production of IL-17F in a tissue selected from blood, skin, cartilage, or synovial membrane, which comprises administering an oral dose of a therapeutically effective amount of a peptide Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) or a pharmaceutically acceptable salt or solvate form thereof to a patient in need thereof.

In another aspect, the present invention relates to a method for inhibiting production of IL-17F in a digestive tract tissue, which comprises administering an oral dose of a therapeutically effective amount of a peptide Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) or a pharmaceutically acceptable salt or solvate form thereof to a patient in need thereof.

IL-17F may be measured by any method known in the art, and can include an antibody or antigen-binding biochemical assay, such as an enzyme-linked immunosorbent assay (ELISA) or radiometric assay, and includes the methods described herein, such as those of the Examples.

In some aspects, the method and/or use of the peptide of SEQ ID NO: 1 or pharmaceutically acceptable salt or solvate thereof reduces an IL-17F level in a subject in need thereof. In some aspects, the reduction of IL-17F is measured by comparing an IL-17F level after administration of the peptide of SEQ ID NO: 1 or pharmaceutically acceptable salt or solvate thereof to a control IL-17F level before or without administration. In some aspects, the IL-17F level can be measured in vivo, ex vivo, or in vitro. In some aspects, the IL-17F level is reduced by from about 5% to about 95%, such as from about 10% to about 90%, from about 20% to about 80%, from about 30% to about 80%, or from about 30% to about 70%. For example, the IL-17F level can be reduced by from about 20% to about 80%. In some aspects, the IL-17F level is reduced by about 10%, about 20%, about 30%, about 40%, about 50%, about 60%, about 70%, about 80%, or about 90%.

In one aspect, the present invention relates to a method for inhibiting production of IL-22 in a tissue selected from blood, skin, cartilage, or synovial membrane, which comprises administering an oral dose of a therapeutically effective amount of a peptide Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) or a pharmaceutically acceptable salt or solvate form thereof to a patient in need thereof.

In another aspect, the present invention relates to a method for inhibiting production of IL-22 in a digestive tract tissue, which comprises administering an oral dose of a therapeutically effective amount of a peptide Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) or a pharmaceutically acceptable salt or solvate form thereof to a patient in need thereof.

IL-22 expression may be measured by any method known in the art, and can include an antibody or antigen-binding biochemical assay, such as an enzyme-linked immunosorbent assay (ELISA) or radiometric assay, and includes the methods described herein, such as those of the Examples.

In some aspects, the method and/or use of the peptide of SEQ ID NO: 1 or pharmaceutically acceptable salt or solvate thereof reduces an IL-22 expression level in a subject in need thereof. In some aspects, the reduction of IL-22 expression is measured by comparing an IL-22 expression level after administration of the peptide of SEQ ID NO: 1 or pharmaceutically acceptable salt or solvate thereof to a control IL-22 expression level before or without administration. In some aspects, the IL-22 expression level can be measured in vivo, ex vivo, or in vitro. In some aspects, the IL-22 expression level is reduced by from about 5% to about 95%, such as from about 10% to about 90%, from about 20% to about 80%, from about 30% to about 80%, or from about 30% to about 70%. For example, the IL-22 expression level can be reduced by from about 20% to about 80%. In some aspects, the IL-22 expression level is reduced by about 10%, about 20%, about 30%, about 40%, about 50%, about 60%, about 70%, about 80%, or about 90%.

In other aspects, newly developed for use with the present invention are conventionally known assays, which may include, but are not limited to PD biomarker assays may be used with compounds or pharmaceutically acceptable salts or corresponding pharmaceutical compositions or formulations of the present invention to detect/quantify pharmacologic activity for a drug in blood/plasma/serum which is a function of drug's systemic exposure & potency.

In some aspects, the disease or disorder is autoimmune inflammation and related diseases and disorders, such as, which may include, but are not limited to multiple sclerosis, asthma, rheumatoid arthritis, inflammation of the gut, inflammatory bowel diseases (IBDs), juvenile IBD, adolescent IBD, Crohn's disease, ulcerative colitis, sarcoidosis, Systemic Lupus Erythematosus, ankylosing spondylitis (axial spondyloarthritis), psoriatic arthritis, or psoriasis.

In some aspects, the disease or disorder is or may be selected from psoriasis (e.g., plaque psoriasis, guttate psoriasis, inverse psoriasis, pustular psoriasis, Palmo-Plantar Pustulosis, psoriasis vulgaris, or erythrodermic psoriasis), atopic dermatitis, acne ectopica, ulcerative colitis, Crohn's disease, Celiac disease (nontropical Sprue), enteropathy associated with seronegative arthropathies, microscopic colitis, collagenous colitis, eosinophilic gastroenteritis/esophagitis, colitis associated with radio- or chemo-therapy, colitis associated with disorders of innate immunity as in leukocyte adhesion deficiency-1, chronic granulomatous disease, glycogen storage disease type 1b, Hermansky-Pudlak syndrome, Chediak-Higashi syndrome, Wiskott-Aldrich Syndrome, pouchitis, pouchitis resulting after proctocolectomy and ileoanal anastomosis, gastrointestinal cancer, pancreatitis, insulin-dependent diabetes mellitus, mastitis, cholecystitis, cholangitis, primary biliary cirrhosis, viral-associated enteropathy, pericholangitis, chronic bronchitis, chronic sinusitis, asthma, uveitis, or graft versus host disease.

In one aspect, the present invention relates to methods and/or uses for treatment of autoimmune inflammation and related diseases and disorders, which may include, but is/are not limited to inflammatory bowel disease (IBD), Crohn's disease (CD), ulcerative colitis (UC), psoriasis (PsO), or psoriatic arthritis (PsA) and the like. In some aspects, the inflammatory disease is inflammatory bowel disease (IBD), Crohn's disease, ulcerative colitis, psoriasis, or psoriatic arthritis.

In some aspects, the present invention provides a method or use for treating an inflammatory bowel disease (IBD) in a subject in need thereof, which comprises administering to the subject a composition of the present invention. In some aspects, the present invention provides a method of treating an inflammatory bowel disease (IBD) in a subject including administering to the subject a therapeutically effective amount of a composition of the present invention. In some aspects, the IBD is ulcerative colitis. In some aspects, the IBD is Crohn's disease.

In some aspects, the present invention provides methods or use of compositions of the present invention in the manufacture of a medicament for treating an inflammatory bowel disease (IBD).

In another aspect, the present invention relates to a method of treating an inflammatory bowel disease (IBD) in a subject in need thereof which comprises administering to the subject a therapeutically effective amount of a composition disclosed herein. In some aspects, the IBD is Crohn's disease or ulcerative colitis. In some aspects, the IBD is Crohn's disease. In some aspects, the IBD is ulcerative colitis.

In some aspects, the present invention provides for a use of a composition disclosed herein in the manufacture of a medicament for treating an inflammatory bowel diseases (IBD).

In some aspects, the present invention relates to a method of treating psoriasis or psoriatic arthritis in a subject in need thereof which comprises administering to the subject a therapeutically effective amount of a composition of the present invention.

In some aspects, the present invention provides for a use of a composition disclosed herein, in the manufacture of a medicament for treating psoriasis or psoriatic arthritis.

In some aspects, the present invention relates to methods or uses of treating inflammatory bowel diseases (IBD) in a subject, which comprises administering a therapeutically effective amount of a compositions disclosed herein. In some aspects, the methods or uses of the present invention, which comprises administering compositions in tablet form once, twice, or thrice daily orally in accordance with patient treatment. In some aspects, the IBD is Crohn's disease or ulcerative colitis.

Each aspect of the present invention defined in this or in any other section may incorporate definitions and limitations, such as those set forth in Sections II to VI herein and throughout the originally filed disclosure, specification and claims.

VI. EXAMPLES

In describing the invention, abbreviations and symbols utilized herein are in accordance with the common usage of such abbreviations and symbols by those skilled in the chemical and biological arts. Specifically, the following abbreviations may be used in the examples and throughout the specification:

List of Standard Chemical Definitions

| Acronym or Abbreviation | Definition |
| --- | --- |
| Ac | acetate |
| ACN | Acetonitrile |
| AEF | 4-(2-aminoethoxy)phenylalanine |
| Amu | Atomic Mass Unit(s) |
| Asn, N | L-asparagine |
| BOC | t-Butoxy- |
| DIC | diisopropylcarbodiimide |
| DMF | Dimethyl formamide |
| Glu, E | L-Glutamic Acid |
| FMOC | Fluorenylmethyloxycarbonyl |
| HPLC | High Pressure Liquid Chromatography |
| Lys | L-lysine |
| MBHA | 4-Methylbenzhydrylamine |
| 2-Nal | 2-naphthyl-L-alanine |
| 3-Pal | 3-(3-pyridyl)-L-alanine |
| Pen | penicillamine |
| Phe | L-phenylalanine |
| Sarc | sarcosine |
| tBu | t-butyl |
| TFA | Trifluoroacetic acid |
| THP | 4-amino-tetrahydropyran-4-carboxylic acid |
| TIPS | triisopropylsilane |
| Thr, T | L-threonine |
| Trp, W | L-tryptophan |
| Trt | trityl |

Example 1. Preparation of Amorphous Acetate Form of the Peptide of SEQ ID NO: 1

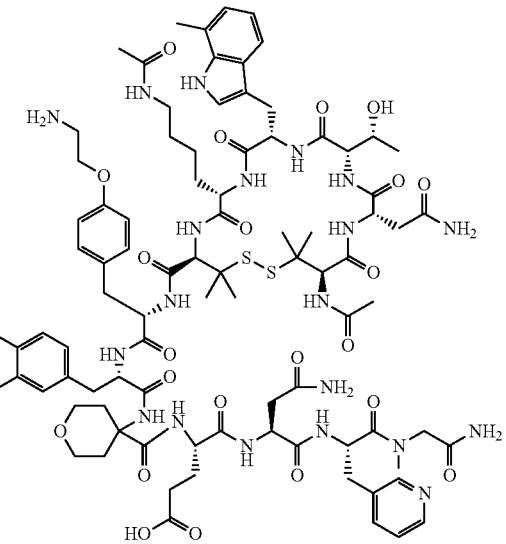

(SEQ ID NO: 1)

Ac-[Pen]*-N-T-[W(7-Me)]-[Lys(Ac)]-[Pen]*-Phe[4-(2-aminoethoxy)]-[2-Nal]-[THP]-E-N-[3-Pal]-Sarc-NH₂ (*Pen-Pen form disulfide bond)

The synthesis of amorphous acetate form of the peptide SEQ ID NO: 1 was prepared using FMOC solid phase peptide synthesis techniques according to Example 1B of US 2021/0261622.

The peptide was constructed on Rink Amide MBHA resin using standard FMOC protection synthesis conditions reported in the literature. The constructed peptide was isolated from the resin and protecting groups by cleavage with strong acid followed by precipitation. Oxidation to form the disulfide bond was performed followed by purification by reverse phase HPLC (RPHPLC) and counterion exchange. Lyophilization of pure fractions gave the final product.

Swell Resin: 10 g of Rink Amide MBHA solid phase resin (0.66 mmol/g loading) was transferred to a 250 ml peptide vessel with filter frit, ground glass joint and vacuum side arm. The resin was washed 3× with DMF.

Step 1: Coupling of FMOC-Sarc-OH: Deprotection of the resin bound FMOC group was realized by adding 2 resin-bed volumes of 20% 4-methyl-piperidine in DMF to the swollen resin and shaking for 3-5 min prior to draining and adding a second, 2-resin-bed volume of the 4-methyl piperidine solution and shaking for an additional 20-30 min. After deprotection the resin was washed 3×DMF with shaking. FMOC-Sarc-OH (3 eq, 6.2 g) was dissolved in 100 ml DMF along with Oxyma (4.5 eq, 4.22 g). Preactivation of the acid was accomplished by addition of DIC (3.9 eq, 4 ml) with shaking for 15 min prior to addition to the deprotected resin. An additional aliquot of DIC (2.6 eq, 2.65 ml) was then added after ~15 min of coupling. The progress of the coupling reaction was monitored by the colorimetric Kaiser test. Once the reaction was judged complete the resin was washed 3×DMF with shaking prior to starting the next deprotection/coupling cycle.

Step 2: Coupling of FMOC-3Pal-OH: FMOC deprotection was again accomplished by adding two sequential, 2-resin-bed volumes of 20% 4-methyl-piperidine in DMF, one times 3-5 minutes and one times 20-30 minutes, draining in between treatments. The resin was then washed 3 times prior to coupling with protected 3-pyridyl alanine (3Pal). FMOC-3Pal-OH (3 eq, 7.8 g) was dissolved in DMF along with Oxyma (4.5 eq, 4.22 g). Preactivation with DIC (3.9 eq, 4 ml) for 15 minutes was done prior to addition to the Sarc-Amide resin. After 15 minutes, an additional aliquot of DIC (2.6 eq, 2.65 ml) was added to the reaction. Once the reaction was complete as determined by the Kaiser test, the resin was again washed 3× with DMF prior to starting the next deprotection/coupling cycle.

Step 3: Coupling of FMOC-Asn(Trt)—OH: The FMOC was removed from the N-terminus of the resin bound 3Pal and washed as previously described. FMOC-Asn(Trt)—OH (2 eq, 8 g) was dissolved in 100 ml of DMF along with Oxyma (3 eq, 2.81 g). DIC (2.6 eq, 2.65 ml) was added for preactivation of the acid for ~15 minutes prior to addition to the 3Pal-Sarc-Amide resin. After ~15 minutes, an additional aliquot of DIC (1.4 eq, 1.43 ml) was added to the reaction. Once the reaction was complete as determined by the Kaiser test, the resin was washed 3× with DMF prior to starting the next deprotection/coupling cycle.

Step 4: Coupling of FMOC-Glu(OtBu)—OH: The FMOC was removed from the N-terminus of the resin bound Asparagine and the resin washed with DMF as previously described. FMOC-Glu(OtBu)—OH (2 eq, 5.91 g) was dissolved in 100 ml of DMF along with Oxyma (3 eq, 2.81 g). DIC (2.6 eq, 2.65 ml) was added for preactivation of the acid ~15 minutes prior to addition to the Asn(Trt)-3Pal-Sarc-Amide resin. After ~15 minutes, an additional aliquot of DIC (1.4 eq, 1.43 ml) was added to the reaction. Once the reaction was complete as determined by the Kaiser test the resin was washed 3× with DMF prior to starting the next deprotection/coupling cycle.

Step 5: Coupling of FMOC-THP-OH: The FMOC was removed from the N-terminus of the resin bound peptide and the resin was washed as previously described. FMOC-THP-OH (3 eq, 7.36 g) was dissolved in 100 ml of DMF along with Oxyma (4.5 eq, 4.22 g). DIC (3.9 eq, 4 ml) was added for preactivation of the acid ~15 minutes prior to addition to the Glu(OtBu)-Asn(Trt)-3Pal-Sarc-Amide resin. After ~15 minutes, an additional aliquot of DIC (2.6 eq, 2.65 ml) was added to the reaction. Once the reaction was complete as determined by the Kaiser test the resin was washed 3× with DMF prior to starting the next deprotection/coupling cycle.

Step 6: Coupling of FMOC-L-Ala(2-Naphthyl)-OH (Nal): The FMOC was removed from the N-terminus of the resin bound peptide and the resin washed as previously described. FMOC-L-Ala(2-Naphthyl)-OH (3 eq, 8.66 g) was dissolved in 100 ml of DMF along with Oxyma (4.5 eq, 4.22 g). DIC (3.9 eq, 4 ml) was added for preactivation of the acid ~15 minutes prior to addition to the THP-Glu(OtBu)-Asn(Trt)-3Pal-Sarc-Amide resin. After ~15 minutes, an additional aliquot of DIC (2.6 eq, 2.65 ml) was added. Once the reaction was complete as determined by the Kaiser test the resin was again washed 3× with DmF prior to starting the next deprotection/coupling cycle.

Step 7: Coupling of FMOC-4-[2-(Boc-amino-ethoxy)]-L-Phenylalanine (FMOC-AEF): The FMOC was removed from the N-terminus of the resin bound peptide and the resin washed as previously described. FMOC-4-[2-(Boc-amino-ethoxy)]-L-Phenylalanine (3 eq, 10.8 g) was dissolved in 100 ml of DMF along with Oxyma (4.5 eq, 4.22 g). DIC (3.9 eq, 4 ml) was added for preactivation of the acid ~15 minutes prior to addition to the Nal-THP-Glu(OtBu)-Asn(Trt)-3Pal-Sarc-Amide resin. After ~15 minutes, an additional aliquot of DIC (2.6 eq, 2.65 ml) was added to the reaction. Once the reaction was complete as determined by the Kaiser test the resin was washed 3× with DmF prior to starting the next deprotection/coupling cycle.

Step 8: Coupling of FMOC-Pen(Trt)—OH: The FMOC was removed from the N-terminus of the resin bound peptide and the resin washed as previously described. FMOC-Pen(Trt)—OH (3 eq, 12.14 g) was dissolved in 100 ml of DMF along with Oxyma (4.5 eq, 4.22 g). DIC (3.9 eq, 4 ml) was added for preactivation of the acid ~15 minutes prior to addition to the AEF-Nal-THP-Glu(OtBu)-Asn(Trt)-3Pal-Sarc-Amide resin. After ~15 minutes, an additional aliquot of DIC (2.6 eq, 2.65 ml) was added to the reaction. Once the reaction was complete as determined by the Kaiser test, the resin was again washed 3× with DMF prior to starting the next deprotection/coupling cycle.

Step 9: Coupling of FMOC-Lys(Ac)—OH: The FMOC was removed from the N-terminus of the resin bound peptide and the resin washed as previously described. FMOC-Lys(Ac)—OH (2 eq, 5.4 g) was dissolved in 100 ml of DMF along with Oxyma (3 eq, 2.81 g). DIC (2.6 eq, 2.65 ml) was added for preactivation of the acid ~15 minutes prior to addition to the Pen(Trt)-AEF-Nal-THP-Glu(OtBu)-Asn(Trt)-3Pal-Sarc-Amide resin. After ~15 minutes, an additional aliquot of DIC (1.4 eq, 1.43 ml) was added to the reaction. Once the reaction was complete as determined by the Kaiser test, the resin was again washed 3× with DMF prior to starting the next deprotection/coupling cycle.

Step 10: Coupling of FMOC-7-Me-Trp-OH: The FMOC was removed from the N-terminus of the resin bound peptide and the resin washed as previously described. FMOC-7-Me-Trp-OH (2 eq, 5.81 g) was dissolved in 100 ml of DMF along with Oxyma (3 eq, 2.81 g). DIC (2.6 eq, 2.65 ml) was added for preactivation of the acid ~15 minutes prior to addition to the Lys(Ac)-Pen(Trt)-AEF-Nal-THP-Glu(OtBu)-Asn(Trt)-3Pal-Sarc-Amide resin. After ~15 minutes, an additional aliquot of DIC (1.4 eq, 1.43 ml) was added to the reaction. Once the reaction was complete as determined by the Kaiser test, the resin was again washed 3× with DMF prior to starting the next deprotection/coupling cycle.

Step 11: Coupling of FMOC-Thr(tBu)—OH: The FMOC was removed from the N-terminus of the resin bound peptide and the resin washed as previously described. FMOC-Thr(tBu)—OH (4 eq, 10.5 g) was dissolved in 100 ml of DMF along with Oxyma (6 eq, 5.62 g). DIC (5.2 eq, 5.3 ml) was added for preactivation of the acid ~15 minutes prior to addition to the 7MeTrp-Lys(Ac)-Pen(Trt)-AEF-Nal-THP-Glu(OtBu)-Asn(Trt)-3Pal-Sarc-Amide resin. After ~15 minutes, an additional aliquot of DIC (2.6 eq, 2.65 ml) was added to the reaction. Once the reaction was complete as determined by the Kaiser test, the resin was again washed 3× with DMF prior to starting the next deprotection/coupling cycle.

Step 12: Coupling of FMOC-Asn(Trt)—OH: The FMOC was removed from the N-terminus of the resin bound peptide and the resin washed as previously described. FMOC-Asn(Trt)—OH (4 eq, 15.8 g) was dissolved in 100 ml of DMF along with Oxyma (6 eq, 5.62 g). DIC (5.2 eq, 5.3 ml) was added for preactivation of the acid ~15 minutes prior to addition to the Thr(tBu)-7MeTrp-Lys(Ac)-Pen(Trt)-AEF-Nal-THP-Glu(OtBu)-Asn(Trt)-3Pal-Sarc-Amide resin. After ~15 minutes, an additional aliquot of DIC (2.6 eq, 2.65 ml) was added to the reaction. Once the reaction was complete as determined by the Kaiser test, the resin was again washed 3× with DMF prior to starting the next deprotection/coupling cycle.

Step 13: Coupling of FMOC-Pen(Trt)—OH: The FMOC was removed from the N-terminus of the resin bound peptide and the resin washed as previously described. FMOC-Pen(Trt)—OH (2 eq, 8.1 g) was dissolved in 100 ml of DMF along with Oxyma (3 eq, 2.81 g). DIC (2.6 eq, 2.65 ml) was added for preactivation of the acid ~15 minutes prior to addition to the Asn(Trt)-Thr(tBu)-7MeTrp-Lys(Ac)-Pen(Trt)-AEF-Nal-THP-Glu(OtBu)-Asn(Trt)-3Pal-Sarc-Amide resin. After ~15 minutes, an additional aliquot of DIC (2.6 eq, 2.65 ml) was added to the reaction. Once the reaction was complete as determined by the Kaiser test, the resin was again washed 3× with DmF prior to the final deprotection and acetic acid capping of the constructed peptide.

Step 14: Acetyl Capping: The FMOC was removed from the N-terminus of the resin bound peptide and the resin washed as previously described. 150 ml of Capping Reagent A (THF/Acetic anhydride/Pyridine, 80:10:10) was added to the constructed Pen(Trt)-Asn(Trt)-Thr(tBu)-7MeTrp-Lys(Ac)-Pen(Trt)-AEF-Nal-THP-Glu(OtBu)-Asn(Trt)-3Pal-Sarc-Amide resin and shaken for 30 min. The resin was washed 3× with DMF followed by 5× with DCM. The resin was divided into 5-50 ml centrifuge tubes and placed under vacuum for 1.5 hrs prior to cleavage with TFA.

Step 15: TFA Cleavage and Ether precipitation: 200 ml of the TFA cleavage cocktail (90/5/2.5/2.5 TFA/water/TIPS/DODT) was prepared. 40 ml of the cleavage cocktail was added to each of the 5 tubes containing the protected resin bound peptide and shaken for two hours. The spent resin was filtered away and the filtrate divided evenly into 18-50 ml centrifuge tubes for precipitation. Cold diethyl ether was added to each forming a white precipitate that was then centrifuged. The ether was decanted to waste and 2 more ether washes of the precipitate were performed. The resulting white precipitate cake was dried overnight in the hood to give the crude reduced peptide.

Step 16: Disulfide Oxidation: The crude peptide was oxidized and purified in four 1 L batches. ~2.5 g of crude peptide was dissolved in 1 L 20% ACN/water. With stirring, a saturated solution of iodine in acetic acid/methanol was added dropwise to the 1 L peptide solution until the yellow/brown color of the 12 remains and does not fade away. The light yellow solution was allowed to sit for 5 min prior to quenching the excess 12 with a pinch of ascorbic acid.

Step 17: RP-HPLC purification: The RP-HPLC purification was performed immediately following each 12 oxidation. A preparative purification column (Phenomenex, Luna, C18(2), 100 Å, 250×50 mm) was equilibrated at 70 ml/min with 20% MPB in MPA (MPA=0.1% TFA/water, MPB=0.1% TFA in ACN). The 1 L of quenched oxidized peptide was loaded onto the equilibrated column at 70 ml/min. After the solvent front elutes, a gradient of 25-45% MPB at 70 ml/min was run over 60 min. The desired material was isolated in fractions and each were analyzed by analytical RPHPLC. Pure fractions were combined from all four purifications and lyophilized to give purified TFA salt ready for counterion exchange.

Step 18: Counterion Exchange to Acetate: The same preparative RP-HPLC column was equilibrated with 5% MPB in MPA at 70 ml/min (MPA=0.3% AcOH in Water, MPB=0.3% AcOH in ACN, MPC=0.5 M $NH_4OAc$ in Water.) The purified peptide TFA salt was dissolved in 50/50 ACN/water and diluted to 15% ACN. The solution was loaded onto the equilibrated column at 70 ml/min and the solvent front was eluted. The captured peptide was washed with 5% MPB in MPA for 5 min. The captured peptide was then washed with 5% MPB in MPC for 40 min at 70 ml/min to exchange the counterions to Acetate counterions. The captured peptide was washed with 5% MPB in MPA at 70 ml/min for 10 min to clear all $NH_4OAc$ from the system. Finally, the peptide was eluted with a gradient of 5-70% MPB in MPA over 60 minutes and collected in fractions.

Step 19: Final Lyophilization and Analysis: The collected fractions were analyzed by analytical RP-HPLC, and all fractions >95% purity were combined. Lyophilization of the combined fractions gave SEQ ID NO: 1 as a white powder with a purity >95% as determined by RP-HPLC. Peptide identity was confirmed with LC/MS of the purified amorphous acetate form of the Peptide of SEQ ID NO: 1, giving 2 charged states of the peptide, $M^+2/2$ of 950 amu and the molecular ion of 1899 amu. An x-ray powder diffraction spectrum demonstrated the amorphous nature of the product (FIG. 1).

Example 2. Phosphate Buffered Composition Use

The acetate form of the peptide of SEQ ID NO: 1 is taken up in 50 mM sodium phosphate buffer to a concentration for delivery to a subject in a range from 0.33 mg/mL to 33 mg/mL. The resultant solution can be stored at 2-8° C. for up to 4 weeks.

Example 3. Tablet Composition Acetate Form of Peptide of SEQ ID NO: 1

A tablet composition including SEQ ID NO: 1 was prepared as described below.

TABLE 1

Tablet Composition

| Ingredients | Weight % (w/w) | Weight (mg) |
|---|---|---|
| Internal Phase | | |
| Acetate Form of SEQ ID NO: 1 | 1.79 | 25.0 |
| Sodium Caprate | 35.71 | 500.0 |
| Avicel PH101 | 3.93 | 55.0 |
| Sorbitol | 10.71 | 150.0 |
| Croscarmellose sodium | 5.00 | 70.0 |
| Aerosil 200 | 0.50 | 7.0 |
| External Phase | | |
| SMCC HD90 | 36.61 | 512.5 |
| Croscarmellose Sodium | 5.00 | 70.0 |
| Aerosil | 0.50 | 7.0 |
| Magnesium stearate | 0.25 | 3.5 |
| Total | 100% | 1400.0 |

The internal phase included the acetate form of peptide of SEQ ID NO: 1 along with absorption enhancer sodium caprate. Prior to mixing the ingredients of the internal phase, the peptide and the sodium caprate were granulated together to place them in very close proximity and to provide the mixture of these two reagents as discrete granules. The remaining ingredients of the internal phase were then added. Next, the external phase, which was itself generated as a co-granule, was all pressed together with the internal phase to form the core of a tablet. Without being bound by theory, the external phase is believed to be a barrier that prevents sodium caprate from migrating to the eventual pH sensitive outer enteric coating. Accordingly, the external phase is believed to improve the stability of the tablet by protecting the pH sensitive outer enteric coating by physical separation from sodium caprate.

The above combined internal and external phases of Table 1 making up the tablet core were subsequently coated with a subcoating of 3% (w/w) Opadry QX pink. A functional coating of 12% (w/w, based on core weight of internal plus external phase weight) Acryl-eze® white, delayed release enteric coating (pH 5.5) was then added over the subcoating.

Example 4. Tablet Composition Acetate Form of Peptide of SEQ ID NO: 1

Another tablet composition including acetate form of peptide of SEQ ID NO: 1 was prepared by a similar procedure. This tablet includes magnesium stearate in both the internal and external phases.

TABLE 2

| Tablet Composition | | |
|---|---|---|
| Ingredients | Weight % (w/w) | Weight (mg) |
| Internal Phase | | |
| Acetate Form of SEQ ID NO: 1 | 7.1 | 100.0 |
| Sodium Caprate | 35.71 | 500.0 |
| Avicel PH101 | 3.93 | 55.0 |
| Sorbitol | 10.71 | 150.0 |
| Croscarmellose sodium | 5.00 | 70.0 |
| Aerosil 200 | 0.50 | 7.0 |
| Magnesium stearate | 0.25 | 3.5 |
| External Phase | | |
| SMCC HD90 | 30.75 | 430.5 |
| Croscarmellose Sodium | 5.00 | 70.0 |
| Aerosil | 0.50 | 7.0 |
| Magnesium stearate | 0.5 | 7.0 |
| Total | 100% | 1400.0 |

Example 5. Tablet Composition Acetate Form of Peptide of SEQ ID NO: 1

Another tablet composition including acetate form of peptide of SEQ ID NO: 1 was prepared as described below in a single phase rather than with the internal and external phases.

TABLE 3

| Tablet Composition | | |
|---|---|---|
| Ingredients | Weight % (w/w) | Weight (mg) |
| Acetate Form of SEQ ID NO: 1 | 16.3 | 32.6 |
| Sodium Caprate | 50.0 | 100.0 |
| Kolliphor P188 | 6.0 | 12.0 |
| Pearlitol | 15.2 | 30.4 |
| Vivasol GF | 10.0 | 20.0 |
| Aerosil 200 | 1.0 | 2.0 |
| Magnesium stearate | 1.5 | 3.0 |
| Total | 100% | 200.0 |

The tablet includes the acetate form of peptide of SEQ ID NO: 1 along with absorption enhancer sodium caprate. The peptide, the sodium caprate and remaining ingredients were mixed together into a blend. The blend was pressed to form the core tablet.

The above combined internal and external phases of Table 3 making up the tablet core were subsequently coated with a subcoating of ~3% (w/w) Opadry white. A functional coating of ~4% (w/w, based on core weight of internal plus external phase weight) Acryl-eze®, delayed release enteric coating (pH 5.5) was then added over the subcoating.

Example 6. Tablet Composition of the Acetate Form of the Peptide of SEQ ID NO: 1 with Enhancer A tablet composition including the acetate form of SEQ ID NO: 1 with sodium caprate was prepared by a similar procedure as Example 2.

TABLE 4

| Tablet Composition | | |
|---|---|---|
| Ingredients | Weight % (w/w) | Weight (mg) |
| Internal phase | | |
| Acetate Form of SEQ ID NO: 1 | 1.8 | 25.00 |
| Sodium caprate | 35.7 | 500.00 |
| Cellulose, microcrystalline | 3.9 | 55.00 |
| Sorbitol | 10.7 | 150.00 |
| Croscarmellose sodium | 5.0 | 70.00 |
| Silica, colloidal anhydrous | 0.5 | 7.00 |
| External Phase: | | |
| Silicified microcrystalline cellulose | 36.6 | 512.50 |
| Croscarmellose sodium | 5.0 | 70.00 |
| Silica, colloidal anhydrous | 0.5 | 7.00 |
| Magnesium stearate | 0.25 | 3.50 |
| Total: | 100% | 1400.00 |

The above combined internal and external phases of Table 4 making up the tablet core were subsequently coated with a subcoating of 3% (w/w) Opadry QX pink. A functional coating of 12% (w/w, based on core weight of internal plus external phase weight) Acryl-eze® white, delayed release enteric coating was then added over the subcoating.

Example 7. Tablet Composition of the Acetate Form of the Peptide of SEQ ID NO: 1 with Enhancer A tablet composition including the acetate form of SEQ ID NO: 1 with sodium caprate was prepared by a similar procedure.

TABLE 5

| Tablet Composition | | |
|---|---|---|
| Ingredients | Weight % (w/w) | Weight (mg) |
| Internal phase | | |
| Acetate Form of SEQ ID NO: 1 | 7.1 | 100.00 |
| Sodium caprate | 35.7 | 500.00 |
| Cellulose, microcrystalline | 3.9 | 55.00 |
| Sorbitol | 10.7 | 150.00 |
| Croscarmellose sodium | 5 | 70.00 |
| Silica, colloidal anhydrous | 0.5 | 7.00 |
| Magnesium stearate | 0.25 | 3.50 |
| External Phase: | | |
| Silicified microcrystalline cellulose | 31.0 | 434.00 |
| Croscarmellose sodium | 5 | 70.00 |
| Silica, colloidal anhydrous | 0.5 | 7.00 |
| Magnesium stearate | 0.25 | 3.50 |
| Total: | 100% | 1400.00 |

The above combined internal and external phases of Table 5 making up the tablet core were subsequently coated with a subcoating of 3% (w/w) Opadry QX pink. A functional coating of 12% (w/w, based on core weight of internal plus external phase weight) Acryl-eze® white, delayed release enteric coating was then added over the subcoating.

Example 8. Tablet Composition of the Acetate Form of Peptide of SEQ ID NO: 1 with Enhancer A tablet composition including the acetate form of SEQ ID NO: 1 with sodium caprate was prepared by a similar procedure.

TABLE 6

Tablet Composition

| Ingredients | Weight % (w/w) | Weight (mg) |
|---|---|---|
| Internal phase | | |
| Acetate Form of SEQ ID NO: 1 | 10.7 | 150.00 |
| Sodium caprate | 35.7 | 500.00 |
| Cellulose, microcrystalline | 3.9 | 55.00 |
| Sorbitol | 10.7 | 150.00 |
| Croscarmellose sodium | 5 | 70.00 |
| Silica, colloidal anhydrous | 0.5 | 7.00 |
| External Phase: | | |
| Silicified microcrystalline cellulose | 27.7 | 387.50 |
| Croscarmellose sodium | 5 | 70.00 |
| Silica, colloidal anhydrous | 0.5 | 7.00 |
| Magnesium stearate | 0.25 | 3.50 |
| Total: | 100% | 1400.00 |

Example 9. Tablet Composition of the Acetate Form of Peptide of SEQ ID NO: 1 without Enhancer A tablet composition including the acetate form of SEQ ID NO: 1 with sodium caprate was prepared by a similar procedure.

TABLE 7

Tablet Composition

| Ingredients | Weight % (w/w) | Weight (mg) |
|---|---|---|
| Internal phase | | |
| Acetate Form of SEQ ID NO: 1 | 1.8 | 25.00 |
| Cellulose, microcrystalline | 21.3 | 300.00 |
| Sorbitol | 10.7 | 150.00 |
| Croscarmellose sodium | 2.5 | 35.00 |
| Silica, colloidal anhydrous | 0.5 | 7.00 |
| Magnesium stearate | 0.25 | 3.5 |
| External Phase: | | |
| Silicified microcrystalline cellulose | 59.6 | 834.00 |
| Croscarmellose sodium | 2.5 | 35.00 |
| Silica, colloidal anhydrous | 0.5 | 7.00 |
| Magnesium stearate | 0.25 | 3.50 |
| Total: | 100% | 1400.00 |

The above combined internal and external phases of Table 7 making up the tablet core were subsequently coated with a subcoating of 3% (w/w) Opadry QX pink. A functional coating of 12% (w/w, based on core weight of internal plus external phase weight) Acryl-eze® white, delayed release enteric coating was then added over the subcoating.

Example 10. Solubility of the Acetate Form of the Peptide of SEQ ID NO: 1

An acetate form of SEQ ID NO: 1 prepared according to Example 1 was evaluated for solubility under various conditions. The results are shown in Table 8.

TABLE 8

Solubility of Acetate Form of SEQ ID NO: 1

| Medium | Acetate Form of SEQ ID NO: 1 (g/100 mL) |
|---|---|
| 0.1 N HCl | 78 |
| 0.01 N HCl | 9.5 |
| Citrate buffer pH 2 | 27 |
| Citrate buffer pH 5 | 0.69 |
| phosphate buffer pH 7 | 0.75 |
| Borate buffer pH 9 | >22 |
| Phosphate buffer pH 12 | >44 |
| 0.1 N NaOH | >87 |
| Water | 3.5 |

Example 11. Stability of a Tablet Composition of the Acetate Form of the Peptide of SEQ ID NO: 1

A tablet composition including the acetate form of SEQ ID NO: 1 was evaluated under stress testing conditions.

Example 12. Rat PK Study 1

In this Example, a screen of various absorption enhancers was assessed. Dosing of absorption enhancer was carried out at a fixed concentration of 100 mg/Kg, in combination with the acetate form of peptide of SEQ ID NO: 1 (dosed at 10 mg/Kg) was assessed. A solution of the acetate form of the peptide of SEQ ID NO: 1 was formulated with the same vehicle but without an absorption enhancer (sodium caprate) included as control. The following absorption enhancers were tested: sodium caprate (NaCl0), sodium salcaprozate (SNAC), sucrose laureate, Peptelligence (proprietary technology from Enteris Pharma-undisclosed composition) and Labrasol. The solutions were dosed by intracolonic (IC) or intraduodenal (ID) injection to rats. Results: All absorption enhancers tested increased the oral bioavailability of the acetate form of the peptide of SEQ ID NO: 1, both after IC and ID dosing. NaCl0 gave the highest systemic exposure followed by Peptelligence, then Labrasol, then SNAC, and finally sucrose laureate. Accordingly, sodium caprate was determined to be a preferred absorption enhancer. The observed plasma concentrations in rat exceeded the $IC_{50}$ values presented in Table 14 (0.054-0.5 nM, or 0.10-0.47 ng/mL). Therefore, the systemic exposure is likely to be high enough to afford systemic activity.

The pharmacokinetics of the peptide of SEQ ID NO: 1 was investigated in fasted male Sprague Dawley rats (n=3 in each group) following single intraduodenal (ID) and intracolonic (IC) administration of a 50 mM PBS solution (pH 7.4) containing SEQ ID NO: 1, at a dose of 10 mg/kg, without and with high doses of different absorption enhancers. The following absorption enhancers were evaluated: sodium caprate (NaCl0, 100 mg/kg), SNAC (100 mg/kg), sucrose laurate (100 mg/kg), Enteris A (proprietary technology of Enteris Pharma) (60 mg/kg), and Labrasol (100 mg/kg). Additional experimental details and a comparison of the actual mean plasma pharmacokinetics parameters of SEQ ID NO: 1 for the reference formulation (without absorption enhancer) and the compositions containing five different absorption enhancers, after ID and IC administration, are displayed in Table 9.

TABLE 9

SEQ ID NO: 1 Plasma Concentration with Absorption Enhancer in Rats

| Absorption enhancer | None | NaC10 | SNAC | Sucrose laurate | Enteris A | Labrasol |
|---|---|---|---|---|---|---|
| Absorption enhancer Dose (mg/kg) | None | 100 | 100 | 100 | 60 | 100 |
| PK parameters after ID dose | | | | | | |
| $C_{max}$ (ng/mL) | 23.1 | 1225 | 209 | 107 | 988 | 625 |
| $t_{max}$ (h) | 0.667 | 0.250 | 0.250 | 0.250 | 0.250 | 0.250 |
| $AUC_{inf}$ (h · ng/mL) | 68.6 | 1188 | 215 | 145 | 964 | 621 |
| $AUC_{last}$ (h · ng/mL)$^a$ | 62.0 | 1186 | 210 | 141 | 958 | 617 |
| $F_{abs}$ (%) | 0.360 | 6.24 | 1.13 | 0.764 | 5.06 | 3.26 |
| PK parameters after IC dose | | | | | | |
| $C_{max}$ (ng/mL) | 4.99 | 1031 | 309 | 191 | 626 | 976 |
| $t_{max}$ (h) | 0.583 | 0.333 | 0.333 | 0.250 | 0.250 | 0.250 |
| $AUC_{inf}$ (h · ng/mL) | N/A | 1210 | 312 | 179 | 567 | 1108 |
| $AUC_{last}$ (h · ng/mL)$^a$ | N/A | 1208 | 309 | 176 | 561 | 1105 |
| $F_{abs}$ (%) | 0.0531 | 6.36 | 1.64 | 0.939 | 2.98 | 5.82 |

$^a$Last time point for $AUC_{last}$: 2, 4, 6, 8, or 24 hours

Example 13. Rat PK Study 2

In this example, the effect of the concentration of NaC10 was studied. Solutions of the acetate form of SEQ ID NO: 1 (10 mg/Kg) in combination with various concentrations of NaC10 (20 mg/Kg, 50 mg/Kg and 200 mg/Kg) were dosed by IC injection to rats. Results: NaC10 increased systemic exposure of the acetate form of peptide of SEQ ID NO: 1 at all concentrations tested, however the increase given by NaC10 dosed at 20 mg/Kg was minimal. The highest absorption enhancement was seen with a concentration of NaC10 of 50 mg/Kg. Increasing the amount of NaC10 to 100 mg/Kg or 200 mg/Kg did not further increase oral bioavailability of the peptide.

Example 14. Dog PK Study

This Example shows the ability of a composition that includes NaC10 at the dose of 50 mg/Kg to increase systemic exposure of the acetate form of peptide of SEQ ID NO: 1. Tablets containing the acetate form of the peptide of SEQ ID NO: 1 (10 mg/Kg) and NaC10 (50 mg/Kg) and other inert excipients were manufactured. Poloxamer P188 was also assessed, in combination with NaC10 with the aim of determining potential synergism. In order to ensure proximity of the peptide and absorption enhancer, they were co-processed by dry granulation as described in Example 2, above. The tablet cores were film-coated with an immediate release protective layer of a PVA-based polymer. An additional coating with a pH-responsive polymer soluble at pH values greater than 5.5 (Acryl-EZE) or 7.0 (HPMC-AS) was also applied. Control tablet cores (immediate-release) without the absorption enhancers were also manufactured and dosed as control in the study. Results: NaC10 increased systemic exposure of the acetate form of the peptide of SEQ ID NO: 1 in all tablets. Tablets containing NaC10 and coated with Acryl-Eze (pH 5.5) gave the highest bioavailability of the peptide and was greater than DR pH 7.0, which was in turn greater than IR. No additional value by addition of P188 was observed.

Plasma PK of SEQ ID NO: 1 was investigated in fasted male dog after single PO administration of a tablet containing 100 mg of the acetate form of SEQ ID NO: 1, without (uncoated and film-coated) and with (film-coated only) absorption enhancer. The ratio of SEQ ID NO: 1 to absorption enhancer was 1:5 (w:w). Two different functional DR film-coatings were investigated that secured safe passage through the stomach, one preventing disintegration below pH 5.5 (inducing dissolution in the upper part of the GI, for example, ileum) and one below pH 7.0 (inducing dissolution in the lower part of the GI, such as the colon).

Illustrative results from the dog PK study are shown in Table 10 below. The 100-mg DR tablets with sodium caprate exhibited higher $C_{max}$ and AUC after administration in dogs as compared to either the 100-mg tablets without sodium caprate or the 10 mg/kg solution. The 100 mg DR tablets with sodium caprate achieved an oral bioavailability of approximately 6%, a 14-fold improvement compared to the uncoated IR tablet. Dogs were administered the SEQ ID NO:1 composition in a fasted condition: 10 min after dosing, 20 mL of a 0.1 M HCl/KCl buffer pH 1.4 was administered by gavage. Following dosing of tablets, 10 mL additional water was given. The normal dry diet was returned 2 hours post-dose.

TABLE 10

Pharmacokinetic Parameters from Single Dose Dog Study

| SEQ ID NO: 1 composition | $C_{max}$ (ng/mL) | $T_{max}$ (h) | $AUC_{last}$ (ng*h/mL) |
|---|---|---|---|
| 10 mg/kg oral solution | 169 | 0.7 | 581 |
| 100 mg uncoated IR tablet | 113 | 1.7 | 491 |
| 100 mg SEQ ID NO: 1 + 500 mg NaC10 uncoated IR tablet | 518 | 1.3 | 1840 |
| 100 mg SEQ ID NO: 1 + 500 mg NaC10 pH 5.5 coated DR tablet | 2180 | 2.7 | 6790 |
| 100 mg SEQ ID NO: 1 + 500 mg NaC10 + 40 mg P188 pH 5.5 coated DR tablet | 1400 | 4.3 | 4290 |

TABLE 10-continued

Pharmacokinetic Parameters from Single Dose Dog Study

| SEQ ID NO: 1 composition | $C_{max}$ (ng/mL) | $T_{max}$ (h) | $AUC_{last}$ (ng*h/mL) |
|---|---|---|---|
| 100 mg SEQ ID NO: 1 + 500 mg NaC10 pH 7.0 coated DR tablet | 414 | 4.0 | 2040 |

IR—immediate release tablets;
DR—delayed release tablets;
1400 mg tablet core.

Example 15. Dog PK Study #2

The pharmacokinetics of the peptide of SEQ ID NO: 1 was investigated in fasted and fed male dogs after a single oral administration of one DR film-coated tablet (with dissolution at pH 5.5 and above) containing 25 mg of the acetate form of SEQ ID NO: 1, with and without 500 mg NaC10. A cross-over design, with at least one week wash-out between two consecutive treatments, was applied to twelve dogs: (1) fasted, without NaC10; (2) fed, without NaC10; (3) fasted, with NaC10, and (4) fed, with NaC10. For fasted dogs: 10 min after dosing, dogs received 20 mL of a 0.1 M HCl/KCl buffer pH 1.4 to mimic human stomach and intestinal pH; following dosing of tablet, 10 mL additional water was given. The normal dry diet was returned 4 hours post-dose. For fed dogs: 20 min before dosing the tablet, dogs received 200 mL of standard liquid meal by gavage. Dogs did not receive any additional food for the remainder of the day. Actual mean plasma PK parameters for the treatments are displayed in Table 11.

TABLE 11

Pharmacokinetic Parameters from Fasted and Fed Dog Study

| Group | PK parameters | | | |
|---|---|---|---|---|
| | $C_{max}$ (ng/mL) | $T_{max}$ (h)[a] | $AUC_{last}$ (ng.h/mL) | $AUC_{inf}$ (ng.h/mL) |
| 25 mg SEQ ID NO: 1 (fasted) | 8.48 | 3.0 | 39.2 | NC |
| 25 mg SEQ ID NO: 1 (fed) | 24.9[a] | 6.8 | 159[a] | 184[a] |
| 25 mg SEQ ID NO: 1 + 500 mg NaC10 (fasted) | 636 | 3.3 | 1940 | 1950 |
| 25 mg SEQ ID NO: 1 + 500 mg NaC10 (fed) | 466 | 6.0 | 2120 | 2170 |

[a]Data was highly variable.

Example 16. Dose-Dependent Rat Blood Activity of the Peptide of SEQ ID NO: 1

A rat whole blood assay was used to evaluate the systemic pharmacologic activity of the orally administered peptide of SEQ ID NO: 1. After oral dosing Sprague-Dawley rats with the peptide of SEQ ID NO: 1, blood was drawn from the rats and stimulated ex-vivo with rat IL-23 plus IL-1β. An ELISA assay was used to measure the presence of IL-17A. The production of IL-17A is expected to be suppressed if IL-23 is inhibited. This assay confirms that systemic exposure of orally dosed peptide of SEQ ID NO: 1 is associated with systemic activity, as measured by lower IL-17A production. The study design is summarized in Table 12.

TABLE 12

Rat Study Design

| Experiment | Test Article | Dose (mg/kg) | Collection time | IL-23 stimulation (ng/mL)* |
|---|---|---|---|---|
| #1 | Vehicle (water) | 5 mL/kg | 2 hr | 4, 20 |
| | Peptide of SEQ ID NO: 1 | 10 | | |
| | | 30 | | |
| | | 100 | | |
| #2 | Vehicle (water) | 5 mL/kg | 2 hr | 4, 20 |
| | Peptide of SEQ ID NO: 1 | 0.03 | | |
| | | 0.1 | | |
| | | 0.3 | | |
| | | 1 | | |
| | | 3 | | |
| | | 10 | | |
| | | 30 | | |
| #3 | Vehicle (water) | 5 mL/kg | 2 hr | 4, 20, 100 |
| | Peptide of SEQ ID NO: 1 | 0.3 | | |
| | | 3 | | |
| | | 30 | | |
| #4 | Vehicle (water) | 5 mL/kg | 2 hr | 4, 20, 100 |
| | | | 6 hr | |
| | Peptide of SEQ ID NO: 1 | 10 | 2 hr | |
| | | | 6 hr | |
| #5 | Vehicle (water) | 5 mL/kg | 2 hr | 4, 20, 100 |
| | Peptide ofSEQ ID NO: 1 | 10 | | |

*IL-23 concentration plus 4 ng/mL IL-1β.

Materials

Materials and kits used in the experiments are summarized in Table 13 below.

TABLE 13

Materials for Rat Study

| Kit | Description | Catalog | Vendor |
|---|---|---|---|
| Rat IL-17A ELISA kit | 96-well plate format assay for quantitative measurement of rat IL-17A protein | ab214028 | abcam |

| Chemicals/Consumables | Description | Catalog | Source |
|---|---|---|---|
| RPMI-1640 with L-glutamine and HEPES | Assay medium | SH30255.01 | HyClone |
| Recombinant rat IL-23 | Cytokine | 3136-RL | R&D Systems |
| Recombinant rat IL-1β | Cytokine | 501-RL-010/CF | R&D Systems |

Methods

In each experiment, groups of 5 or 6 female Sprague-Dawley rats were dosed with an aqueous solution of the peptide of SEQ ID NO: 1 or vehicle (water) by body weight as outlined in Table 12. Two or six hours after dosing, animals were euthanized and blood collected as described based on the following.

Rats were first euthanized by $CO_2$ asphyxiation, then whole blood collected by closed cardiac puncture into individual heparinized vacutainer tubes and kept at room temperature. For in vitro assessment of peptide activity in whole blood from naïve or vehicle-dosed rats, individual or pooled blood samples were diluted with pre-warmed RPMI-1640 (with glutamine and HEPES) at a ratio of one part blood to four parts medium. The diluted blood was mixed by pipetting and kept at room temperature while the peptide of SEQ ID NO: 1 and DMSO were dispensed into 96-well, round-bottom plates using the Tecan D300e. The blood was mixed again and 240 μL per well was pipetted into the peptide-spotted assay plates. The assay plates were incubated at 37° C. in 5% $CO_2$ for 30-60 minutes, followed by IL-23 and IL-1β stimulation as described below.

For determination of peptide concentration, an aliquot of blood from peptide-treated rats was deposited into $K_2EDTA$ microtainer tubes and processed to plasma by centrifugation at 16,100×g for 5 minutes. Plasma was deposited into 5% volume of protease inhibitor (1 cocktail tablet dissolved in 2 mL PBS without $Ca^{++}$ and $Mg^{++}$) and stored at −80° C. for bioanalysis of test article by LCMS. The remainder of each blood sample was separately diluted in pre-warmed RPMI-1640 (with glutamine and HEPES) at a ratio of one part blood to four parts medium. The diluted blood was mixed by pipetting and kept at room temperature while working stocks of rat IL-23 and IL-1β were prepared in RPMI-1640. The blood was mixed again and 240 μL was pipetted per well into 96-well, round-bottom assay plates, followed by IL-23 and IL-1β stimulation as described below.

IL-23 and IL-1β Stimulation

A total of 10 μL of medium supplemented with IL-23 and IL-1β or IL-1β alone was added to each well of diluted blood such that the final concentration of IL-23 was 100, 20, or 4 ng/mL and the final concentration of IL-1β was 4 ng/mL. The assay plates were incubated at 37° C. in 5% $CO_2$. After ~24 hours, the assay plates were centrifuged at 1,300 rpm for 6 minutes at room temperature, and at least 100 μL of cell culture supernatant were collected into 96-well, V-bottom plates. The plates containing supernatants were sealed and placed on ice for immediate measurement of IL-17A or frozen at −80° C.

ELISA for Measurement of Secreted IL-17A

To measure IL-17A in cell culture supernatants, the thawed supernatants were centrifuged at 1,300 rpm for 10 minutes at 4° C. A total of 20 μL of cell culture supernatant was mixed with 80 μL of NS buffer (provided with the rat IL-17A ELISA kit). The diluted samples as well as a freshly prepared serial titration of rat IL-17A (for standard curve) were combined with affinity tag labeled capture and reporter conjugated detector antibodies in 96-well plates (provided with the rat IL-17A ELISA kit). Following a 1-hour incubation at room temperature with shaking, each well was washed 3 times with 350 μL/well wash buffer. After the final wash, the plates were inverted and blotted to remove excess liquid. The plates were developed with TMB substrate for 10 minutes, protected from light, with shaking. After stopping the colorimetric reaction, the absorbance in individual wells was read at 450 nm using a SpectraMax 340PC plate reader.

Data Analysis

A standard curve was generated in duplicate for each ELISA plate. The standard curve data were analyzed with a four-parameter curve fit with $1/y^2$ weighting using SoftMax Pro software. Supernatant IL-17A levels were interpolated or extrapolated from plate-specific standard curves using non-background subtracted optical density at 450 nm (OD450) values in SoftMax Pro and corrected for the dilution factor used in the ELISA assay in Microsoft Excel.

In experiments in which blood was treated with a serial titration of the peptide of SEQ ID NO: 1 in vitro, (Example 17) dilution-adjusted IL-17A levels were plotted versus log-transformed peptide concentration, and the in vitro $IC_{50}$ value was calculated in GraphPad Prism using nonlinear regression (curve fit)— log[inhibitor] vs response (three-parameters)—least squares regression. To estimate the ex vivo $IC_{50}$ value for orally dosed peptide of SEQ ID NO: 1, IL-17A levels were plotted versus log-transformed plasma peptide levels for individual (dosed) animals. The ex vivo $IC_{50}$ value was calculated in GraphPad Prism using nonlinear regression (curve fit)— log[inhibitor] vs response (four-parameters)—robust regression. The top of each ex vivo exposure inhibition curve was constrained to the median IL-17A level detected in IL-23/IL-1β-stimulated blood from control (vehicle-dosed) animals.

For comparative statistics, the arithmetic means of technical replicates were first log-transformed to offset heteroscedasticity and analyzed using a one-way ANOVA. Post-hoc statistical tests were adjusted using either Dunnett's multiple comparisons to compare each dose group to the vehicle or Sidak's multiple comparisons for selected comparisons with a statistically significant p-value threshold of $p<0.05$.

Results Systemic Activity of Orally Dosed Peptide of SEQ ID NO: 1 in Rats

The systemic activity of the orally dosed peptide of SEQ ID NO: 1 was tested in 5 independent experiments as outlined in Table 12 above. These experiments were used to determine dose and exposure response relationships of the peptide of SEQ ID NO: 1 in ex vivo whole blood at $C_{max}$, as well as to evaluate if there was evidence of prolonged pharmacodynamic effect after peptide of SEQ ID NO: 1 exposure decreased in vivo.

Dose Response

The ex vivo dose response profile was fully defined by combining data from all 5 experiments, using blood collected 2 hours after dosing, the time at which the orally dosed peptide of SEQ ID NO: 1 reaches maximal plasma concentrations in rats, and stimulated with 4, 20, or 100 ng/mL IL-23 plus 4 ng/mL of IL-1β or with 4 ng/mL IL-1β alone. Cell culture supernatants were collected ~24 hours later for measurement of secreted IL-17A by ELISA.

The peptide of SEQ ID NO: 1 (0.03-100 mg/kg, p.o.) demonstrated dose-dependent inhibition of IL-23 and IL-1β-induced IL-17A secretion in whole blood, with limited effect at doses of 1 mg/kg or lower and complete or nearly complete inhibition achieved at doses of 30 and 100 mg/kg (FIGS. 2-5). Technical replicates were averaged by arithmetic mean. Error bars were omitted for clarity. Data from five different experiments (three experiments for 100 ng/mL IL-23 condition) were combined (box at interquartile range, bars at minima/maxima). One-way ANOVA on log-normalized values with Dunnett's post-tests comparing each treatment to vehicle (ns=not significant, * $p<0.05$,  $p<0.01$, ** $p<0.0001$).

Figure 5:
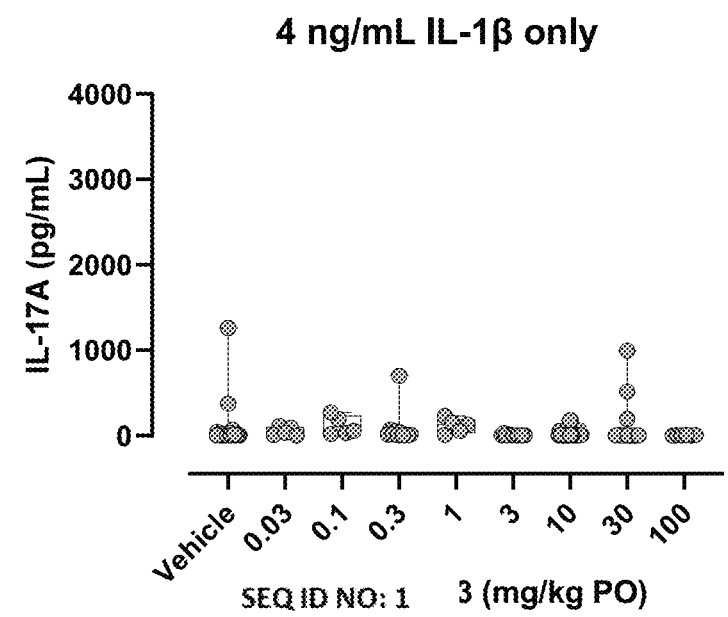
FIG. 5 shows a graph of interleukin-17A levels in rat blood vs. oral doses of the peptide of SEQ ID NO: 1 at (0.03-100 mg/kg, p.o.), following stimulation of the rat blood with 4 ng/mL IL-1β.

The dilution-adjusted ex vivo $IC_{50}$ value for the orally administered peptide of SEQ ID NO: 1 was 0.032 nM in blood challenged with 4 ng/mL IL-23 and 0.27 nM in blood challenged with 20 ng/mL IL-23 (FIG. 5).

Thus, the exposure-dependent ex vivo inhibition of IL-17A production by the orally dosed peptide of SEQ ID NO: 1 was more potent when whole blood was stimulated with lower concentrations of IL-23, consistent with the peptide of SEQ ID NO: 1 acting as a competitive antagonist of IL-23R.

Example 17. Comparison of $IC_{50}$ Values of the Peptide of SEQ ID NO: 1 in Rat Blood Treated In-Vitro, with $IC_{50}$ Values from Rat Blood Collected Ex-Vivo after Oral Administration If the orally administered peptide of SEQ ID NO: 1 has dose-dependent systemic exposure in rat blood, then we predicted that the $IC_{50}$ for inhibition of ex vivo IL-23-stimulated IL-17A of the peptide of SEQ ID NO: 1, as generated from the exposure-dependent inhibition measured in blood from orally dosed rats, will be consistent with the $IC_{50}$ of blood taken from an un-dosed rat wherein the removed blood was treated subsequently with the peptide of SEQ ID NO: 1.

The in vitro potency of the peptide of SEQ ID NO: 1 was determined by treating pooled blood samples from 6 naïve rats or individual blood samples from vehicle-dosed rats with a serial titration of peptide prior to stimulation with IL-23 and IL-1β. The absolute amount of IL-17A produced by whole blood from individual animals ranged from 536.0 to 2429 pg/mL when stimulated with 20 ng/mL IL-23 and 409.4 to 2196 pg/mL when stimulated with 4 ng/mL IL-23. The in vitro $IC_{50}$ values for the peptide of SEQ ID NO: 1 are summarized in Table 14, and ranged from 0.012 to 0.11 nM (mean $IC_{50}$ 0.054±0.034 nM) when stimulated with 4 ng/mL IL-23 and 4 ng/mL IL-1β and from 0.16 to 0.34 nM (mean $IC_{50}$ 0.25±0.062 nM, n=6 rats) when blood was stimulated with 20 ng/mL IL-23.

TABLE 14

Summary of experiments to determine in vitro potency of the peptide of SEQ ID NO: 1 in a rat whole blood assay of IL-23-induced IL-17A secretion

| Experiment | $IC_{50}$ (nM) at 4 ng/mL IL-23 stimulation | $IC_{50}$ (nM) at 20 ng/mL IL-23 stimulation | Pooled blood (n = 6) or individual vehicle-dosed rats |
|---|---|---|---|
| 1 | 0.11 | ND | Pooled |
| 2 | 0.10 | ND | Pooled |
| 3 | 0.012 | 0.24 | Individual |
|  | 0.027 | 0.16 |  |
|  | 0.045 | 0.22 |  |
|  | 0.013 | 0.23 |  |
|  | 0.06 | 0.34 |  |
|  | 0.066 | 0.29 |  |
| Mean $IC_{50}$ | 0.054 | 0.25 |  |
| Standard Deviation | 0.034 | 0.062 |  |

The ex vivo potency of the orally dosed peptide of SEQ ID NO: 1 was similar to its in vitro activity. The in vitro rat whole blood $IC_{50}$ value for the peptide of SEQ ID NO: 1, as measured in Example 17, was 0.054±0.034 nM and 0.25±0.062 nM for stimulation with 4 and 20 ng/mL IL-23, respectively. Comparatively, the dilution-adjusted ex vivo $IC_{50}$ values for orally administered peptide of SEQ ID NO: 1 as measured in Example 16, were 0.032 nM and 0.27 nM, when blood was stimulated with 4 and 20 ng/mL IL-23, respectively.

These data demonstrate that the orally administered peptide of SEQ ID NO: 1 has dose-dependent systemic exposure in rat blood, which can be used to predict the level of systemic pharmacodynamic activity, by generating an $IC_{50}$ for exposure-dependent inhibition of ex vivo IL-23-stimulated IL-17A of the peptide of SEQ ID NO: 1, that is consistent with the $IC_{50}$ of blood taken from an un-dosed rat wherein the removed blood was treated subsequently with the peptide of SEQ ID NO: 1.

Example 18 Time-Course of Ex Vivo Pharmacodynamic Inhibition

Figure 6:
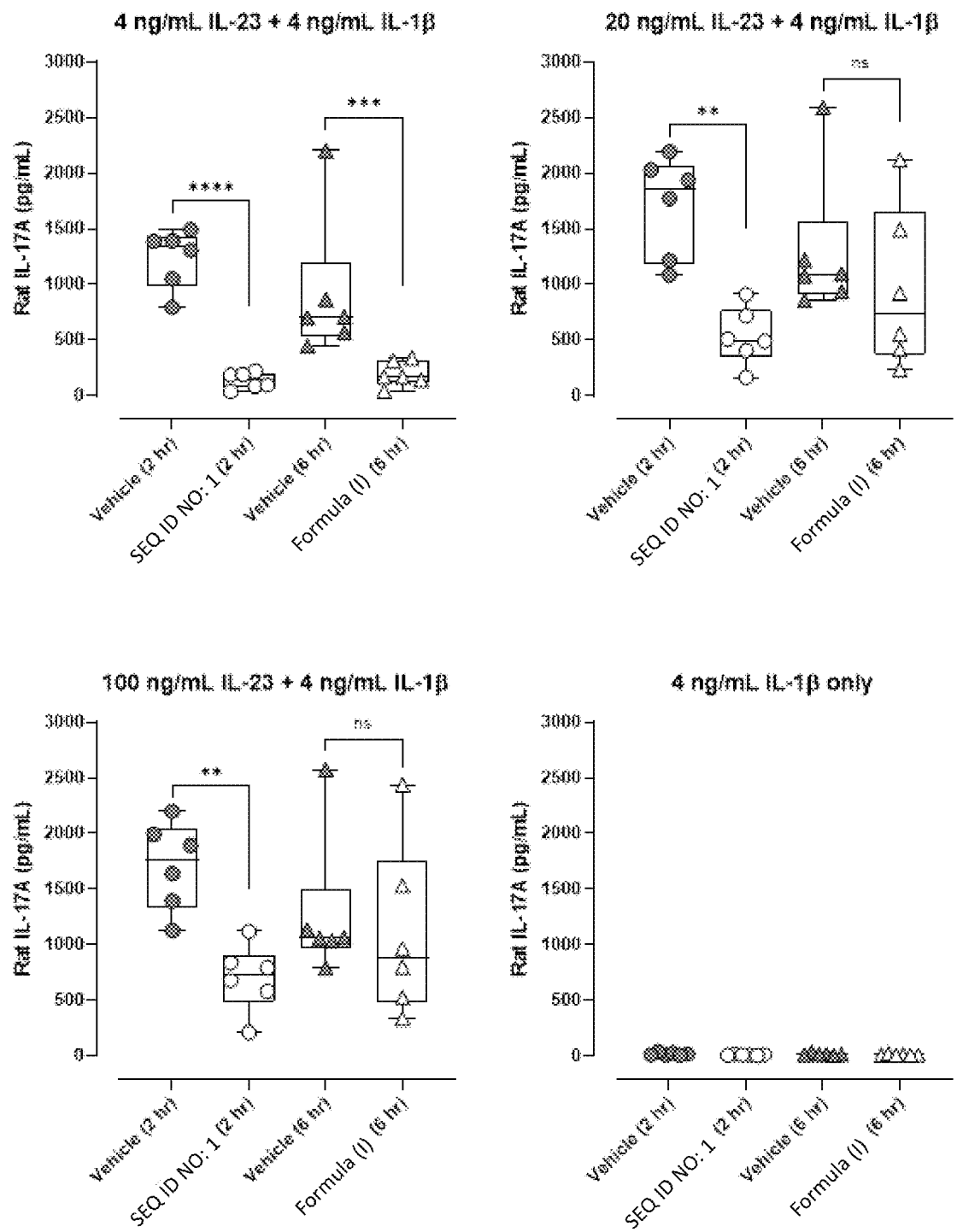
FIG. 6 shows interleukin 17A levels in rat blood stimulated with IL-23 vs 10 mg/kg oral dosing of the peptide of SEQ ID NO: 1 (labeled as "Formula (I)") at 2 hours and 6 hours post dose.

To determine ex vivo inhibition of IL-23-induced IL-17A secretion at different times after dosing with the peptide of SEQ ID NO: 1, rats were dosed with 10 mg/kg peptide and bled 2 or 6 hours later, followed by ex vivo stimulation with IL-23 and IL-1β. At 2 hours post-dosing, the median IL-17A production in blood from rats that received the peptide of SEQ ID NO: 1 was significantly reduced (relative to vehicle control samples) following stimulation with 100, 20, or 4 ng/mL IL-23 and 4 ng/mL IL-1β, respectively (FIG. 6). Cell culture supernatants were collected ~24 hours later for measurement of secreted IL-17A by ELISA. Technical replicates were averaged by arithmetic mean. Error bars were omitted for clarity. Box at interquartile range, bars at minima/maxima. One-way ANOVA on log-normalized values with Sidak's post-tests comparing treatment to vehicle at each timepoint (ns=not significant,  $p<0.01$, * $p<0.001$, **** $p<0.0001$).

At 6 hours post-dosing, the orally dosed peptide of SEQ ID NO: 1 had no significant effect on the ex vivo response to 100 and 20 ng/mL IL-23 and IL-1β but showed a significant decrease in median IL-17A levels in samples treated with 4 ng/mL IL-23 and 4 ng/mL The decreased inhibition at 6 hours relative to 2 hours post-dosing was consistent with plasma peptide exposure at this timepoint. Thus, there was no evidence of a prolonged pharmacodynamic effect ex vivo as the peptide exposure decreased in vivo.

Example 19. Rat Skin Activity—Inhibition of Gene Expression Downstream of IL-23 by Oral Administration of the Peptide of SEQ ID NO: 1

The purpose of the experiments of Example 19 was to measure tissue pharmacodynamics through measuring inhibition of gene expression downstream of IL-23, specifically IL-17A, IL-17F, and IL-22 genes in rat skin, following oral dosing of the peptide of SEQ ID NO: 1.

Ear inflammation was induced in Sprague-Dawley rats by daily intradermal injection of recombinant rat IL-23 on study days 0-3. Treatment with the peptide of SEQ ID NO: 1 (dose response by oral gavage; 1, 3, 10, 30, 100, and 300 mg/kg, twice a day) was initiated prophylactically starting one day prior to and continued through day 3 after induction of inflammation. All rats were humanely euthanized on day 4. An anti-IL-23 monoclonal antibody (administered intraperitoneally on days −1 and day 3) was included in all studies as a positive control and comparator.

Materials and Methods

Anti-IL-23p19 monoclonal antibody and IgG1 isotype monoclonal antibody were supplied ready to use at 2 mg/mL in PBS. Vehicle (50 mM phosphate buffer (PB)) was prepared by adding 10.11 g of $Na_2HPO_{4\cdot 7}H_2O$ and 1.70 g of $NaH_2PO_4$—$H_2O$ to 800 mL of distilled water and adjusted to a final pH of 7.4 using HCl or NaOH. Then the volume was brought up to 1 L using distilled water and stored at 4° C.

Test article was dissolved into phosphate buffer at the appropriate concentrations and aliquoted for each dose and stored at 4° C. Retentions of each dose formulation were obtained after the initial preparation and following the final dose on day 3 into Eppendorf tubes and stored at −80° C. for bioanalysis of test article by LCMS.

Recombinant rat IL-23 was diluted with PBS to a concentration of 75 μg/mL, divided into 2.0 mL aliquots, and stored at −80° C. Daily from day 0 through day 3, rats were anesthetized with isoflurane and IL-23 was intradermally injected (i.d.) into the right ear (1.5 μg in a volume of 20 μL). In the control group, 20 μL of PBS was injected.

Starting the morning prior to IL-23 injection through the evening of day 3, rats were dosed with either vehicle (phosphate buffer) or the peptide of SEQ ID NO: 1 compound twice daily (approximately 10 hours apart between doses during the day) by oral gavage (p.o.) in a volume of 5 mL/kg. In one experiment, the peptide of SEQ ID NO: 1 was also administered subcutaneously (s.c.) in a volume of 5 mL/kg. In another experiment, a once daily group was included by dosing 20 mg/kg of the peptide of SEQ ID NO: 1 compound in the morning and vehicle (PB) in the evening.

Anti-IL-23p19 antibody or isotype antibody was administered via intraperitoneal injection (i.p.) in a volume of 5 mL/kg on days −1 and 3.

At the end of the study, four days after induction with IL-23 (approximately 16 hours after the evening dose on day 3), animals were euthanized by $CO_2$ asphyxiation. The ear tissue was weighed, snap frozen, and stored at −80° C. for gene expression analysis of inflammatory genes (IL-22, IL-17A, IL-17F, TNF). Additional ear tissue was processed in the same manner for bioanalysis of the peptide of SEQ ID NO: 1 by LCMS. Further ear tissue was fixed in 10% neutral buffered formalin (NBF) for 24 hours, then transferred into 70% ethanol for histological processing and analysis.

Histopathology evaluation and scoring: Skin samples from the ears were processed as follows. Five micron sections were mounted on slides, stained with hemoxylin and eosin and evaluated using light microscopy by a board-certified veterinary pathologist blinded to the treatment conditions. Each ear sample was scored individually. Epidermal thickness (m) was scored on a 0-4 scale (0: within normal limits, thickness ≤30 μm; 1: predominately <50 μm; 2: predominately 50-80 μm; 3: predominately 80-110 μm, 4: >110 μm) and other features (epidermal exudates, erosion/ulceration, acanthosis, and inflammation) were scored according to increasing severity on a 0-5 scale.

Results

Figure 7:
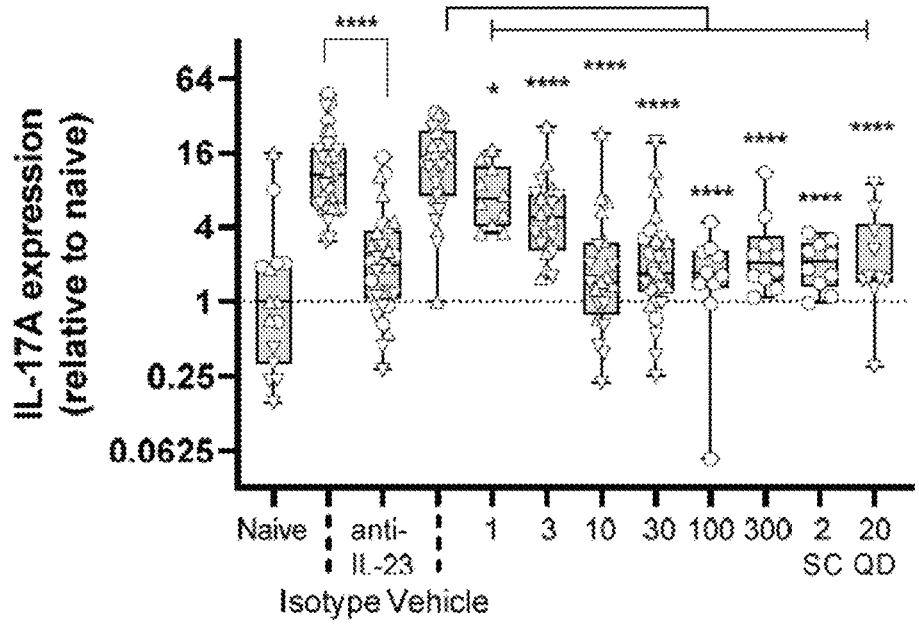
FIG. 7 shows changes in skin interleukin-17A (IL-17A) gene expression in naïve rats or rats after intradermal administration of recombinant rat IL-23 with oral administration of vehicle or the peptide of SEQ ID NO: 1 (1, 3, 10, 30, 100, 300 mg/kg BID), or intraperitoneal administration of anti-IL-23 or isotype antibody.
Figure 8:
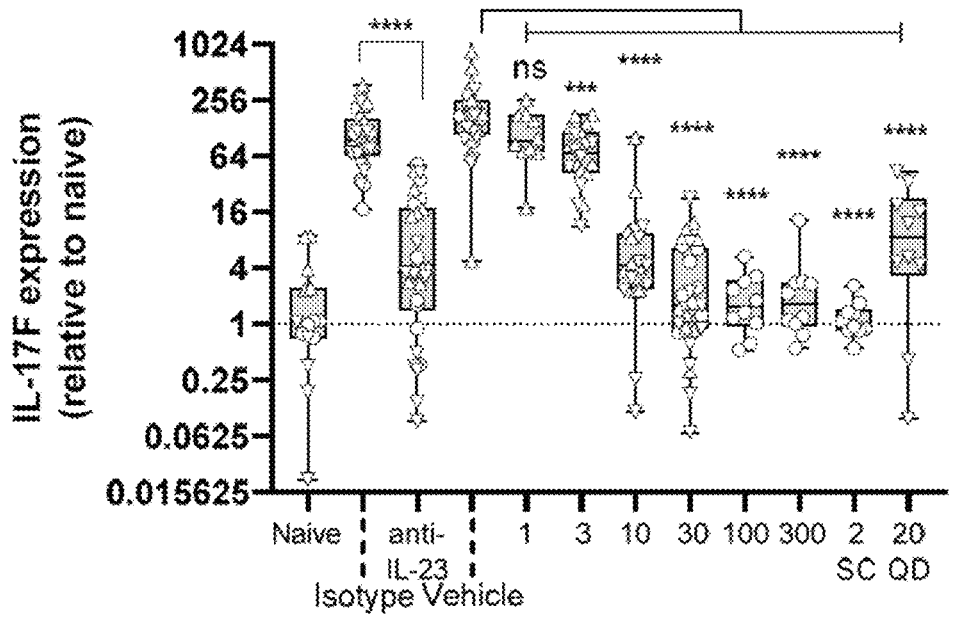
FIG. 8 shows changes in skin interleukin-17F (IL-17F) gene expression in naïve rats or rats after intradermal administration of recombinant rat IL-23 with oral administration of vehicle or the peptide of SEQ ID NO: 1 (1, 3, 10, 30, 100, 300 mg/kg BID), or intraperitoneal administration of anti-IL-23 or isotype antibody.
Figure 9:
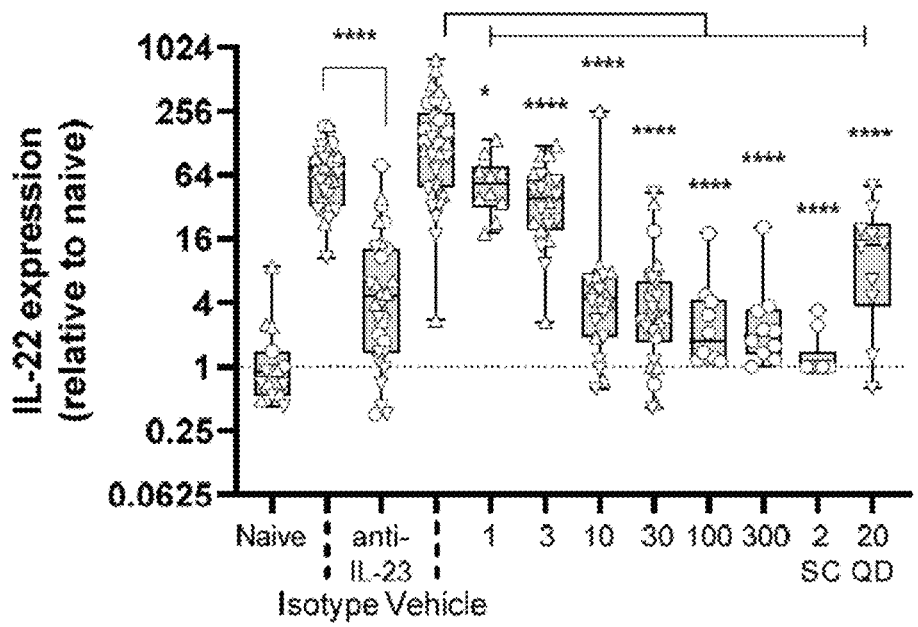
FIG. 9 shows changes in skin interleukin-22 (IL-22) gene expression in naïve rats or rats after intradermal administration of recombinant rat IL-23 with oral administration of vehicle or the peptide of SEQ ID NO: 1 (1, 3, 10, 30, 100, 300 mg/kg BID), or intraperitoneal administration of anti-IL-23 or isotype antibody.

The orally administered peptide of SEQ ID NO: 1 attenuated IL-23 induced expression of IL-17A, IL-17F, and IL-22 in a dose dependent manner (see FIGS. 7, 8, and 9, respectively).

FIG. 7 shows changes in skin IL-17A gene expression in naïve rats or rats after intradermal administration of recombinant rat IL-23 with oral administration of vehicle or the compound of the peptide of SEQ ID NO: 1 (1, 3, 10, 30, 100, 300 mg/kg b.i.d.; days −1 to 3), or intraperitoneal administration of anti-IL-23 or isotype antibody (4 mg/kg on days −1 and 3). IL-23 induced about 15-fold increase in median IL-17A expression that was reduced by treatment of the peptide of SEQ ID NO: 1 at all tested doses and at doses of 10 mg/kg (b.i.d.) or higher to a comparable degree as anti-IL-23 antibody.

FIG. 8 shows changes in skin interleukin-17F (IL-17F) gene expression in naïve rats or rats after intradermal administration of recombinant rat IL-23 with oral administration of vehicle or the peptide of SEQ ID NO: 1 (1, 3, 10, 30, 100, 300 mg/kg BID), or intraperitoneal administration of anti-IL-23 or isotype antibody.

FIG. 9 shows changes in skin interleukin-22 (IL-22) gene expression in naïve rats or rats after intradermal administration of recombinant rat IL-23 with oral administration of vehicle or the peptide of SEQ ID NO: 1 (1, 3, 10, 30, 100, 300 mg/kg BID), or intraperitoneal administration of anti-IL-23 or isotype antibody.

Example 20. Rat Skin Activity—Inhibition of IL-23 Induced Ear Thickening by Oral Administration of the Peptide of SEQ ID NO: 1

The rat IL-23 induced skin inflammation model was used to evaluate the tissue pharmacodynamics activity of the IL-23R peptide antagonist of the peptide of SEQ ID NO: 1. The purpose of the rat ear thickening experiment is to determine whether the orally dosed peptide of SEQ ID NO: 1 has sufficient systemic exposure to provide inhibition of IL-23R in skin tissue, thus modeling orally dosed therapeutic efficacy in psoriatic skin tissue. The animals from Example 19 were also used for Example 20. On day 0, prior to IL-23 injection, the ipsilateral ears averaged approximately 0.4 mm. In rats injected with saline, the ears did swell as a result of the repeated intradermal injections, by an average of 0.053 mm by day 4. By comparison, injection of IL-23 caused the ears of both vehicle-treated and isotype antibody-treated rats to progressively increase in thickness, reaching an average of approximately 0.240 to 0.242 mm by day 4, respectively. Blockade of IL-23 by anti-IL-23 monoclonal antibody treatment reduced ear swelling to only 0.133 mm by day 4, and the differences on days 2-4 were all statistically significant. Treatment with the peptide of SEQ ID NO: 1 also demonstrated reduction of IL-23-induced swelling, with the highest dose of 300 mg/kg, b.i.d., reducing day 4 swelling to an average of 0.120 mm. Reduction in ear thickening by progressively lower doses of the peptide of SEQ ID NO: 1 was generally dose-responsive down to a dose of 3 mg/kg, b.i.d. Doses of 1, 3, 10, 100, and 300 mg/kg, p.o., b.i.d. reduced ear thickness compared to vehicle treatment by a statistically significant degree on days 3 and 4, and the dose of 30 mg/kg, p.o., b.i.d. was statistically significant on days 2-4. Reductions in ear thickness at doses of 2 mg/kg, s.c. and 20 mg/kg, p.o., q.d. were not statistically significant (FIG. 9 and Table 15).

Results

The orally administered peptide of SEQ ID NO: 1 prevented IL-23 induced ear thickening. At doses of 10 mg/kg (p.o., b.i.d.) and above, the efficacy of the peptide of SEQ ID NO: 1 equaled or exceeded that of anti-IL-23 antibody treatment.

Figure 10:
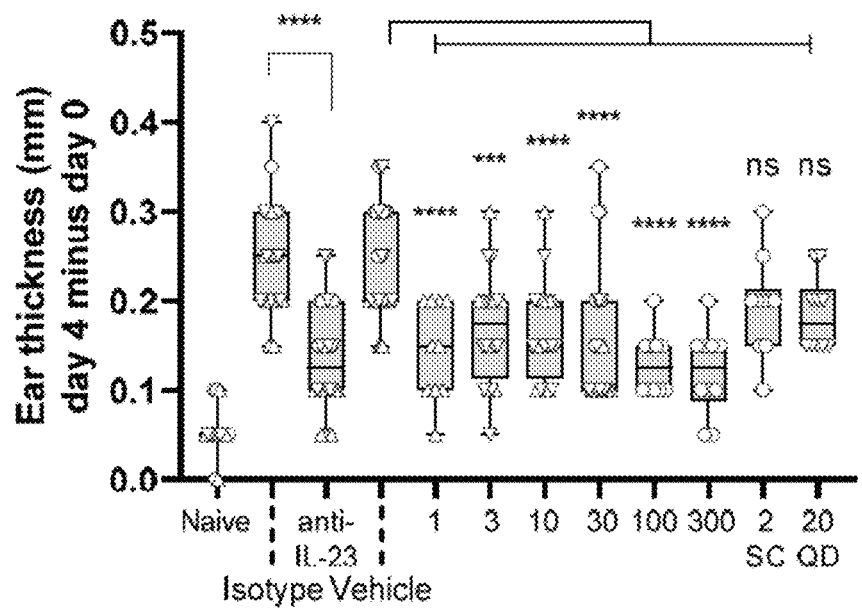
FIG. 10 shows change in ear thickness of naïve rats or rats after intradermal administration of recombinant rat IL-23 with oral administration of vehicle or the peptide of SEQ ID NO: 1 (1, 3, 10, 30, 100, 300 mg/kg b.i.d.), or intraperitoneal administration of anti-IL-23 or isotype antibody.

FIG. 10 shows change in ear thickness (mm) of naïve rats or rats after intradermal administration of recombinant rat IL-23 with oral administration of vehicle or the peptide of SEQ ID NO: 1 compound (1, 3, 10, 30, 100, 300 mg/kg b.i.d.; 20 mg/kg q.d.; days −1 to 3), or intraperitoneal administration of anti-IL-23 or isotype antibody (4 mg/kg on days −1 and 3). IL-23 induced greater ear thickening in the isotype antibody treated rats (median increase 0.25 mm) and vehicle treated rats (median increase 0.20 mm) compared to naïve rats (median increase 0.05 mm). The peptide of SEQ ID NO: 1 (1, 3, 10, 30, 100, 300 mg/kg, p.o., b.i.d., days −1 to 3) showed reduction of ear thickening at day 4 compared to vehicle treatment (Table 15).

TABLE 15

IL-23 Induced Ear Thickening, Comparison to Controls

| Treatment | Dose | Control | Day 1 | Day 2 | Day 3 | Day 4 |
|---|---|---|---|---|---|---|
| Anti-IL-23 antibody | 4 mg/kg, i.p. | Isotype | ns | ** | **** | **** |
| SEQ ID NO: 1 | 1 mg/kg, p.o., b.i.d. | Vehicle | ns | ns | **** | **** |
| SEQ ID NO: 1 | 3 mg/kg, p.o., b.i.d. | Vehicle | ns | ns | *** | *** |
| SEQ ID NO: 1 | 10 mg/kg, p.o., b.i.d. | Vehicle | ns | ns | *** | **** |
| SEQ ID NO: 1 | 30 mg/kg, p.o., b.i.d. | Vehicle | ns | * | **** | **** |
| SEQ ID NO: 1 | 100 mg/kg, p.o., b.i.d. | Vehicle | ns | ns | **** | **** |
| SEQ ID NO: 1 | 300 mg/kg, p.o., b.i.d. | Vehicle | ns | ns | *** | **** |
| SEQ ID NO: 1 | 2 mg/kg, s.c., b.i.d. | Vehicle | ns | ns | ns | ns |
| SEQ ID NO: 1 | 20 mg/kg, p.o., q.d. | Vehicle | ns | ns | ns | ns |

(ns = not significant,  $p < 0.01$, * $p < 0.001$, **** $p < 0.0001$)

Thus the orally dosed peptide of SEQ ID NO: 1 demonstrated dose-dependent inhibition of IL-23 in rat skin, as measured in the ear thickening experiment.

Example 21 Phase 1 First in Human Pharmacokinetics (PK)

A Phase 1 First In Humans (FIH) of the compound Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) in healthy participants is currently being conducted to assess the safety and tolerability of that compound over the dose range tested (10 mg to 1000 mg). All cohorts are complete from this study.

Results from the Part 1 (Single Ascending Dose Studies) administered as single doses up to 1000 mg, Part 2 (Multiple Ascending Dose Studies) doses up to 1000 mg, and Part 3 open label relative BA/food effect study have been reviewed.

Systemic exposure (maximum observed serum concentration [$C_{max}$] and AUC) of the drug is approximately dose-proportional across the dose range evaluated to date. After multiple 10 mg or 25 mg once-daily dosing, steady state was achieved by Day 7, consistent with the observed mean terminal phase half-life of approximately 10 to 12 hours. After multiple once-daily dosing, mean accumulation of 13% to 50% for AUC was observed, which was consistent with the half-life.

The preliminary single-dose PK of Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) from the ongoing FIH study are summarized in Table 16.

TABLE 16

Mean (% CV) Single-Dose Pharmacokinetic Parameters for Ac-[Pen]*-N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) PART 1 ADMINISTERED AS AN ORAL SOLUTION FORMULATION UNDER FASTED CONDITIONS

| Treatment | $C_{max}$ (ng/mL) | $T_{max}$(h) Median (min, max) | AUC$_{inf}$ (ng.h/mL) | $t_{1/2}$ (h) |
|---|---|---|---|---|
| 10 mg (n = 6) | 0.17 (53.3) | 2.5 (1, 5) | 1.56 (47.1) | 5.0 (10.9) |
| 25 mg (n = 6) | 0.79 (69.7) | 1.5 (0.5, 5) | 6.47 (43.0) | 8.5 (27.7) |
| 100 mg (n = 5) | 1.48 (27.5) | 3.0 (1, 6) | 20.8 (31.3) | 11.7 (46.3) |
| 300 mg (n = 6) | 3.97 (47.2) | 4.0 (3, 8) | 51.0 (40.5) | 9.28 (13.8) |
| 1000 mg (n = 6) | 8.30 (10.2) | 4.5 (1, 8) | 140.9 (12.6) | 8.73 (14.5) |

A food effect assessment was completed for an enteric-coated tablet containing the AbE as part of the ongoing FIE study. The study design and topline results from this study are summarized below. Subjects received a single dose of Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) 25 mg on 4 occasions with a washout period of at least 5 days between treatments.

Of the 12 participants who enrolled in the study, 10 subjects completed all periods of the crossover from whom PK data is available and are summarized in Table 17.

TABLE 17

Pharmacokinetic Parameters (Geometric Means) and Relative Bioavailability Results for Ac-[Pen]*-N-T-[W(7-Me)]-[Lys(Ac)]-[Pen]*-Phe[4-(2-aminoethoxy)]-[2-Nal]-[THP]-E-N-[3-Pal]-Sarc-NH2 (*Pen-Pen form disulfide bond) (SEQ ID NO: 1) From FIH Study Part 3

| Treatment (n = 10) | $C_{max}$ (ng/mL) | $T_{max}$ (h) Median (min, max) | AUC$_{inf}$ (ng.h/mL) | Relative Bioavailability |
|---|---|---|---|---|
| 25 mg Oral Solution, Fasted | 0.359 | 2 (1, 8) | 4.75 | 100 |
| 25 mg Tablet without sodium caprate (NaC10), Fasted | 0.105 | 7 (4, 12) | 2.06 | 50.7 |
| 25 mg Tablet with NaC10, Fasted | 6.451 | 4 (1, 6) | 34.12 | 688.4 |
| 25 mg Tablet with NaC10, Fed | 1.770 | 12 (5, 24) | 34.44 | 435.1 |

The results from this study indicate that the tablet formulation with the enteric coating (pH sensitive functional coating) administered under fasted conditions had a median lag time of 3 hours and a mean oral bioavailability of approximately 50% relative to the oral solution. In contrast, the tablet formulation with the enteric coating containing the AbE administered under fasted conditions had a median lag time of 1.5 hours and a mean oral bioavailability of approximately 700% relative to the oral solution. The absorption enhanced enteric-coated tablet formulation administered under fed conditions had a median lag time of 7 hours and a mean oral bioavailability of approximately 400% relative to the oral solution. Dosing of the absorption enhanced tablet formulation with food was associated increased variability (coefficient of variation [CV] ~90%) compared to the same formulation administered in the fasted state (CV~57%).

In summary, the results of this relative study indicate that a tablet formulation of the peptide containing the absorption enhancer (AbE) sodium caprate (NaCl0) can significantly increase the oral bioavailability and systemic exposure of Ac-[Pen]*—N-T-[W(7-Me)]-[Lys(Ac)]-[Pen]*-Phe[4-(2-aminoethoxy)]-[2-Nal]-[THP]-E-N-[3-Pal]-Sarc-NH$_2$ (*Pen-Pen form disulfide bond) (SEQ ID NO: 1) while minimizing the total daily dose requirements. Since the goal of using an absorption enhanced oral formulation is to increase the systemic exposure to the peptide without increasing the amount of administered drug, the approximately 5-fold relative increase in exposure is covered by the existing preclinical toxicology margins.

Example 22: The Peptide of SEQ ID NO: 1 Reduces Gut Inflammation in an Animal Model of IBD In vivo anti-inflammatory activity of the peptide of SEQ ID NO: 1 was evaluated in the rat trinitrobenzenesulfonic acid (TNBS)-induced colitis model of IBD. Intracolonic TNBS instillation in Sprague-Dawley rats induces colonic inflammation driven in part by IL-23/IL-23R signaling (Cheng X, Taranath R, Mattheakis L, Bhandari A, Liu D. The biomarker profile of PTG-200, an oral peptide antagonist of IL-23 receptor, tracks with efficacy in a preclinical model of IBD. J Crohns Colitis. AGA Abstracts, 2017). The TNBS rat model therefore provides a measure of the local GI effects of SEQ ID NO: 1 on IL-23/IL-23R signaling. These results also supported the human dose predictions for the peptide of SEQ ID NO: 1.

Study Design

The peptide of SEQ ID NO: 1 was evaluated in the rat TNBS model with oral dosing only, three times a day (0.03, 0.1, 0.3, 1, 3, 10, mg/kg/day), in three independent rat TNBS experiments. In all studies, the peptide of SEQ ID NO: 1 was dosed starting 2 days prior to TNBS induction through day 6, with euthanasia scheduled on day 7.

Results

Figure 11:
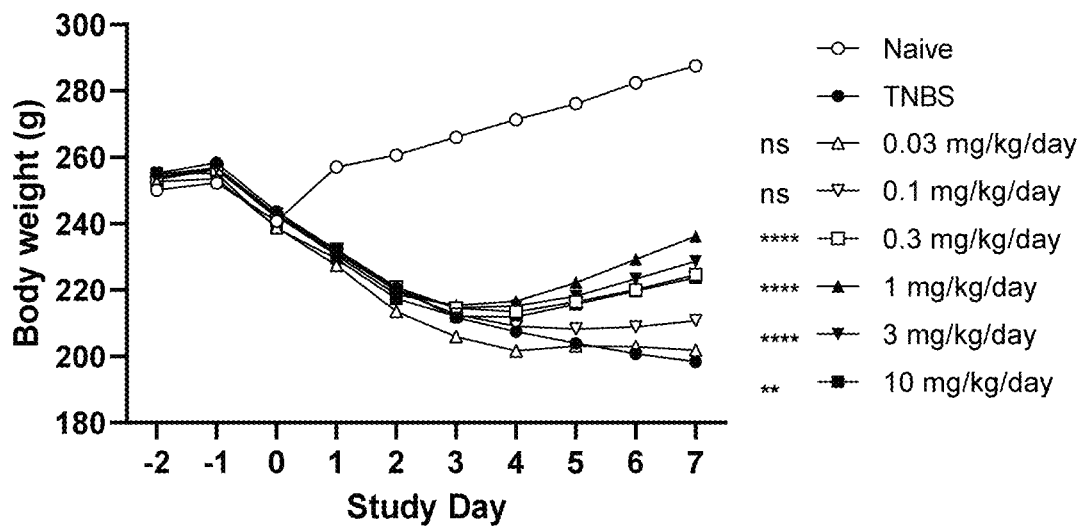
FIG. 11 shows Time course of body weight gain in naïve rats or weight loss in rats after intracolonic administration of TNBS with oral administration of water (days −2 through day 6) or the peptide of SEQ ID NO: 1 (0.03, 0.1, 0.3, 1, 3, and 10 mg/kg/day; days −2 through day 6).

Following TNBS administration and induction of colitis, rats showed a precipitous drop in body weight (FIG. 11). In contrast, naïve animals continued to gain weight over the experimental time frame. These differences resulted in a net loss of 91.9 g (95% CI: 80.8, 103 g) between naïve and TNBS groups by day 7 reflecting a decline in overall health as a result of TNBS instillation. Initiation of treatment with the peptide of SEQ ID NO: 1 (0.03, 0.1, 0.3, 1, 3, and 10 mg/kg/day) prevented and reversed the TNBS-induced weight loss across all 3 studies. The attenuation of body weight loss by the peptide of SEQ ID NO: 1 was dose-related in the range of 0.03 to 1 mg/kg/day. The effects of 3 and 10 mg/kg/day were comparable to that seen with 1 mg/kg/day. Based on combined analysis of three TNBS experiments, as early as day 5 post-TNBS, the peptide of SEQ ID NO: 1 (1 mg/kg/day, p.o.) showed a significant reduction in body weight loss ($p=0.022$), and by day 7, doses of 0.3, 1, 3, and 10 mg/kg/day provided significant treatment effect on body weight loss ($p<0.0001$, $p<0.0001$, $p<0.0001$, and $p=0.002$ respectively). Based on day 7 as the study endpoint, the peptide of SEQ ID NO: 1 at 0.3 mg/kg/day was considered the minimally efficacious dose (FIG. 11).

FIG. 11 shows time course of body weight gain in naïve rats or weight loss in rats after intracolonic administration of TNBS with oral administration of water (days −2 through day 6) or the peptide of SEQ ID NO: 1 (0.03, 0.1, 0.3, 1, 3, and 10 mg/kg/day; days −2 through day 6). Data represent mean body weight (n=10-29 rats, combined for 3 studies). Error bars are omitted for the sake of clarity. The body weight in SEQ ID NO: 1 (0.3, 1, 3, and 10 mg/kg/day) treated rats was significantly different from vehicle group by day 7 (ns=not significant,  $p<0.001$, ** $p<0.0001$).

Figure 12:
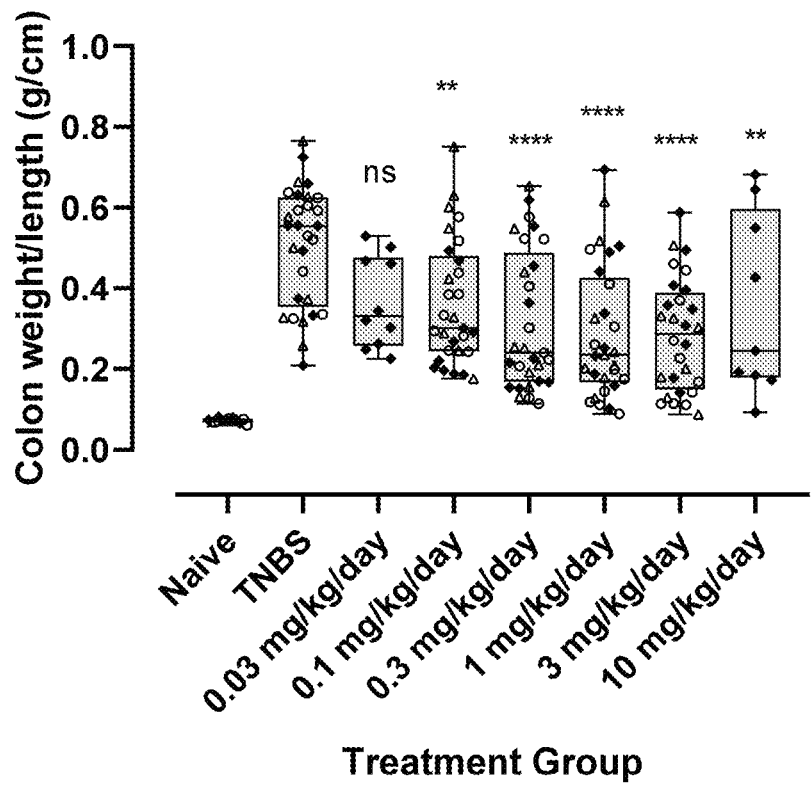
FIG. 12 shows changes in colon weight/length ratio in naïve rats or in rats after intracolonic administration of TNBS with oral administration of water (days −2 through day 6) or the peptide of SEQ ID NO: 1 (0.03, 0.1, 0.3, 1, 3, and 10 mg/kg/day; days −2 through day 6).

The TNBS-induced colitis manifests in shortening of the colon, increased edema, and thickening of the colon, resulting in an overall increase in colon weight/length ratio in TNBS-treated rats compared to naïve rats. The colon weight/length ratio in naïve rats was ~0.1 g/cm and increased to ~0.5 g/cm in TNBS-treated rats (estimated absolute difference of 0.422 g/cm, 95% CI: 0.335, 0.508 g/cm). The peptide of SEQ ID NO: 1 (0.03, 0.1, 0.3, and 1 mg/kg/day) showed a dose-related trend for attenuation of changes in colon weight/length ratio, with a similar magnitude of effect at 1, 3, and 10 mg/kg/day (FIG. 12). Compared to the TNBS group, the peptide of SEQ ID NO: 1 at doses of 0.1, 0.3, 1, 3, and 10 mg/kg/day showed significant treatment effect of reducing colon weight/length ratio ($p=0.0019$, $p<0.0001$, $p<0.0001$, $p<0.0001$, and $p=0.0073$ respectively), with 0.1 mg/kg/day considered the minimally efficacious dose (FIG. 12).

FIG. 12 shows changes in colon weight/length ratio in naïve rats or in rats after intracolonic administration of TNBS with oral administration of water (days −2 through day 6) or the peptide of SEQ ID NO: 1 (0.03, 0.1, 0.3, 1, 3, and 10 mg/kg/day; days −2 through day 6). Data from 3 different studies were combined (represented by shapes of the symbols at each dose level: study 1 (Δ), study 2 (♦), study 3 (○); box at interquartile range, bars at minima/maxima. The peptide of SEQ ID NO: 1 at doses of 0.1, 0.3, 1, 3, and 10 mg/kg/day showed significant treatment effect of reducing colon weight/length ratio (ns=not significant,  $p<0.01$, ** $p<0.0001$).

Figure 13:
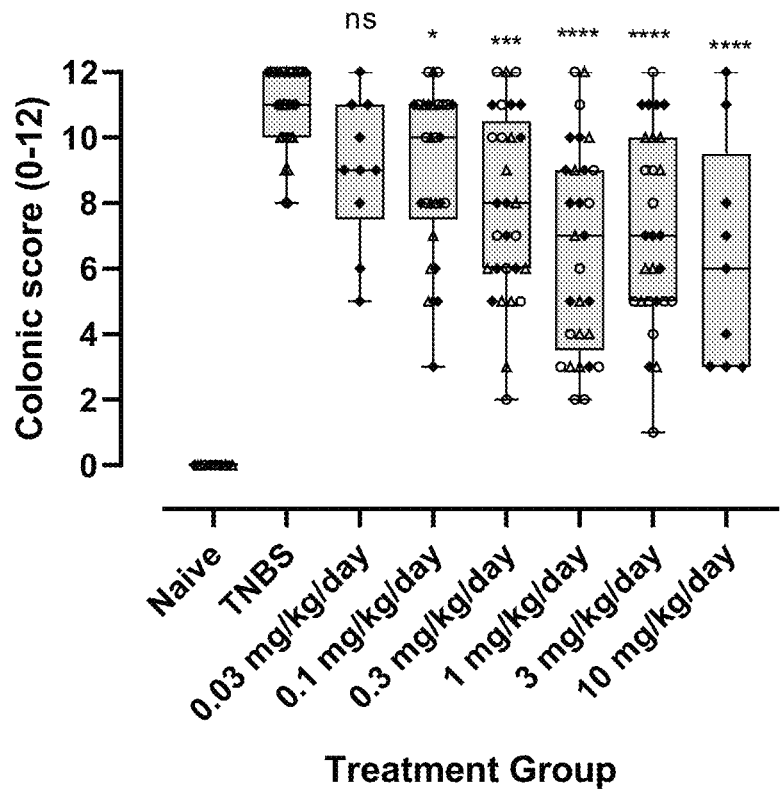
FIG. 13 shows changes in colon inflammation score in naïve rats or in rats after intracolonic administration of TNBS with oral administration of water or the peptide of SEQ ID NO: 1 (0.03, 0.1, 0.3, 1, 3, and 10 mg/kg/day; days −2 through day 6).

Disease severity resulting from TNBS can be assessed by qualitative scoring of the formation of strictures, adhesions, ulceration, and increase in wall thickness as described previously. The summed colon score is significantly increased by a median of 11 (interquartile range: 10-12) in the TNBS group compared to naïve rats (FIG. 13). The colon scores in the lowest dose of the peptide of SEQ ID NO: 1 (0.03 mg/kg/day) were similar to that seen with TNBS alone. The colon score was reduced by treatment with the peptide of SEQ ID NO: 1 at other doses (0.1, 0.3, 1, 3, and 10 mg/kg/day ($p=0.0187$, $p=0.0002$, $p<0.0001$, $p<0.0001$, and $p<0.0001$, respectively)), with an overlapping level of inhibition of colonic inflammation in this dose range. Based on this qualitative scoring, the peptide of SEQ ID NO: 1 at 0.1 mg/kg/day was considered to be the minimally efficacious dose for colonic score (FIG. 13).

FIG. 13 shows changes in colon inflammation score in naïve rats or in rats after intracolonic administration of TNBS with oral administration of water or the peptide of SEQ ID NO: 1 (0.03, 0.1, 0.3, 1, 3, and 10 mg/kg/day; days −2 through day 6). Data from 3 different studies were combined (represented by shapes of the symbols at each dose level: study 1 (Δ), study 2 (♦), study 3 (○); box at interquartile range, bars at minima/maxima). The colons were scored on the following parameters: adhesion (0-2), stricture (0-3), ulcer (0-5), and wall thickness (0-2) for a total sum component score range of 0-12. The colon score was reduced by treatment with the peptide of SEQ ID NO: 1 at doses of 3, 10, 30, and 100 mg/kg/day (ns=not significant, * $p<0.05$, * $p<0.001$, ** $p<0.0001$).

At the end of each study, colonic content and colon tissue samples were collected from each animal and analyzed for drug concentrations by LC-MS/MS. High concentrations of SEQ ID NO: 1 were observed in colonic content and colon tissue and levels increased with increase in administered dose (Table 18).

TABLE 18

MEAN CONCENTRATIONS OF SEQ ID NO: 1 IN TISSUES FOLLOWING ORAL ADMINISTRATION OF SEQ ID NO: 1 IN THE RAT TRINITROBENZENESULFONIC ACID-INDUCED COLITIS MODEL

| | | SEQ ID NO: 1 Concentration (ng/g [for tissue]) (Study 1) | | | | | | |
|---|---|---|---|---|---|---|---|---|
| Tissue | Dose (mg/kg) Regimen | — | 0.033 | 0.1 TID | 0.33 TID | 1 TID | — | — | — |
| | Total Daily Dose (mg/kg) | — | 0.1 | 0.3 | 1 | 3 | — | — | — |
| Colon | | — | 24.2 | 48.2 | 160 | 632 | — | — | — |
| N (colon) | | — | 9 | 9 | 9 | 8 | — | — | — |
| Colon content | | — | 779 | 1,847 | 6,334 | 17,481 | — | — | — |
| N (colon content) | | — | 9 | 9 | 9 | 8 | — | — | — |

TABLE 18-continued

MEAN CONCENTRATIONS OF SEQ ID NO: 1 IN TISSUES FOLLOWING ORAL ADMINISTRATION OF SEQ ID NO: 1 IN THE RAT TRINITROBENZENESULFONIC ACID-INDUCED COLITIS MODEL

| | | SEQ ID NO: 1 Concentration (ng/g [for tissue]) (Study 2) | | | | | | | |
|---|---|---|---|---|---|---|---|---|---|
| | Dose (mg/kg) Regimen | 0.01 TID | 0.033 TID | 0.1 TID | 0.33 TID | 1 TID | 3.3 TID | 0.5 BID | 1 QD |
| Tissue | Total Daily Dose (mg/kg) | 0.03 | 0.1 | 0.3 | 1 | 3 | 10 | 1 | 1 |
| Colon | | BQL | 31.9 | 90.1 | 319 | 889 | 2,681 | 375 | 549 |
| N (colon) | | 10 (9<sup>a</sup>) | 10 (3<sup>a</sup>) | 10 | 10 | 10 | 9 | 10 | 10 |
| Colon content | | 171 | 588 | 1,987 | 7,442 | 22,244 | 73,511 | 11,166 | 11,743 |
| N (colon content) | | 10 (1<sup>a</sup>) | 10 | 10 | 10 | 10 | 9 | 10 | 10 |
| | | SEQ ID NO: 1 Concentration (ng/g [for tissue]) (Study 3) | | | | | | | |
| | Dose (mg/kg) Regimen | — | 0.033 TID | 0.1 TID | 0.33 TID | 1 TID | — | — | — |
| Tissue | Total Daily Dose (mg/kg) | — | 0.1 | 0.3 | 1 | 3 | — | — | — |
| Colon | | — | BQL | 44.4 | 158 | 509 | — | — | — |
| N (colon) | | — | 10 (8<sup>a</sup>) | 10 (2) | 10 | 10 | — | — | — |
| Colon content | | — | 567 | 3,181 | 6,046 | 20,829 | — | — | — |
| N (colon content) | | — | 10 | 10 | 10 | 10 | — | — | — |

Note:
Three independent experiments were conducted in TNBS-induced colitis male Sprague Dawley rats and results are presented for each experiment.
<sup>a</sup>Number of values BQL; if half or more samples have values, BQL is set to 0, and averages are calculated.
"—" = not applicable; BID = twice daily; BQL = below quantitation limit; N = number; QD = once daily; TID = 3 times daily; TNBS = trinitrobenzenesulfonic acid.

In summary, in vivo studies in a TNBS-induced colitis model in rats showed dose- and GI-exposure-related attenuation of disease parameters, with a minimal efficacious dose 0.3 mg/kg/day for the peptide of SEQ ID NO: 1. Correlation was observed between colonic tissue, fecal concentrations, and pharmacologic activity/efficacy endpoints.

Example 23: First in Human Clinical Study, Evidence of Systemic IL-23 Pathway Engagement with Orally Administered Peptide of SEQ ID NO: 1

Ex Vivo Whole Blood IL-23-Induced IFNγ Production Assay

An ex vivo whole blood IL-23 induced IFNγ assay was used to evaluate the systemic pharmacodynamic activity of the orally administered peptide of SEQ ID NO: 1 in the first-in-human study. The assay was implemented in all Multiple Ascending Dose (MAD) cohorts, at multiple timepoints on Day 1 and Day 10, where healthy volunteers were given placebo or one of the doses of the peptide of SEQ ID NO: 1 (10 mg, 25 mg, 100 mg, 300 mg, 1000 mg) orally once a day for 10 consecutive days. On Days 1 and 10, when the assay was performed, subjects received their dose of placebo or peptide of SEQ ID NO: 1 following an overnight fast of approximately 10 hours and remained fasted for approximately 4 hours following dosing. After oral dosing on days 1 and 10, whole blood from the subjects was stimulated ex vivo with either IL-2 (10 ng/mL) and IL-18 (20 ng/mL) or IL-2 (10 ng/mL), IL-18 (20 ng/mL), and IL-23 (0.5 ng/mL) in TruCulture™ tubes (Rules Based Medicine, $Q^2$ solutions company) for stimulation of IFNγ production. The production of IFNγ is expected to be suppressed if IL-23R signaling is inhibited. Therefore, lower IFNγ production in the assay is associated with sufficient exposure to achieve systemic pharmacodynamic (PD) activity of orally dosed peptide of SEQ ID NO: 1.

Methods

Whole blood was collected in TruCulture™ tubes according to manufacturer instructions, the tubes were incubated at 37° C. in a block thermostat for 24 hours (±1 hour). Following incubation at 37° C., supernatants were harvested according to TruCultube™ tube manufacturer instructions (Rules Based Medicine, $Q^2$ solutions company). An ELISA assay was used to quantify the levels of IFNg in the supernatants.

Results

Figure 14:
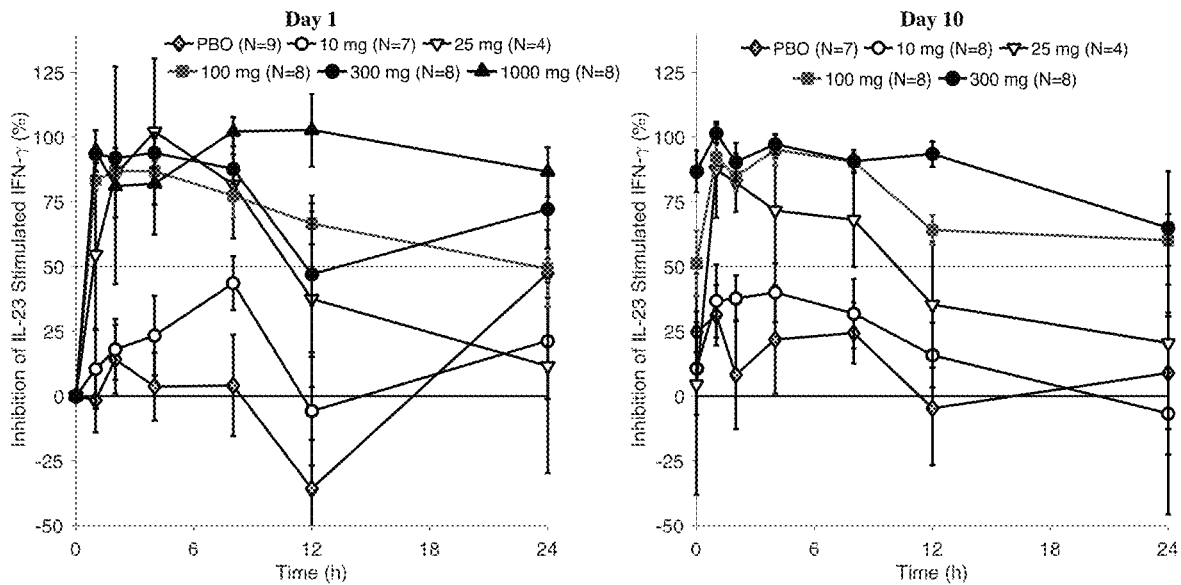
FIG. 14 shows percent inhibition of IL-23 induced IFNγ production data (mean±SE) from multiple indicated timepoints on Day 1 and Day 10 of the MAD cohorts relative to baseline.

Mean systemic PD activity for 25 mg, 100 mg, 300 mg and 1000 mg cohorts reached close to 100% maximum inhibition and maintained >50% inhibition for at least ~8 hours. We also observed that there were dose-dependent effects on inhibition of IFNγ particularly when the peptide of SEQ ID NO: 1 reached steady-state levels on Day 10 (FIG. 14). Therefore, the orally administered peptide of SEQ ID NO: 1 demonstrated a dose dependent inhibition of IL-23 stimulated IFNγ production in human whole blood. Since the blood is diluted 3-fold in the assay, the measured level of IFNγ inhibition underestimates the in vivo pharmacodynamic activity of the peptide of SEQ ID NO: 1 in the blood.

The First-in-human study systemic IFNγ pharmacodynamic dataset for 10, 25, 100, 300 and 1000 mg cohorts relative to placebo is displayed in FIG. 14. The percent inhibition of IL-23 induced IFNγ production data (mean±SE) from multiple indicated timepoints on Day 1 and Day 10 of the MAD cohorts is shown relative to baseline. One outlier subject from placebo (PBO) and 10 mg cohorts were excluded. IFNγ=interferon gamma; Time (h)=Time (hours).

Ex Vivo Whole Blood Phosphorylation of STAT3 Assay

An ex vivo whole blood IL-23 induced STAT3 phosphorylation assay was also used to evaluate the systemic pharmacodynamic activity of the orally administered peptide of SEQ ID NO: 1 in the first-in-human study. This proximal IL-23R signaling assay was performed by analyzing IL-23 induced phosphorylation of STAT3 using a flow cytometer. Assay was implemented in the 25 mg MAD cohort, at multiple timepoints on Day 1 and Day 10, where healthy volunteers were given placebo or 25 mg of peptide of SEQ ID NO: 1 orally once a day for 10 consecutive days. On Days 1 and 10, when the assay was performed, subjects received their dose of placebo or peptide of SEQ ID NO: 1 following an overnight fast of approximately 10 hours and remained fasted for approximately 4 hours following dosing. After oral dosing on days 1 and 10, whole blood from the subjects was incubated ex-vivo with or without IL-23 for evaluation of STAT3 phosphorylation in specific immune cell subsets. IL-23 induced phosphorylation of STAT3 is expected to be suppressed in immune cell subsets if IL-23R signaling is inhibited. Therefore, lower STAT3 phosphorylation as readout by the assay is associated with sufficient exposure to achieve systemic pharmacodynamic activity of orally dosed peptide of SEQ ID NO: 1. Since there is no dilution of blood required, and the readout is more proximal than IFNγ production, and the response is measured in the specific subset of immune cells that respond to IL-23, the pSTAT3 assay is a more sensitive pharmacodynamic readout than IFNγ.

Methods

Whole blood samples were collected in vacuette tube with lithium heparin using standard procedures at the clinical trial site. Samples were aliquoted into a pre-warmed plate and incubated for 30 mins in a 37° C. heat block. Following incubation samples were stimulated with 100 ng/mL of IL-23 for 30 mins at 37° C. Samples were then fixed for 15 mins at 37° C. with pre-warmed BD Phosflow™ lyse/fix buffer. Subsequently samples were permeabilized in 100% methanol for 15 mins at 4° C. and stained for 60 mins at room temperature with antibodies against pSTAT3 (phosphorylation site: PY705/clone: 4/P-STAT3), CD45 (clone: HI30), CD3 (clone: UCHT1), CD56 (clone: HCD56), CD4 (clone: RPA-T4), CD8 (clone: RPA-T8), CD45RA (clone: H1100) and CD26 (clone: M-A261) prior to analysis on a flow cytometer.

Results

Figure 15:
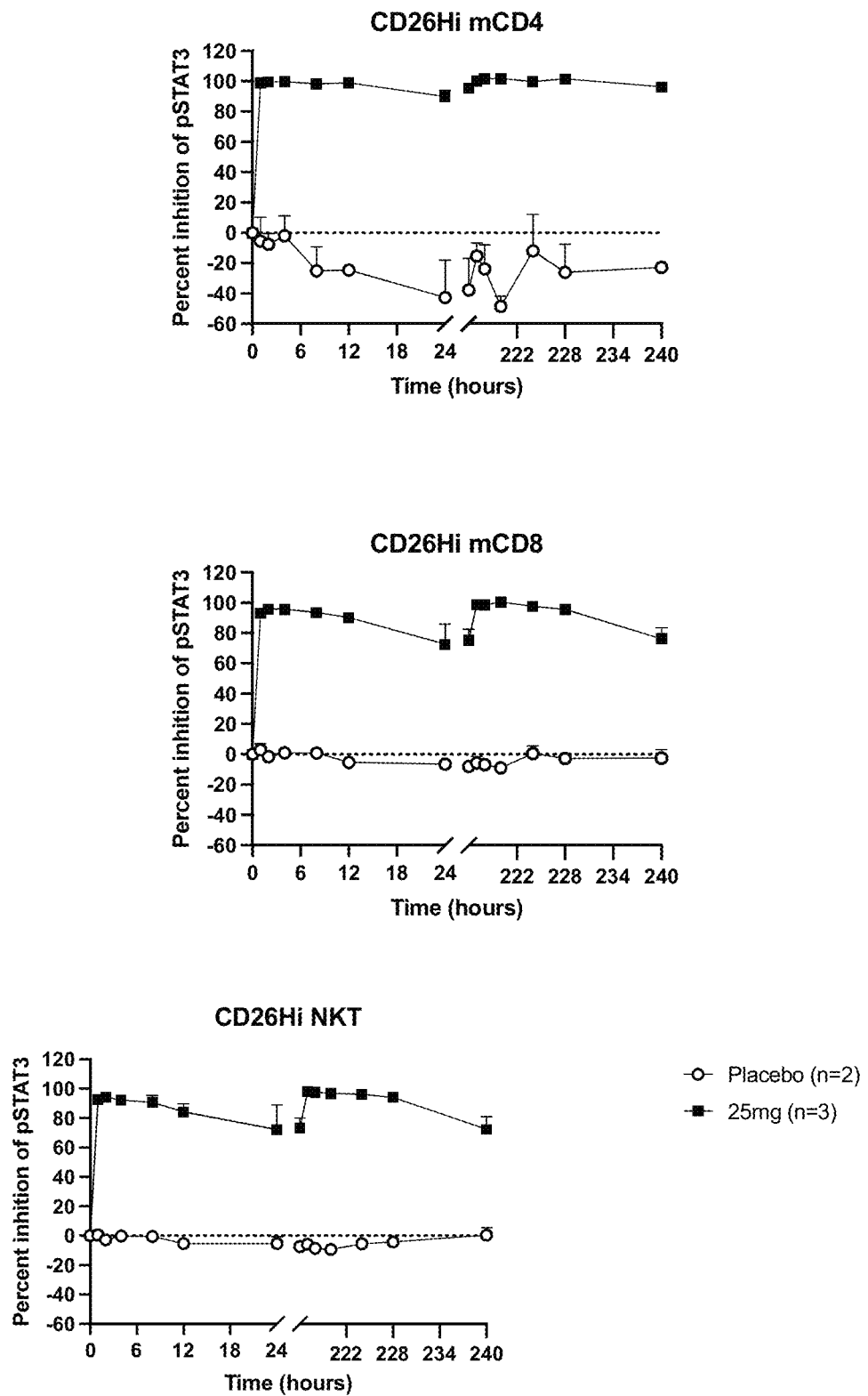
FIG. 15 shows percent inhibition of IL-23 induced pSTAT3 data (mean±SEM) from multiple indicated timepoints on Day 1 and Day 10 of the 25 mg MAD cohort.

In all 3 subjects who received 25 mg of peptide of SEQ ID NO: 1, near-complete inhibition of STAT3 phosphorylation was observed in all the analyzed immune cell subsets (memory $CD26^{high}$ $CD4^+$ T cells, memory $CD26^{high}$ $CD8^+$ T cells and $CD26^{high}$ NKT cells), while no inhibition was observed in the 2 placebo subjects (FIG. 15). These datasets demonstrate that levels of peptide of SEQ ID NO: 1 in the blood of 25 mg cohort subjects are sufficient to inhibit IL-23R signaling in blood further supporting systemic pharmacodynamic activity of peptide of SEQ ID NO: 1.

In summary, these datasets clearly demonstrate that at doses of 25 mg and above, we are seeing robust systemic pharmacodynamic activity with orally administered peptide of SEQ ID NO: 1.

The first-in-human phase 1 study systemic pSTAT3 pharmacodynamic dataset for 25 mg cohort relative to placebo is shown in FIG. 15, which illustrates the percent inhibition of IL-23 induced pSTAT3 data (mean±SEM) from multiple indicated timepoints on Day 1 and Day 10 of the 25 mg MAD cohort. There were 4 subjects dosed with the peptide of SEQ ID NO: 1 in the 25 mg cohort but one subject could not be included in the analysis because the 0 hr time point was unavailable. CD26Hi=cluster of differentiation 26 high; mCD4=memory cluster of differentiation 4; mCD8= memory cluster of differentiation 8; NKT=natural killer T cells; pSTAT3=phosphorylated signal transducer and activator of transcription 3.

In addition, each reference, including all of the U.S. patents, U.S. patent application publications, U.S. patent applications, foreign patents, foreign patent applications and non-patent publications referred to in this specification are incorporated herein by reference, in their entirety, to the extent not inconsistent with the present description. Where a conflict exists between the instant application and a reference provided herein, the instant application shall dominate.

Although the foregoing invention has been described in some detail by way of illustration and example for purposes of clarity of understanding, one of skill in the art will appreciate that certain changes and modifications can be practiced within the scope of the appended claims.

It is to be understood that the invention is not limited to the described aspects illustrated herein above and the right is reserved to the illustrated aspects and all modifications coming within the scope of the claims.

In addition, each reference, including all of the U.S. patents, U.S. patent application publications, U.S. patent applications, foreign patents, foreign patent applications and non-patent publications referred to in this specification are incorporated herein by reference, in their entirety, to the extent not inconsistent with the present description. Where a conflict exists between the instant application and a reference provided herein, the instant application shall dominate.

Although the foregoing invention has been described in some detail by way of illustration and example for purposes of clarity of understanding, one of skill in the art will appreciate that certain changes and modifications can be practiced within the scope of the appended claims.

It is to be understood that the invention is not limited to the described aspects illustrated herein above and the right is reserved to the illustrated aspects and all modifications coming within the scope of the claims.

What is claimed is:

1. A pharmaceutical composition comprising:
a peptide of SEQ ID NO: 1 or a pharmaceutically acceptable salt or solvate form thereof in an amount of from about 0.1% to about 15% (w/w) of the pharmaceutical composition; and
one or more pharmaceutically acceptable excipients.

2. The pharmaceutical composition of claim 1, wherein the peptide of SEQ ID NO: 1 or a pharmaceutically acceptable salt or solvate form thereof, has the chemical structure:

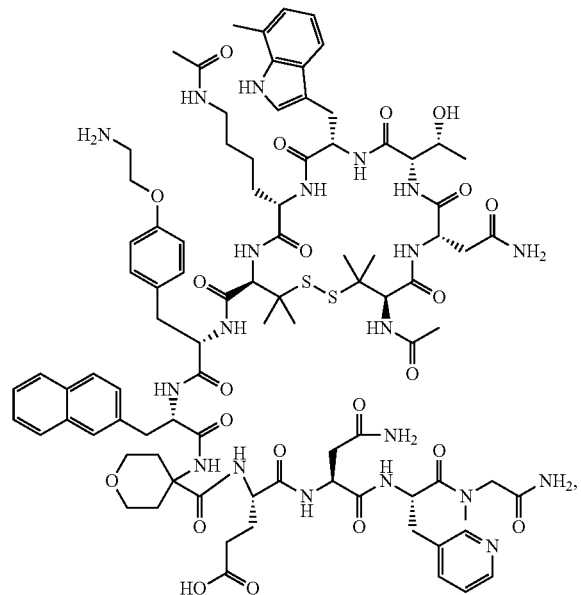 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

and wherein the peptide of SEQ ID NO: 1 or a pharmaceutically acceptable salt or solvate form thereof is a pharmaceutically acceptable salt form.

3. The pharmaceutical composition of claim 1, wherein the peptide of SEQ ID NO: 1 or a pharmaceutically acceptable salt or solvate form thereof is an acetate form.

4. The pharmaceutical composition of claim 3, wherein the acetate form is in an amorphous form.

5. The pharmaceutical composition of claim 1, wherein the amount of the peptide of SEQ ID NO: 1 or a pharmaceutically acceptable salt or solvate form thereof is from about 1 mg to about 1000 mg.

6. The pharmaceutical composition of claim 1, wherein the amount of the peptide of SEQ ID NO: 1 or a pharmaceutically acceptable salt or solvate form thereof is from about 10 mg to about 300 mg.

7. The pharmaceutical composition of claim 1, wherein the amount of the peptide of SEQ ID NO: 1 or a pharmaceutically acceptable salt or solvate form thereof is from about 25 mg to about 150 mg.

8. The pharmaceutical composition of claim 1, wherein the pharmaceutical composition further comprises an absorption enhancer.

9. The pharmaceutical composition of claim 8 comprising:
a peptide of SEQ ID NO: 1 or a pharmaceutically acceptable salt or solvate form thereof in an amount of from about 0.1% to about 15% (w/w) of the pharmaceutical composition;
an absorption enhancer in an amount from about 10% to about 60% (w/w); and
one or more pharmaceutically acceptable excipients.

10. A method of treating an inflammatory disease in a subject comprising administering to the subject a therapeutically effective amount of a pharmaceutical composition of claim 1.

11. A pharmaceutical composition comprising:
a peptide of SEQ ID NO: 1 or a pharmaceutically acceptable salt or solvate form thereof in an amount of from about 0.1% to about 20% (w/w) of the pharmaceutical composition; and
one or more pharmaceutically acceptable excipients.

12. The pharmaceutical composition of claim 11, wherein the peptide of SEQ ID NO: 1 or a pharmaceutically acceptable salt or solvate form thereof, has the chemical structure:

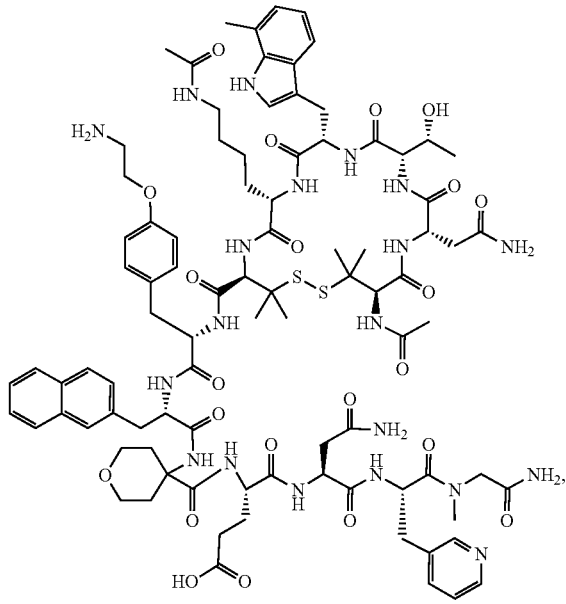 [SMILES: CC(=O)NCCCC[C@@H]1NC(=O)[C@H](Cc2c[nH]c3c(C)cccc23)NC(=O)[C@H]([C@@H](C)O)NC(=O)[C@H](CC(N)=O)NC(=O)[C@@H](NC(C)=O)C(C)(C)SSC(C)(C)[C@@H](C(=O)N[C@@H](Cc2ccc(OCCN)cc2)C(=O)N[C@@H](Cc2ccc3ccccc3c2)C(=O)NC2(C(=O)N[C@@H](CCC(=O)O)C(=O)N[C@@H](CC(N)=O)C(=O)N[C@@H](Cc3cccnc3)C(=O)N(C)CC(N)=O)CCOCC2)NC1=O]

and wherein the peptide of SEQ ID NO: 1 or a pharmaceutically acceptable salt or solvate form thereof is a pharmaceutically acceptable salt form.

13. The pharmaceutical composition of claim 12, wherein the amount of the peptide of SEQ ID NO: 1 or a pharmaceutically acceptable salt or solvate form thereof is from about 1 mg to about 1000 mg.

14. The pharmaceutical composition of claim 13, wherein the amount of the peptide of SEQ ID NO: 1 or a pharmaceutically acceptable salt or solvate form thereof is from about 10 mg to about 500 mg.

15. The pharmaceutical composition of claim 14, wherein the amount of the peptide of SEQ ID NO: 1 or a pharmaceutically acceptable salt or solvate form thereof is from about 10 mg to about 300 mg.

16. A method of treating an inflammatory disease in a subject comprising administering to the subject a therapeutically effective amount of a pharmaceutical composition of claim 11.

* * * * *

SEQUENCE LISTING

```
<160> NUMBER OF SEQ ID NOS: 1

<210> SEQ ID NO 1
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Pen
<220> FEATURE:
<221> NAME/KEY: MISC_FEATURE
<222> LOCATION: (4)..(4)
<223> OTHER INFORMATION: Xaa is W(7-Me)
<220> FEATURE:
```

```
<221> NAME/KEY: MISC_FEATURE
<222> LOCATION: (5)..(5)
<223> OTHER INFORMATION: Xaa is Lys(Ac)
<220> FEATURE:
<221> NAME/KEY: MISC_FEATURE
<222> LOCATION: (6)..(6)
<223> OTHER INFORMATION: Xaa is Pen
<220> FEATURE:
<221> NAME/KEY: MISC_FEATURE
<222> LOCATION: (7)..(7)
<223> OTHER INFORMATION: Phe is Phe[4-(2-aminoethoxy)]
<220> FEATURE:
<221> NAME/KEY: MISC_FEATURE
<222> LOCATION: (8)..(8)
<223> OTHER INFORMATION: Xaa is 2-Nal
<220> FEATURE:
<221> NAME/KEY: MISC_FEATURE
<222> LOCATION: (9)..(9)
<223> OTHER INFORMATION: Xaa is THP
<220> FEATURE:
<221> NAME/KEY: MISC_FEATURE
<222> LOCATION: (12)..(12)
<223> OTHER INFORMATION: Xaa is 3-Pal
<220> FEATURE:
<221> NAME/KEY: MISC_FEATURE
<222> LOCATION: (13)..(13)
<223> OTHER INFORMATION: Xaa is Sarc

<400> SEQUENCE: 1

Xaa Asn Thr Xaa Lys Xaa Phe Xaa Xaa Glu Asn Xaa Xaa
1               5                   10
```